United States Patent [19]
Goulet et al.

[11] Patent Number: 5,250,678
[45] Date of Patent: Oct. 5, 1993

[54] O-ARYL, O-ALKYL, O-ALKENYL AND O-ALKYNYLMACROLIDES HAVING IMMUNOSUPPRESSIVE ACTIVITY

[75] Inventors: Mark Goulet, Westfield; Frederick Wong, Glen Ridge; Peter J. Sinclair, Highland Park; Matthew J. Wyvratt, Mountainside, all of N.J.

[73] Assignee: Merck & Co., Inc., Rahway, N.J.

[21] Appl. No.: 875,036

[22] Filed: May 1, 1992

Related U.S. Application Data

[63] Continuation-in-part of Ser. No. 809,998, Dec. 18, 1991, abandoned, which is a continuation-in-part of Ser. No. 699,407, May 13, 1991, abandoned.

[51] Int. Cl.$^5$ .................. C07D 491/16; A61K 31/435
[52] U.S. Cl. ..................................... 540/456; 540/452
[58] Field of Search ................ 540/456, 452; 514/291, 514/411

[56] References Cited

U.S. PATENT DOCUMENTS

| | | | |
|---|---|---|---|
| 4,894,366 | 1/1990 | Okuhara et al. | 514/63 |
| 4,929,611 | 5/1990 | Okuhara et al. | 514/183 |
| 4,956,352 | 9/1990 | Okuhara et al. | 514/63 |
| 4,981,792 | 1/1991 | Inamine et al. | 435/119 |
| 5,011,844 | 4/1991 | Fehr | 514/291 |
| 5,064,835 | 11/1991 | Bochis et al. | 514/291 |

FOREIGN PATENT DOCUMENTS

| | | | |
|---|---|---|---|
| 0349061 | 1/1990 | European Pat. Off. | 540/456 |
| 0353678 | 2/1990 | European Pat. Off. | 540/456 |
| 0369344 | 5/1990 | European Pat. Off. | 540/456 |
| 0388152 | 9/1990 | European Pat. Off. | 540/456 |
| 0402931 | 12/1990 | European Pat. Off. | 540/456 |
| 0413532 | 2/1991 | European Pat. Off. | 540/456 |
| 0427680 | 5/1991 | European Pat. Off. | 540/456 |
| 0428365 | 5/1991 | European Pat. Off. | . |
| 0463690 | 1/1992 | European Pat. Off. | 540/456 |
| 2245891A | 1/1992 | United Kingdom | 540/456 |
| WO89/05304 | 6/1989 | World Int. Prop. O. | 540/456 |
| WO91/02736 | 3/1991 | World Int. Prop. O. | 540/456 |
| WO91/04025 | 4/1991 | World Int. Prop. O. | 540/456 |
| WO91/13889 | 9/1991 | World Int. Prop. O. | 540/456 |
| WO91/13899 | 9/1991 | World Int. Prop. O. | 540/456 |

OTHER PUBLICATIONS

Tanaka, et al., J. Am. Chem. Soc., 1987, 109 5031-5033.

Primary Examiner—Robert T. Bond
Attorney, Agent, or Firm—Charles M. Caruso; J. Eric Thies

[57] ABSTRACT

O-Aryl, O-alkyl, O-alkenyl and O-alkynyl-macrolides of the general structural Formula I:

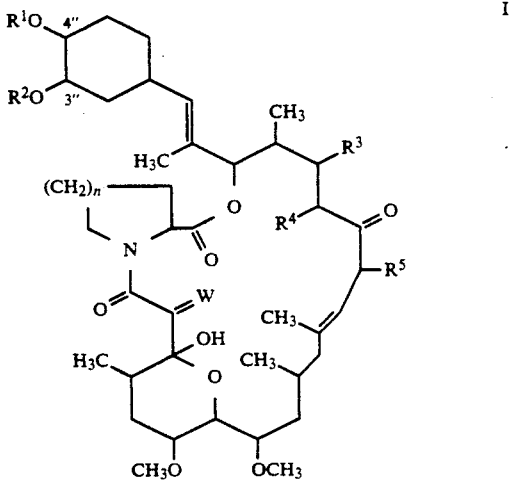

have been prepared from suitable precursors by alkylation and/or arylation at C-3" and/or C-4" of the cyclohexyl ring. These macrolide immunosuppressants are useful in a mammalian host for the treatment of autoimmune diseases, infectious diseases and/or the prevention of rejection of foreign organ transplants. In addition, these macrolide immunosuppressants are useful in the topical treatment of inflammatory and hyperproliferative skin diseases and cutaneous manifestations of immunologically-mediated illnesses. Also, these macrolides are useful in the treatment of reversible obstructive airways disease, particularly asthma; as hair revitalizing agents, especially in the treatment of male pattern alo- (Abstract continued on next page.)

pecia or alopecia senilis; in the reversal of multidrug resistance of tumor cells; in treatment of inflammation of mucosa and blood vessels, gastric ulcers, vascular damage, ischemic bowel disease, necrotizing enterocolitis, intestinal lesions associated with thermal burns; in the treatment of cytomegalovirus infection; and in the treatment of idiopathic thrombocytopenic purpura and Basedow's disease.

15 Claims, No Drawings

O-ARYL, O-ALKYL, O-ALKENYL AND O-ALKYNYLMACROLIDES HAVING IMMUNOSUPPRESSIVE ACTIVITY

SUMMARY OF THE INVENTION

This application is a continuation-in-part of copending application Ser. No. 07/809,998 filed Dec. 18, 1991, now abandoned, which in turn is a continuation-in-part of copending application Ser. No. 07/699,407, filed May 13, 1991, now abandoned.

The present invention is related to O-aryl, O-alkyl, O-alkenyl and O-alkynylmacrolides which are useful in a mammalian host for the treatment of autoimmune diseases (such as juvenile-onset or recent-onset diabetes mellitus, multiple sclerosis, rheumatoid arthritis, liver disease, posterior uveitis, allergic encephalomyelitis, and glomerulonephritis, infectious diseases and/or the prevention of rejection of foreign organ transplants, e.g. bone marrow, kidney, liver, heart, skin, small-bowel, and pancreatic-islet-cell transplants, the topical treatment of inflammatory and hyperproliferative skin diseases and cutaneous manifestations of immunologically-mediated illnesses (such as: psoriasis, atopical dermatitis, contact dermatitis and further eczematous dermatitises, seborrhoeic dermatitis, *Lichen planus*, Pemphigus, bullous Pemphigoid, *Epidermolysis bullosa, urticaria, angioedemas, vasculitides, erythemas, cutaneous eosinophilias, Lupus erythematosus* or *Alopecia areata*), reversible obstructive airways disease, particularly asthma, alopecia, inflammation of mucosa and blood vessels, cytomegalovirus infection, multidrug resistance, idiopathic thrombocytopenic purpura, and/or hepatic injury associated with ischemia.

More particularly, this invention relates to compounds of the general structural Formula I:

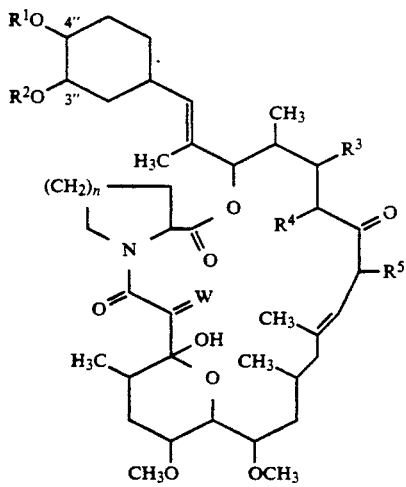

wherein $R^1$, $R^2$, $R^3$, $R^4$, $R^5$, W and n are hereinafter defined.

This invention also relates to pharmaceutical compositions containing the compounds, and to a method of use of the present compounds and other agents for the treatment and prevention of certain afflictions, diseases and illnesses.

BRIEF DESCRIPTION OF DISCLOSURES IN THE ART

Fujisawa United States, European and Japanese patents and applications (U.S. Pat. No. 4,894,366, issued Jan. 16, 1990, EPO Publication No. 0,184,162 and PBJ Disclosure 63-17884) and publications (*J. Am. Chem. Soc.*, 1987, 109, 5031 and *J. Antibiotics* 1987, 40, 1249, disclose 17-allyl-1,14-dihydroxy-12-[2'-(4"-hydroxy-3"-methoxycyclohexyl)-1'-methylvinyl]-23,25-dimethoxy-13,19,21,27-tetramethyl-11,28-dioxa-4-azatricyclo-[22.3.1.0[4,9]]octacos-18-ene-2,3,10,16-tetraone (FR-900506) (FK-506) (L-679,934), 17-ethyl-1,14-dihydroxy-12-[2'-(4"-hydroxy-3"-methoxycyclohexyl)-1'-methyl-vinyl]-23,25-dimethoxy-13,19,21,27-tetramethyl-11,28-dioxa-4-azatricyclo[22.3.1.0[4,9]]-octacos-18-ene-2,3,10,16-tetraone (FR-900520) and related compounds which are the starting materials for the preparation of the compounds described. The synthetic preparation of the aforementioned starting material (FR-900506) has been reported (*J. Am. Chem. Soc.*, 1989, 111, 1157). A Sandoz U.S. patent (U.S. Pat. No. 5,011,844) and European patent application (EPO Publication No. 0,356,399) disclose stereoisomers of FR-900506 and derivatives at the 17-position. Fisons European and WIPO patent applications (EPO Publication No. 0,323,042 and PCT Publication No. WO89/05304) disclose various derivatives of FR-900506, FR-900520 and related compounds. A Sandoz European patent application (EPO Publication No. 0,437,680) discloses chloro, bromo, iodo and azido derivatives of FR-900506, FR-900520 and related compounds. A Merck European patent application (EPO Publication No. 0,428,365) discloses various amino derivatives of FR-900506, FR-900520 and related compounds. A Fujisawa UK patent application (UK Publication No. GB 2,245,891A) discloses various aryl(lower alkyl) and heteroaryl derivatives of FR-900506, FR-900520 and related compounds.

Fujisawa United States patents (U.S. Pat. No. 4,929,611, issued May 29, 1990 and U.S. Pat. No. 4,956,352, issued Sep. 11, 1990) disclose the use of FK-506-type compounds in treating resistance to transplantation. A Sandoz European patent application (EPO Publication No. 0,315,978) discloses the use of FR-900506 and related compounds in the topical treatment of inflammatory and hyperproliferative skin diseases and of cutaneous manifestations of immunologically-mediated illness. A Fisons World patent application (PCT Publication WO 90/14826) discloses the use of FR-900506 and related compounds in the treatment of reversible obstructive airways disease, particularly asthma. A Fujisawa European patent application (EPO Publication No. 0,423,714) discloses the use of FK-506 and derivatives as hair revitalizing agents. Various studies have suggested the efficacy of FK-506 in the treatment of a number of ailments, including rheumatoid arthritis (C. Arita, et al., *Clinical exp. Immunol.*, 1990, 82, 456–461; N. Inamura, et al., *Clin. Immunol. Immunopathol.* 1988, 46, 82–90), recent-onset diabetes (N. Murase, et al., *Diabetes*, 1990, 39, 1584–86; N. Murase, et al., *Lancet*, 1990, 336, 373–74), posterior uveitis (H. Kawashima, Invest. Ophthalmul. Vis. Sci., 1988, 29, 1265–71), hepatic injury associated with ischemia (M. Sakr, et al., *Life Sci.*, 1990, 47, 687–91) allergic encephalomyelitis (K, Deguchi, et al., *Brain Nerve*, 1990, 42, 391–97), glomerulonephritis (J. McCauley, et al., *Lancet*, 1990, 335, 674), systemic lupus erythematosus (K. Takabayashi, et al., *Clin. Immunol. Immunopathol.*, 1989, 51, 110–117), multidrug resistance (M. Naito, et al., *Cancer Chemother. Pharmacol.*, 1992, 29, 195–200), inflammation of mucosa and blood vessels (PCT Publication WO91/17754), cytomegalovirus infection (UK Publication GB 2,247,620A), and idiopathic thrombocytophenic purpura and Basedow's disease (PCT Publication WO 91/19495).

BACKGROUND OF THE INVENTION

Immunoregulatory abnormalities have been shown to exist in a wide variety of "autoimmune" and chronic inflammatory diseases, including systemic lupus erythematosis, chronic rheumatoid arthritis, type 1 diabetes mellitus, inflammatory bowel disease, biliary cirrhosis, uveitis, multiple sclerosis and other disorders such as Chron's disease, ulcerative colitis, bullous pemphigoid, sarcoidosis, psoriasis, ichthyosis, and Graves ophthalmopathy. Although the underlying pathogenesis of each of these conditions may be quite different, they have in common the appearance of a variety of autoantibodies and self-reactive lymphocytes. Such self-reactivity may be due, in part, to a loss of the homeostatic controls under which the normal immune system operates.

Similarly, following a bone-marrow or an organ transplantation, the host lymphocytes recognize the foreign tissue antigens and begin to produce antibodies which lead to graft rejection.

One end result of an autoimmune or a rejection process is tissue destruction caused by inflammatory cells and the mediators they release. Antiinflammatory agents such as NSAID's and corticosteroids act principally by blocking the effect or secretion of these mediators but do nothing to modify the immunologic basis of the disease. On the other hand, cytotoxic agents such as cyclophosphamide, act in such a nonspecific fashion that both the normal and autoimmune responses are shut off. Indeed, patients treated with such nonspecific immunosuppressive agents are as likely to succumb from infection as they are from their autoimmune disease.

Cyclosporin A which was approved by the U.S. FDA in 1983 is currently the leading drug used to prevent rejection of transplanted organs. The drug acts by inhibiting the body's immune system from mobilizing its vast arsenal of natural protecting agents to reject the transplant's foreign protein. Though cyclosporin A is effective in fighting transplant rejection, it is nephrotoxic and is known to cause several undesirable side effects including kidney failure, abnormal liver function and gastrointestinal discomfort.

Newer, safer drugs exhibiting less side effects are constantly being searched for in the field.

The 23-membered tricyclo-macrolide immunosuppressant, FR-900506,

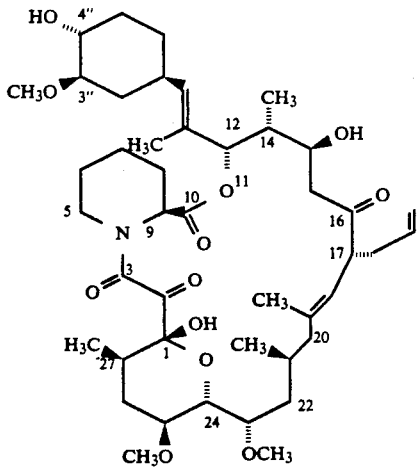

(17-allyl-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo-[22.3.1.0$^{4,9}$]-octacos-18-ene-2,3,10,16-tetraone) and related compounds which were isolated and characterized by Tanaka, Kuroda, and co-workers at Fujisawa Pharmaceutical Co. in Japan, see *J. Am. Chem. Soc.*, 1987, 109, 5031, and U.S. Pat. No. 4,894,366, issued Jan. 16, 1990) have been shown to possess exceptional immunosuppressive activity. Fujisawa United States patents (U.S. Pat. No. 4,929,611, issued May 29, 1990 and U.S. Pat. No. 4,956,352, issued Sep. 11, 1990) disclose the use of FK-506-type compounds in treating resistance to transplantation. In particular, the compound FR-900506 has been reported to be 100 times more effective than cyclosporin in the suppression of in vitro immune systems (*J. Antibiotics* 1987, 40, 1256). In addition, these compounds are reputed to possess topical activity in the treatment of inflammatory and hyperproliferative skin diseases and cutaneous manifestations of immunologically-mediated illnesses (EPO Pub. No. 0,315,978).

The compound FK-506 and related compounds further have been suggested to be useful in the treatment of obstructive airways disease, particularly asthma (PCT Publication WO 90/14826), rheumatoid arthitis (C. Arita, et al., *Clinical exp. Immunol.*, 1990, 82, 456–461; N. Inamura, et al., *Clin. Immunol. Immunopathol.* 1988, 46, 82–90), recent-onset diabetes (N. Murase, et al., *Diabetes*, 1990, 39, 1584–86; N. Murase, et al. *Lancet*, 1990, 336, 373–74), posterior uveitis (H. Kawashima, *Invest. Ophthalmol. Vis. Sci.*, 1988, 29, 1265–71), hepatic injury associated with ischemia (M. Sakr, et al., *Life Sci.*, 1990, 47, 687–91) allergic encephalomyelitis (K, Deguchi, et al., *Brain Nerve*, 1990, 42, 391–97), glomerulonephritis (J. McCauley, et al., *Lancet*, 1990, 335, 674), systemic lupus erythematosus (K. Takabayashi, et al., *Clin. Immunol. Immunopathol.*, 1989, 51, 110–117), multidrug resistance (M. Naito, et al., *Cancer Chemother. Pharmacol.*, 1992, 29, 195–200), inflammation of mucosa and blood vessels (PCT Publication WO 92/17754), cytomegalovirus infection (UK Publication GB 2,247,620A), and idiopathic thrombocytophenic purpura and Basedow's disease (PCT Publication WO 91/19495).

DETAILED DESCRIPTION OF THE INVENTION

A. Scope of the Invention

The novel compound of this invention has structural Formula I:

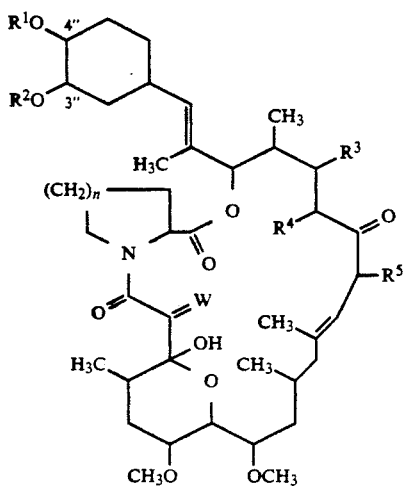

or a pharmaceutically acceptable salt thereof, wherein:
$R^1$ and $R^2$ are independently selected from:
(1) hydrogen;
(2) phenyl;
(3) substituted phenyl in which the substituents are X, Y and Z;
(4) 1- or 2- naphthyl;
(5) substituted 1- or 2- naphthyl in which the substituents are X, Y and Z;
(6) biphenyl;
(7) substituted biphenyl in which the substituents are X, Y and Z;
(8) $C_{1-10}$ alkyl;
(9) substituted $C_{1-10}$ alkyl in which one or more substituent(s) is(are) selected from:
  (a) hydroxy,
  (b) oxo,
  (c) $C_{1-6}$-alkoxy,
  (d) phenyl-$C_{1-3}$alkoxy,
  (e) substituted phenyl-$C_{1-3}$alkoxy, in which the substituents on phenyl are X, Y and Z,
  (f) —OCO—$C_{1-6}$alkyl,
  (g) —$NR^6R^7$, wherein $R^6$ and $R^7$ are independently selected from
    (i) hydrogen,
    (ii) $C_{1-10}$alkyl unsubstituted or substituted with one or more of the substituent(s) selected from:
      (a') phenyl, which is unsubstituted or substituted with X, Y and Z,
      (b') —OH,
      (c') $C_{1-6}$alkoxy,
      (d') —$CO_2H$,
      (e') —$CO_2$—$C_{1-6}$alkyl,
      (f') —$C_{3-7}$cycloalkyl, and
      (g') —$OR^{11}$,
    (iii) $C_{3-10}$alkenyl unsubstituted or substituted with one or more of the substituent(s) selected from:
      (a') phenyl, which is unsubstituted or substituted with X, Y and Z,
      (b') —OH,
      (c') $C_{1-6}$alkoxy,
      (d') —$CO_2H$,
      (e') —$CO_2$—$C_{1-6}$alkyl,
      (f') —$C_{3-7}$cycloalkyl, and
      (g') —$OR^{11}$,
    (iv) or where $R^6$ and $R^7$ and the N to which they are attached can form an unsubstituted or substituted 3-7-membered saturated heterocyclic ring which can include one or two additional heteroatoms independently selected from the group consisting of O, $S(O)_p$, $NR^{14}$, wherein $R^{14}$ is hydrogen or $C_{1-6}$ alkyl unsubstituted or substituted by phenyl, and p is 0, 1 or 2, the ring being selected from the group consisting of: aziridine, morpholine, thiomorpholine, thiomorpholine-oxide, thiomorpholine-dioxide, piperidine, pyrrolidine, and piperazine,
  (h) —$NR^6CO$—$C_{1-6}$alkyl-$R^7$, wherein $R^6$ is as defined above,
  (i) —$NR^6CO_2$—$C_{1-6}$alkyl-$R^7$,
  (j) —$NR^6CONR^6R^7$,
  (k) —$OCONR^6R^7$,
  (l) —$COOR^6$,
  (m) —CHO,
  (n) phenyl,
  (o) substituted phenyl in which the substituents are X, Y and Z,
  (p) phenyloxy,
  (q) substituted phenyloxy in which the substituents are X, Y and Z,
  (r) 1- or 2- naphthyl,
  (s) substituted 1- or 2- napththyl in which the substituents are X, Y and Z,
  (t) biphenyl
  (u) substituted biphenyl in which the substituents are X, Y and Z;
  (v) —$OR^{11}$, and
  (w) —$S(O)_p$—$C_{1-6}$alkyl;
(10) $C_{3-10}$ alkenyl;
(11) substituted $C_{3-10}$ alkenyl in which one or more substituent(s) is(are) selected from:
  (a) hydroxy,
  (b) oxo,
  (c) $C_{1-6}$alkoxy,
  (d) phenyl-$C_{1-3}$alkoxy,
  (e) substituted phenyl-$C_{1-3}$alkoxy, in which the substituents on phenyl are X, Y and Z,
  (f) —OCO—$C_{1-6}$alkyl,
  (g) —$NR^6R^7$, wherein $R^6$ and $R^7$ are as defined above
  (h) —$NR^6CO$—$C_{1-6}$alkyl, wherein $R^6$ is as defined above,
  (i) —$COOR^6$, wherein $R^6$ is as defined above,
  (j) —CHO,
  (k) phenyl,
  (l) substituted phenyl in which the substituents are X, Y and Z,
  (m) 1- or 2-naphthyl,
  (n) substituted 1- or 2-naphthyl in which the substituents are X, Y and Z,
  (o) biphenyl,
  (p) substituted biphenyl in which the substituents are X, Y and Z,
  (q) —$OR^{11}$, and
  (r) —$S(O)_p$—$C_{1-6}$alkyl;
(12) $C_{3-10}$alkynyl;

(13) substituted $C_{3-10}$alkynyl in which one or more substituent(s) is(are) selected from:
(a) hydroxy,
(b) oxo,
(c) $C_{1-6}$alkoxy,
(d) phenyl-$C_{1-3}$alkoxy,
(e) substituted phenyl-$C_{1-3}$alkoxy, in which the substituents on phenyl are X, Y and Z,
(f) —OCO—$C_{1-6}$alkyl,
(g) —$NR^6R^7$, wherein $R^6$ and $R^7$ are as defined above,
(h) —$NR^6$CO—$C_{1-6}$alkyl, wherein $R^6$ is as defined above,
(i) —$COOR^6$, wherein $R^6$ is as defined above,
(j) —CHO,
(k) phenyl,
(l) substituted phenyl in which the substituents are X, Y and Z,
(m) 1- or 2-naphthyl,
(n) substituted 1- or 2-naphthyl in which the substituents are X, Y and Z,
(o) biphenyl,
(p) substituted biphenyl in which the substituents are X, Y, and Z, and
(q) —$OR^{11}$;
with the proviso that $R^1$ and $R^2$ are not simultaneously hydrogen, methyl or combinations thereof;
$R^3$ is hydrogen, hydroxy, —$OR^{11}$ or $C_{1-6}$ alkoxy;
$R^4$ is hydrogen, or $R^3$ and $R^4$ taken together form a double bond;
$R^5$ is methyl, ethyl, propyl or allyl;
$R^{11}$ is selected from:
(a) —$PO(OH)O^-M^+$, wherein $M^+$ is a positively charged inorganic or organic counterion,
(b) —$SO_3^-M^+$,
(c) —$CO(CH_2)_qCO_2^-M^+$, wherein q is 1-3, and
(d) —CO—$C_{1-6}$alkyl-$NR^6R^7$, wherein $R^6$ and $R^7$ are as defined above and the alkyl is unsubstituted or substituted with one or more substituents selected from:
(i) hydroxy,
(ii) $C_{1-6}$alkoxy,
(iii) —$NR^{16}R^{17}$, wherein $R^{16}$ and $R^{17}$ are independently selected from:
(a') hydrogen, and
(b') $C_{1-6}$alkyl,
(iv) —$COOR^6$, wherein $R^6$ is as defined above,
(v) phenyl,
(vi) substituted phenyl in which the substituents are X, Y and Z,
(vii) —SH, and
(viii) —S—$C_{1-6}$alkyl;
W is O or (H, OH);
X, Y and Z independently are selected from:
(a) hydrogen,
(b) $C_{1-7}$ alkyl,
(c) $C_{2-6}$ alkenyl,
(d) halogen,
(e) —$(CH_2)_m$—$NR^6R^7$, wherein $R^6$ and $R^7$ are as defined above, and m is 0 to 2,
(f) —CN,
(g) —CHO,
(h) —$CF_3$,
(i) —$SR^8$, wherein $R^8$ is hydrogen, $C_{1-6}$alkyl, trifluoromethyl, or phenyl,
(j) —$SOR^8$, wherein $R^8$ is as defined above,
(k) —$SO_2R^8$, wherein $R^8$ is as defined above,
(l) —$CONR^6R^7$, wherein $R^6$ and $R^7$ are as defined above,
(m) $R^9O(CH_2)_m$— wherein $R^9$ is hydrogen, $C_{1-3}$ alkyl, hydroxy-$C_{2-3}$alkyl, trifluoromethyl, phenyl or naphthyl and m is as defined above,
(n) —$CH(OR^{12})(OR^{13})$, wherein $R^{12}$ and $R^{13}$ are $C_{1-3}$alkyl or taken together form an ethyl or propyl bridge,
(o)

wherein $R^9$ and m are as defined above, and
(p)

wherein $R^9$ and m are as defined above, and
(q) —$OR^{11}$;
or any two of adjacent X, y and Z can be joined to form a ring having 5, 6 or 7 ring atoms, said ring atoms comprising 1 or 2 oxygen atoms, the remaining ring atoms being carbon, selected from the group consisting of: dioxolanyl, dihydrofuranyl, dihydropyranyl, and dioxanyl; and
n is 1 or 2.

The compounds of the present invention have asymmetric centers and this invention includes all of the optical isomers and mixtures thereof.

In addition compounds with carbon-carbon double bonds may occur in Z- and E- forms with all isomeric forms of the compounds being included in the present invention.

When any variable (e.g., alkyl, aryl, $R^6$, $R^7$, $R^8$, $R^9$, $R^{10}$, $R^{11}$, etc.) occurs more than one time in any variable or in Formula I, its definition on each occurrence is independent of its definition at every other occurrence.

As used herein, the term "alkyl" includes those alkyl groups of a designated number of carbon atoms of either a straight, branched, or cyclic configuration. Examples of "alkyl" include methyl, ethyl, propyl, isopropyl, butyl, sec-and tert-butyl, pentyl, hexyl, heptyl, cyclopropyl, cyclobutyl, cyclopentyl, cyclohexyl, cycloheptyl, norbornyl, and the like. "Alkoxyl" represents an alkyl group of indicated number of carbon atoms attached through an oxygen bridge, such as methoxy, ethoxy, propoxy, butoxy and pentoxy.

"Alkanoyl" is intended to include those alkylcarbonyl groups of specified number of carbon atoms, which are exemplified by formyl, acetyl, propanoyl and butyryl; "alkanoyloxy" is intended to include those alkylcarbonyl groups of specified number of carbon atoms attached through an oxygen bridge, which are exemplified by formyloxy, acetoxy, propionoyloxy, and butyryloxy. "Alkenyl" is intended to include hydrocarbon chains of a specified number of carbon atoms of either a straight- or branched -configuration and at least one unsaturation, which may occur at any point along the chain, such as ethenyl, propenyl, butenyl, pentenyl, dimethyl pentenyl, and the like, and includes E and Z forms, where applicable; and "arylalkyl" represents aryl groups as herein defined which are attached through a straight or branched chain alkyl group of from one to six carbon atoms, such as, for example, benzyl, phenethyl, 3,3-diphenylpropyl, and the like. "Halogen", as used herein, means fluoro, chloro, bromo and iodo.

As will be understood by those skilled in the art, pharmaceutically acceptable salts include, but are not limited to salts with inorganic acids such as hydrochloride, sulfate, phosphate, diphosphate, hydrobromide, and nitrate or slats with an organic acid such as malate, maleate, fumarate, tartrate, succinate, citrate, acetate, lactate, methanesulfonate, p-toluenesulfonate or palmoate, salicylate and stearate. Similarly pharmaceutically acceptable cations include, but are not limited to sodium, potassium, calcium, aluminum, lithium and ammonium (especially ammonium salts with amines of the formula $HNR^6R^7$).

One embodiment of the present invention encompasses the compounds of Formula I wherein: $R^1$ and $R^2$ are independently selected from:
(1) hydrogen;
(2) methyl;
(3) phenyl;
(4) substituted phenyl in which the substituents are X, Y and Z;
(5) 1- or 2-naphthyl;
(6) substituted 1- or 2-naphthyl in which the substituents are X, Y and Z;
(7) biphenyl; and
(8) substituted and biphenyl in which the substituents are X, Y and Z;
with the proviso that $R^1$ and $R^2$ are not simultaneously hydrogen, methyl or combinations thereof;
$R^3$ is hydrogen, hydroxy, or $C_{1-6}$ alkoxy;
$R^4$ is hydrogen, or $R^3$ and $R^4$ taken together form a double bond;
$R^5$ is methyl, ethyl, propyl or allyl;
$R^{11}$ is selected from:
 (a) $-PO(OH)O^-M^+$, wherein $M^+$ is a positively charged inorganic or organic counterion,
 (b) $-SO_3^-M^+$,
 (c) $-CO(CH_2)_qCO_2^-M^+$, wherein q is 1-3, and
 (d) $-CO-C_{1-6}alkyl-NR^6R^7$, wherein $R^6$ and $R^7$ are as defined below and the alkyl is unsubstituted or substituted with one or more substituents selected from:
  (i) hydroxy,
  (ii) $C_{1-6}$alkoxy,
  (iii) $-NR^{16}R^{17}$, wherein $R^{16}$ and $R^{17}$ are independently selected from:
   (a') hydrogen, and
   (b') $C_{1-6}$alkyl,
  (iv) $-COOR^6$, wherein $R^6$ is as defined below,
  (v) phenyl,
  (vi) substituted phenyl in which the substituents are X, Y and Z,
  (vii) $-SH$, and
  (viii) $-S-C_{1-6}$alkyl;
W is O or (H, OH);
X, Y and Z are independently, selected from:
 (a) hydrogen,
 (b) $C_{1-7}$ alkyl,
 (c) $C_{2-6}$ alkenyl,
 (d) halogen,
 (e) $-(CH_2)_m-NR^6R^7$, wherein $R^6$ and $R^7$ are, independently selected from
  (i) hydrogen, or
  (ii) $C_{1-6}$ alkyl unsubstituted or substituted with phenyl, and m is 0 to 2,
 (f) $-CN$,
 (g) $-CHO$,
 (h) $-CF_3$,
 (i) $-SR^8$, wherein $R^8$ is hydrogen, $C_{1-6}$alkyl, trifluoromethyl, or phenyl,
 (j) $-SOR^8$, wherein $R^8$ is as defined above,
 (k) $-SO_2R^8$, wherein $R^8$ is as defined above,
 (l) $-CONR^6R^7$, wherein $R^6$ and $R^7$ are as defined above,
 (m) $R^9O(CH_2)_m-$ wherein $R^9$ is hydrogen, $C_{1-3}$ alkyl, hydroxy-$C_{2-3}$alkyl, trifluoromethyl, phenyl or naphthyl and m is as defined above,
 (n) $-CH(OR^{12})(OR^{13})$, wherein $R^{12}$ and $R^{13}$ are $C_{1-3}$ alkyl or taken together form an ethyl or propyl bridge,
 (o)

wherein $R^9$ and m are as defined above, and
 (p)

wherein $R^9$ and m are as defined above, and
 (q) $-OR^{11}$;
or any two of adjacent X, Y and Z can be joined to form a ring having 5, 6 or 7 ring atoms, said ring atoms comprising 1 or 2 oxygen atoms, the remaining ring atoms being carbon, selected from the group consisting of: dioxolanyl, dihydrofuranyl, dihydropyranyl, and dioxanyl; and
n is 1 or 2.

Another embodiment of the present invention encompasses the compounds of Formula I wherein:
$R^1$ and $R^2$ are independently selected from:
(1) hydrogen;
(2) $C_{1-10}$ alkyl;
(3) substituted $C_{1-10}$alkyl in which one or more substituent(s) is (are) selected from:
 (a) hydroxy,
 (b) oxo,
 (c) $C_{1-6}$-alkoxy,
 (d) phenyl-$C_{1-3}$alkoxy,
 (e) substituted phenyl-$C_{1-3}$alkoxy, in which the substituents on phenyl are X, Y and Z,
 (f) $-OCO-C_{1-6}$alkyl,
 (g) $-NR^6R^7$, wherein $R^6$ and $R^7$ are independently selected from
  (i) hydrogen,
  (ii) $C_{1-10}$alkyl unsubstituted or substituted with one or more of the substituent(s) selected from:
   (a') phenyl, which is unsubstituted or substituted with X, Y and Z,
   (b') $-OH$,
   (c') $C_{1-6}$alkoxy,
   (d') $-CO_2H$,
   (e') $-CO_2-C_{1-6}$alkyl,
   (f') $-C_{3-7}$cycloalkyl, and
   (g') $-OR^{11}$,
  (iii) $C_{3-10}$alkenyl unsubstituted or substituted with one or more of the substituent(s) selected from:
   (a') phenyl, which is unsubstituted or substituted with X, Y and Z, (b') —OH,
(c') $C_{1-6}$alkoxy,
(d') —$CO_2$H,
(e') —$CO_2$—$C_{1-6}$alkyl,
(f') —$C_{3-7}$cycloalkyl, and
(g') —$OR^{11}$,
(iv) or where $R^6$ and $R^7$ and the N to which they are attached can form an unsubstituted or substituted 3–7-membered saturated heterocyclic ring which can include one or two additional heteroatoms independently selected from the group consisting of O, $S(O)_p$, $NR^{14}$, wherein $R^{14}$ is hydrogen or $C_{1-6}$ alkyl unsubstituted or substituted by phenyl, and p is 0, 1 or 2, the ring being selected from the group consisting of: aziridine, morpholine, thiomorpholine, thiomorpholine-oxide, thiomorpholine-dioxide, piperidine, pyrrolidine, and piperazine,
(h) —$NR^6CO$—$C_{1-6}$alkyl—$R^7$, wherein $R^6$ is as defined above,
(i) —$NR^6CO_2$—$C_{1-6}$alkyl—$R^7$,
(j) —$NR^6CONR^6R^7$,
(k) —$OCONR^6R^7$,
(l) —$COOR^6$,
(m) —CHO,
(n) phenyl,
(o) substituted phenyl in which the substituents are X, Y and Z,
(p) phenyloxy,
(q) substituted phenyloxy in which the substituents are X, Y and Z,
(r) 1- or 2-naphthyl,
(s) substituted 1- or 2-naphthyl in which the substituents are X, Y and Z,
(t) biphenyl
(u) substituted biphenyl in which the substituents are X, Y and Z;
(v) —$OR^{11}$, and
(w) —$S(O)_p$—$C_{1-6}$alkyl;
(4) $C_{3-10}$ alkenyl;
(5) substituted $C_{3-10}$ alkenyl in which one or more substituent(s) is (are) selected from:
(a) hydroxy,
(b) oxo,
(c) $C_{1-6}$alkoxy,
(d) phenyl-$C_{1-3}$alkoxy,
(e) substituted phenyl-$C_{1-3}$alkoxy, in which the substituents on phenyl are X, Y and Z,
(f) —OCO—$C_{1-6}$alkyl,
(g) —$NR^6R^7$, wherein $R^6$ and $R^7$ are as defined above
(h) —$NR^6CO$—$C_{1-6}$alkyl, wherein $R^6$ is as defined above,
(i) —$COOR^6$, wherein $R^6$ is as defined above,
(j) —CHO,
(k) phenyl,
(l) substituted phenyl in which the substituents are X, Y and Z,
(m) 1- or 2-naphthyl,
(n) substituted 1- or 2-naphthyl in which the substituents are X, Y and Z,
(o) biphenyl,
(p) substituted biphenyl in which the substituents are X, Y and Z,
(q) —$OR^{11}$, and
(r) —$S(O)_p$—$C_{1-6}$alkyl;
(6) $C_{3-10}$alkynyl;
(7) substituted $C_{3-10}$alkynyl in which one or more substituent(s) is (are) selected from:
(a) hydroxy,
(b) oxo,
(c) $C_{1-6}$alkoxy,
(d) phenyl-$C_{1-3}$alkoxy,
(e) substituted phenyl-$C_{1-3}$alkoxy, in which the substituents on phenyl are X, Y and Z,
(f) —OCO—$C_{1-6}$alkyl,
(g) —$NR^6R^7$, wherein $R^6$ and $R^7$ are as defined above,
(h) —$NR^6CO$—$C_{1-6}$alkyl, wherein $R^6$ is as defined above,
(i) —$COOR^6$, wherein $R^6$ is as defined above,
(j) —CHO,
(k) phenyl,
(l) substituted phenyl in which the substituents are X, Y and Z,
(m) 1- or 2-naphthyl,
(n) substituted 1- or 2-naphthyl in which the substituents are X, Y and Z,
(o) biphenyl,
(p) substituted biphenyl in which the substituents are X, Y and Z, and
(q) —$OR^{11}$;
with the proviso that $R^1$ and $R^2$ are not simultaneously hydrogen, methyl or combinations thereof;
$R^3$ is hydrogen, hydroxy, —$OR^{11}$ or $C_{1-6}$ alkoxy;
$R^4$ is hydrogen, or $R^3$ and $R^4$ taken together form a double bond;
$R^5$ is methyl, ethyl, propyl or allyl;
$R^{11}$ is selected from:
(a) —$PO(OH)O^-M^+$, wherein $M^+$ is a positively charged inorganic or organic counterion,
(b) —$SO_3^-M^+$,
(c) —$CO(CH_2)_qCO_2^-M^+$, wherein q is 1–3, and
(d) —CO—$C_{1-6}$alkyl—$NR^6R^7$, wherein $R^6$ and $R^7$ are as defined above and the alkyl is unsubstituted or substituted with one or more substituents selected from:
(i) hydroxy,
(ii) $C_{1-6}$alkoxy,
(iii) —$NR^{16}R^{17}$, wherein $R^{16}$ and $R^{17}$ are independently selected from:
(a') hydrogen, and
(b') $C_{1-6}$alkyl,
(iv) —$COOR^6$, wherein $R^6$ is as defined above,
(v) phenyl,
(vi) substituted phenyl in which the substituents are X, Y and Z,
(vii) —SH, and
(viii) —S—$C_{1-6}$alkyl;
W is O or (H, OH);
X, Y and Z independently are selected from:
(a) hydrogen,
(b) $C_{1-7}$ alkyl,
(c) $C_{2-6}$ alkenyl,
(d) halogen,
(e) —$(CH_2)_m$—$NR^6R^7$, wherein $R^6$ and $R^7$ are as defined above, and m is 0 to 2,
(f) —CN,
(g) —CHO,
(h) —$CF_3$,
(i) —$SR^8$, wherein $R^8$ is hydrogen, $C_{1-6}$alkyl, trifluoromethyl, or phenyl,
(j) —$SOR^8$, wherein $R^8$ is defined above,
(k) —$SO_2R^8$, wherein $R^8$ is as defined above, (l) —CONR⁶R⁷, wherein R⁶ and R⁷ are as defined above,
(m) R⁹O(CH₂)ₘ- wherein R⁹ is hydrogen, C₁₋₃ alkyl, hydroxy-C₂₋₃alkyl, trifluoromethyl, phenyl or naphthyl and m is as defined above,
(n) —CH(OR¹²)(OR¹³), wherein R¹² and R¹³ are C₁₋₃alkyl or taken together form an ethyl or propyl bridge,
(o)

wherein R⁹ and m are as defined above, and
(p)

wherein R⁹ and m are as defined above, and
(q) —OR¹¹;
or any two of adjacent X, Y and Z can be joined to form a ring having 5, 6 or 7 atoms, said ring atoms comprising 1 or 2 oxygen atoms, the remaining ring atoms being carbon, selected from the group consisting of: dioxolanyl, dihydrofuranyl, dihydropyranyl, and dioxanyl; and
n is 1 or 2.

In the present invention it is preferred that in compounds of Formula I:
R¹ and R² are independently selected from:
(1) hydrogen;
(2) phenyl;
(3) substituted phenyl in which the substituents are X, Y and Z;
(4) 1- or 2-naphthyl;
(5) substituted 1- or 2-naphthyl in which the substituents are X, Y and Z;
(6) C₁₋₁₀ alkyl;
(7) substituted C₁₋₁₀ alkyl in which one or more substituent(s) is (are) selected from
  (a) hydroxy,
  (b) oxo,
  (c) C₁₋₆-alkoxy,
  (d) phenyl-C₁₋₃alkoxy,
  (e) substituted phenyl—C₁₋₃alkoxy, in which the substituents on phenyl are X, Y and Z,
  (f) —OCO—C₁₋₆alkyl,
  (g) —NR⁶R⁷, wherein R⁶ and R⁷ are independently selected from
    (i) hydrogen,
    (ii) C₁₋₁₀alkyl unsubstituted or substituted with one or more of the substituent(s) selected from:
      (a') phenyl, which is unsubstituted or substituted with X, Y and Z,
      (b') —OH,
      (c') C₁₋₆alkoxy,
      (d') —CO₂H,
      (e') —CO₂—C₁₋₆alkyl,
      (f') —C₃₋₇cycloalkyl, and
      (g') —OR¹¹,
    (iii) C₃₋₁₀alkenyl unsubstituted or substituted with one or more of the substituent(s) selected from:
      (a') phenyl, which is unsubstituted or substituted with X, Y and Z,
      (b') —OH,
      (c') C₁₋₆alkoxy,
      (d') —CO₂H,
      (e') —CO₂—C₁₋₆alkyl,
      (f') —C₃₋₇cycloalkyl, and
      (g') —OR¹¹,
    (iv) or where R⁶ and R⁷ and the N to which they are attached may form an unsubstituted or substituted 3–7-membered saturated heterocyclic ring which may
    include one or two additional heteroatoms independently selected from the group consisting of O, S(O)ₚ, NR¹⁴, wherein R¹⁴ is hydrogen or C₁₋₆ alkyl unsubstituted or substituted by phenyl, and p is 0, 1 or 2, the ring being selected from the group consisting of: aziridine, morpholine, thiomorpholine, thiomorpholine-oxide, thiomorpholine-dioxide, piperidine, pyrrolidine, and piperazine,
  (h) —NR⁶CO—C₁₋₆alkyl-R⁷, wherein R⁶ is as defined above,
  (i) —NR⁶CO₂—C₁₋₆alkyl-R⁷,
  (j) —NR⁶CONR⁶R⁷,
  (k) —OCONR⁶R⁷,
  (l( —COOR⁶,
  (m) —CHO,
  (n) phenyl,
  (o) substituted phenyl in which the substituents are X, Y and Z,
  (p) phenyloxy,
  (q) substituted phenyloxy in which the substituents are X, Y and Z,
  (r) 1- or 2- naphthyl,
  (s) substituted 1- or 2- and naphthyl in which the substituents are X, Y and Z, and
  (t) —OR¹¹;
(8) C₃₋₁₀ alkenyl;
(9) subsituted C₃₋₁₀ alkenyl in which one or more substituent(s) is(are) selected from:
  (a) hydroxy,
  (b) oxo,
  (c) C₁₋₆ alkoxy,
  (d) —OCOC₁₋₆ alkyl,
  (e) C₂₋₈ alkenyl,
  (f) phenyl,
  (g) substituted phenyl in which the substituents are X, Y and Z,
  (h) 1- or 2- naphthyl, and
  (i) substituted 1- or 2- naphthyl in which the substituents are X, Y and Z,
(10) C₃₋₁₀ alkynyl;
(11) substituted C₃₋₁₀ alkynyl in which one or more substituent(s) is(are) selected from:
  (a) hydroxy,
  (b) oxo,
  (c) C₁₋₆ alkoxy,
  (d) —OCOC₁₋₆ alkyl,
  (e) phenyl,
  (f) substituted phenyl in which the substituents are X, Y and Z,
  (g) 1- or 2- naphthyl, and
  (h) substitued 1- or 2- naphthyl in which the subsitutens are X, Y and Z;
with the proviso that R¹ and R² are not simultaneosuly hydrogen, methyl or combinations thereof;
R³ is hydrogen, or hydroxy;

$R^4$ is hydrogen;
$R^5$ is ethyl, propyl or allyl;
$R^{11}$ is selected from:
(a) —PO(OH)O$^-$M$^{30}$, wherein M$^+$ is a positively charged inorganic or organic ounterion,
(b) —SO$_3^-$M$^+$,
(c) —CO(CH$_2$)$_q$CO$_2^-$M$^{30}$, wherein q is 1-3, and
(d) —CO—C$_{1-6}$alkyl—NR$^6$R$^7$, wherein R$^6$ and R$^7$ are as defined above and the alkyl is unsubstituted or substituted with one or more substitutents selected from:
  (i) hydroxy,
  (ii) C$_{1-6}$alkoxy,
  (iii) —NR$^{16}$R$^{17}$, wherein R$^{16}$ and R$^{17}$ are independently selected from:
    (a') hydrogen, and
    (b') C$_{1-6}$alkyl,
  (iv) —COOR$^6$, wherein R$^6$ is as defined above,
  (v) phenyl,
  (vi) substituted phenyl in which the substituents are X, Y and Z,
  (vii) —SH, and
  (viii) —S—C$_{1-6}$alkyl;
W is O or (H, OH);
X. Y and Z independently are selected from:
  (a) hydrogen,
  (b) C$_{1-7}$ alkyl,
  (c) C$_{2-6}$ alkenyl,
  (d) halogen,
  (e) —CN,
  (f) —CHO,
  (g) —CF$_3$,
  (h) —SR$^8$, wherein R$^8$ is hydrogen, C$_{1-6}$alkyl, trifluoromethyl, or phenyl,
  (i) —CONR$^6$R$^7$, wherein R$^6$ and R$^7$ are as defined above,
  (j) R$^9$O(CH$_2$)$_m$- wherein R$^9$ is hydrogen, C$_{1-3}$ alkyl, hydroxy-C$_{2-3}$alkyl, trifluoromethyl, phenyl or naphthyl and m is as defined above,
  (k) —CH(OR$^{12}$)(OR$^{13}$), wherein R$^{12}$ and R$^{13}$ are C$_{1-3}$alkyl or taken together form an ethyl or propyl bridge,
  (l)

wherein R$^9$ and m are as defined above,
  (m)

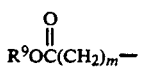

wherein R$^9$ and m are as defined above, and;
  (n) —OR$^{11}$;
or any two of adjacent X, Y and Z may be joined to form a ring having 5, 6 or 7 ring atoms, said ring atoms comprising 1 or 2 oxygen atoms, the remaining ring atoms being carbon, selected from the group consisting of: dioxolanyl, dihydrofuranyl, dihydropyranyl, and dixoanyl; and
n is 2;
and pharmaceutically acceptable salts thereof.

Representative compounds of the present invention include the compounds identified as follows:
17-Ethyl-1,14-dihydroxy-12-[2'-(4''-phenyloxy-3''-methoxycyclohexyl)-1'-methylvinyl]-23,25-dimethoxy-13, 19,21,27-tetramethyl-11,28-dioxa-4-azatricyclo-[22.3.1.0$^{4,9}$]octacos-18-ene-2,3,10,16-tetraone;

17-Ethyl-1,14-dihydroxy-12-[2'-(3''-phenyloxy-4''-hydroxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone;

17- Ethyl-1,14-dihydroxy-12-[2'-(4''-phenyloxy-3''-hydroxycyclohexyl)-1'-methylvinyl]-23,25-dimethoxy-13,19,21,27-tetramethyl-11,28-dioxa-4-azatricyclo-[22.3.1.0$^{4,9}$octacos-18-ene-2,3,10,16-tetraone;

17-Ethyl-1,14-dihydroxy-12-[2'-(4''-(4'''-fluor ophenyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4''-(4'''-chlor ophenyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4''-(4'''-methy lphenyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(3''-(4'''-methy lphenyloxy)-4''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4''-(4'''-methylphenyl oxy)-3''-hydroxycyclohexyl)-1'-methylvinyl]-23,-25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4''-(4'''-phenox yphenyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4''-(4'''-phenox yphenyloxy)-3''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(3''-(4'''-phenoxyphenyl oxy)-4''-hydroxycyclohexyl)-1'-methylvinyl]-23,-25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4''-(naphth-1-y loxy)-3''-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone;

17-Ethyl-1,14-dihydroxy-12-[2'-(3''-(naphth-1-y loxy)-4''-hydroxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone;

17-Ethyl-1,14-dihydroxy-12-[2'-(4''-(naphth-1-yloxy)-3''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4"-)naphth-2-yloxy)-3"-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone;

17-Ethyl-1,14-dihydroxy-12-[2'-(4"-(naphth-2-yloxy)-3"-hydroxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone;

17-Ethyl-1,14-dihydroxy-12-[2'-(3"-(napth-2-yloxy)-4"-hydrocyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone;

17-Ethyl-1-hydroxy-12-[2'-(4"-(naphth-2-yloxy)-3"-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone;

17-Ethyl-1,14-dihydroxy-12-[2'-(4"-(6'''-methoxynapht-h-2-yloxy)-3"-methoxycyclohexyl)-1'-methylvinyl]-23,25-dimethoxy-13,19,21,k27-tetramethyl-11,28-dioxa-4-azatricyclo[22.3.1.0$^{4,9}$]octacos-18-ene-2,3,10,16tetraone;

17-Ethyl-1,14-dihydroxy-12-[2'-(3"-(6'''-methoxynaphth-2-yloxy)-4"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4"-(6'''-methoxynaphth-2-yloxy)-3"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(3"-(4'''-methoxyphenyloxy)-4"-hydroxycyclohexyl)-1'-methylvinyl]-23,15-dimethoxy-13,19,21,27-tetramethyl-11,28-dioxa-4-azatricyclo[22.3.1.0$^{4,9}$]octacos-18-ene,2,3,10,16-tetraone;

17-Ethyl-1,14-dihydroxy-12-[2'-(4"-(4'''-methoxyphenyloxy)-3"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(3"-(3'''-methoxyphenyloxy)-4"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4"-(3'''-methoxyphenyloxy)-3"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(3"-(4'''-hydroxyphenyloxy)-4"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4"-(4'''-hydroxyphenyloxy)-3"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4"-(6'''-hydroxynaphth-2-yloxy)-3"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(3"-(6''''-hydroxynaphth-2-yloxy)-4"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4"-(3''',4''''-dichlorophenyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4"-(phenanthr-9-yloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12--[2'-(4"-(3''',4''''-methylenedioxyphenyloxy)-3"-methoxycyclohexyl)-1'-methylvinyl[-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4'--(2''',3'''-dihydrobenzofuran-5-yloxy)-3"-methoxycyclohexyl)-1'-methylvinly]-23,25-dimethoxy-13,19,21,27-tetramethyl-11,28-dioxa-4-azatricyclo[22.3.1.0$^{4,9}$]octacos-18-ene-2,3,10,16-tetraone;

17-Allyl-1,14-dihydroxy-12-[2'-(4"-(naphth-2-yloxy)-3"-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone;

17-Ethyl-1,14-dihydroxy-12-[2'-(4"-(1''',4''''-benzodioxane-6-yloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,2,14-trihydroxy-12-[2'-(4"-(naphth-2-yloxy)-3"-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-3,10,16-trione;

17-Ethyl-1-hydroxy-12-[2'-(4"-(4'''-dimethylamino)-phenyloxy-3"-hydrocycyclohexyl)-1'-methylvinly]-23,25-dimethoxy-13,19,21,27-tetramethyl-11,28-dioxa-4-azatricyclo[22.3.1.0$^{4,9}$]-octacos-18-ene-2,3,10,16-tetraone;

17-Ethyl-1-hydroxy-12-[2'-(4"-hydroxy-3"-(4''''-dimethylamino)phenyloxcyclohexyl)-1'-methylvinyl]-23,25-dimethoxy-13,19,21,27-tetramethyl-11,28-dioxa-4-azatricyclo[22.3.1.04,9]-octacos-18-ene-2,3,10,16-tetraone;

17-Ethyl-1,14-dihydroxy-12-[2'-(4"-allyloxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4"-(2''''-butynyloxy)-3'''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4"-cinnamyloxy-3"-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone;

17-Ethyl-1,14-dihydroxy-12-[2'-(3"-methoxy-4"-phenylpropyloxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone;

17-Ethyl-1,14-dihydroxy-12-[2'-(4'''-allyloxy-3''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(3''-allyloxy-4''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(3''-hydroxy-4''-iropropyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4''-hydroxy-3''-isopropyloxycyclohexyl)-1'-methylvinly]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4''-sec-butenyloxy-3''--hydrocyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(3''-sec-butenyloxy-4''-hydroxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone;

17-Ethyl-1,14-dihydroxy-12-[2'-(4''-(trans-2'''-butenyloxy)-3''-hydroxycyclohexyl)-1'-methylvinyl]-23,25-dimethoxy-13,19,21,27-tetramethyl-11,28-dioxa-4-azatricyclo[22.3.1.0$^{4,9}$]ocacos-18-ene-2,3,10,16-tetraone;

17-Ethyl-1,14-dihydroxy-12-[2'-(3''-(trans-2'''-butenyloxy)-4''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(3''-hydroxy-4''-(3'''-methyl-2-butenyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4''-hydroxy-3''-(3'''-methyl-2-butenyloxycyclohexyl)-1'-methylvinly]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(3''-hydroxy-4''-(2'''-methylpropenyloxycyclohexyl)-1'-methylvinyl]-23,25-dimethoxy-13,19,21,27-tetramethyl-11,28-dioxa-4-azatricyclo]22.3.1.0$^{4,9}$]octacos-18-ene-2,3,10,16-tetraone;

17-Ethyl-1,14-dihydroxy-12-[2'-(4''-hydroxy-3''-(2'''-methylpropenyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4''-cinnamyloxy-3''-hydroxycyclohexyl)-1'-methylvinyl]-23,25-dimethoxy-13,19,21,27-tetramethyl-11,28-dioxa-4-azatricyclo-[22.3.1.0$^{4,9}$]octacos-18- ene-2,3,10,16-tetraone;

17-Ethyl-1,14-hydroxy-12-[2'-(3''-cinnamyloxy-4''-hydroxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone;

17-Ethyl-1-hydroxy-12-[2'-(4''-sec-butenyloxy-3''-hydroxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone;

17-Ethyl-1-hydroxy-12-[2'-(3''-sec-butenyloxy-4''-hydroxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone;

17-Ethyl-1-hydroxy-12-[2'-(4''-cinnamyloxy-3''-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone;

17-Ethyl-1-hydroxy-12-[2'-(3''-methoxy-4''-phenylpropyloxycyclohexyl)-1'-methylvinly]-23,25-dimethoxy-13,19,21,27-tetramethyl-11,28-dioxa-4-azatricyclo-[22.3.1.0$^{4,9}$]octacos-18-ene-2,3,10,16-tetraone;

17-Ethyl-1,14-dihydroxy-12-[2'-(4''-(4'''-methoxyphenyloxy)-3''-methoxycyclohexyl)-1'-methylvinyl]-23,25-dimethoxy-13,19,21,27-tetramethyl-11,28-dioxa-4-aza-tricyclo[22.3.1.0$^{4,9}$]octacos-18-ene-2,3,10,16-tetraone;

17-Ethyl-1,14-dihydroxy-12-[2'-(4''-(3'4''-methoxyphenyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4''-(6'''-hydroxynaphth-2-yloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4''-(4'''-hydroxyphenyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4''-(4'''-methylthiophenyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4''-(2'''-methylphenyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4''-(3-'''-methylphenyloxy)-3''-methoxycyclohexyl)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4''-(3''', 4'''-dimethylphenyloxy)-3''-methoxycyclohexyl-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1-hydroxy-12-[2'-(4''-allyloxy-3''-methoxycyclohexyl)-1'-methylvinyl]-23,25-dimethoxy-13,19,-21,27-tetramethyl-11,28-dioxa-4-azatricyclo-[22.3.1.0$^{4,9}$]octacos-18-ene-2,3,10,16-tetraone;

17-Ethyl-1-hydroxy-12-[2'-(4''-(2'''-butynyloxy)-3'-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone;

17-Ethyl-1-hydroxy-12-[2'-(4''-cinnamyloxy)-3''-methoxycyclohexyl)-1'-methylvinyl]-23,25-dimethoxy- 13,19,21,27-tetramethyl-11,28-dioxa-4-azatricyclo-[22.3.1.0⁴,⁹]octacos-18-ene-2,3,10,16-tetraone;

17-Ethyl-1-hydroxy-12-[2'-(3''-methoxy-4''-phenylpropyloxycyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-Ethyl-1-hydroxy-12-[2'-(4''-allyoxy-3''-hydroxycyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-Ethyl-1-hydroxy-12-[2'-(3''-allyoxy-4''hydroxycyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-Ethyl-1-hydroxy-12-[2'-(3''-hydroxy-4''-isopropyloxycyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-Ethyl-1-hydroxy-12-[2'-(4''-hydroxy-3''-isopropyloxycyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-Ethyl-1-hydroxy-12-[2'-(4''-trans-2'''-butynyloxy)-3''-hydroxycyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-Ethyl-1-hydroxy-12-[2'-(3''-(trans-2'''-butenyloxy)-4''-hydroxycyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-Ethyl-1-hydroxy-12-[2'-(3''-hydroxy-4''-(3'''methyl-2-butenyloxycyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-Ethyl-1-hydroxy-12-[2'-(4''-hydroxy-3'''-(3'''-methyl-2-butenyloxycyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-Ethyl-1-hydroxy-12-[2'-(3''-hydroxy-4''-methylpropenyloxycyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-Ethyl-1-hydroxy-12-[2'-(4''-hydroxy-3''-(2'''-methylpropenyloxycyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-Ethyl-1-hydroxy-12-[2'-(3''-cinnamyloxy-4''-hydroxycyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-Ethyl-1,14-dihydroxy-12-[2'-(4''-sec-p henethyloxy-3''-methoxycyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-Ethyl-1,14-dihydroxy-12-[2'-(4''-(2'''-methylcinnamyloxy)-3''-methoxycyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-Ethyl-1,14-dihydroxy-12-[2'-(4''-(4'''-methyl-2''',4'''-hexadienyloxy)-3''-methoxycyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-Ethyl-1,14-dihydroxy-12-[2'-(4''-(p-methoxycinnamyloxy)-3''-methoxycyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-Ethyl-1,14-dihydroxy-12-[2'-(4''-(3''',4'''-methylene-dioxycinnamyloxy)-3''-methoxycyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-Ethyl-1,14-dihydroxy-12-[2'-(4''-(4''',4'''-dimethyl-2'''-trans-pentenyloxy)-3''methoxycyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-Ethyl-1,14-dihydroxy-12-[2'(4''-(3'''cyclohexyl2'''-trans-propenyloxy)-3''-methoxycyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-Ethyl-1,14-dihydroxy-12-[2'-(4''-p-fluoro cinnamyloxy-3''-methoxycyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-Ethyl-1,14-dihydroxy-12-[2'-(4''-p-chloro cinnamyloxy-3''-methoxycyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-Ethyl-1,14-dihydroxy-12-[2'-(4''-p-bromocinnamyloxy-3''methoxycyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-Ethyl-1,14-dihydroxy-12-[2'-(3''-methoxy-4''-p-fluorophenylpropyloxycyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-Ethyl-1-hydroxy-12-[2'-(3'',4''-diallyoxycyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17Ethyl-1-hydroxy-12-[2'-(3'',4''-dipropyloxycyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-Ethyl-1,14-dihydroxy-12-[2'-(4''-(2'''-benzylamino)-ethoxy-3''-methoxycyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-Ethyl-1-hydroxy-12-[2'-(4''-(2'''-benzylamino)ethoxy-3''-methoxycyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-Ethyl-1,14-dihydroxy-12-[2'-(4''-(2'''-benzyloxyethoxy)-3''-methoxycyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-Ethyl-1,14-dihydroxy-12-[2'-(4"-benzyloxymethoxy-3"-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone;

17Ethyl-1,14-dihydroxy-12-[2'-(4"-(napth-2-yloxy)-3"-allyloxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone;

17-Ethyl-1,14-dihydroxy-12-[2'-(4"-(ethoxycarbomethoxy)-3"-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone;

17-Ethyl-1,14-dihydroxy-12-[2'-(4"-(p-hydroxycinnamyloxy)-3"-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone;

17-Ethyl-1-hydroxy-12-[2'-(4"-(p-hydroxycinnamyloxy)-3"-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone;

17-Ethyl-1,14-dihydroxy-12-[2'-(4"-(2'''-phenyl-2'''-oxo-ethyloxy)-3"-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone;

17-Ethyl-1-hydroxy-12-[2'-(4"-(2'''-phenyl-2'''-oxoethyloxy)-3"-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone;

17Ethyl-1,14-dihydroxy-12-[2'-(4"-(2'''-phenyl-2'''-oxo-ethyloxy)-3"-hydroxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone;

17-Ethyl-1,14-dihydroxy-12-[2'-(4"(2'''-(3''''-methoxyphenyl)-2'''-oxo-ethyloxy)-3"-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone;

17-Ethyl-1-hydroxy-12-[2'-(4"-(2'''-(3''''-methoxyphenyl)-2'''-oxo-ethyloxy)-3"-methoxycyclohexyl-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone;

17-Ethyl-1,14-dihydroxy-12-[2'-(4"-(2'''-(3''''-methoxyphenyl)-2'''-oxo-ethyloxy)-3"-hydroxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone;

17-Ethyl-1,14-dihydroxy-12-[2'-(4"-(2'''-(4''''-methoxyphenyl)-2'''-oxo-ethyloxy)-3"-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone;

17-Ethyl-1-hydroxy-12-[2'(4"-(2'''-(4''''-methoxyphenyl)-2'''-oxo-ethyloxy)-3"-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone;

17-Ethyl-1,14-dihydroxy-12-[2'-(4"-(2'''-(4''''-methoxyphenyl)-2'''-oxo-ethyloxy)-3"-hydroxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone;

17-Ethyl-1,14-dihydroxy-12-[2'-(4"-(2'''-(3'''',5''''-dimethoxyphenyl)-2'''-oxo-ethyloxy)-3"-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone;

17-Ethyl-1-hydroxy-12-[2'-(4"-(2'''-(3'''',5''''-dimethoxyphenyl)-2'''-oxo-ethyloxy)-3"-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone;

17-Ethyl-1,14-dihydroxy-12-[2'-(4"-(2'''-(3'''',5''''-dimethoxyphenyl)-2'''-oxo-ethyloxy)-3"-hydroxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone;

17-Ethyl-1,14-dihydroxy-12-[2'-(4"(2'''-(3'''',5''''-difluorophenyl)-2'''-oxo-ethyloxy)-3"methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone;

17-Ethyl-1-hydroxy-12-[2'-(4"-(2'''-(3'''',5''''-didifluorophenyl-2'''-oxo-ethyloxy)-3"-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone;

17-Ethyl-1,14-dihydroxy-12-[2'-(4"-(2'''-(3'''',5''''-difluorophenyl)-2'''-oxo-ethyloxy)-3"-hydroxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone;

17-Ethyl-1,14-dihydroxy-12-[2'-(4"-(2'''-(4''''-hydroxyphenyl)-2'''-oxo-ethyloxy)-3"-methoxycyclohexyl-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone;

17-Ethyl-1-hydroxy-12-[2'-(4"-(2'''-(4''''-hydroxyphenyl)-2'''-oxo-ethyloxy)-3"-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone;

17-Ethyl-1,14-dihydroxy-12-[2'-(4"-(2'''-(4''''-hydroxyphenyl)-2'''-oxo-ethyloxy)3"-hydroxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone;

17-Ethyl-1,14-dihydroxy-12-[2'-(4"-(2'''-phenyl-2'''-hydroxyethyloxy)-3"-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone;

17-Ethyl-1-hydroxy-12-[2'-(4"-(2'''-phenyl-2'''-hydroxyethyloxy)-3"-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone;

17-Ethyl-1,14-dihydroxy-12-[2'--(4"-(2'''-phenyl-2'''-hydroxyethyloxy)-3"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4"-(2'''-(3''''-methoxyphenyl)-2'''-hydroxyethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1-hydroxy-12-[2'-(4''-(2'''-(3''''-methoxyphenyl)-2'''-hydroxyethyloxy)-3''-methoxycyclohexyl)-1'-methylvinyl]-23,25-dimethoxy-13,19,21,27-tetramethyl-11,28-dioxa4-azatricyclo-[22.3.1.0$^{4,9}$]octacos-18-ene-2,3,10,16-tetraone;

17-Ethyl-1,14-dihydroxy-12-[2'-(4''-(2'''-(3''''-methoxyphenyl)-2'''-hydroxyethyloxy)-3''-hydroxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone;

17-Ethyl-1,14-dihydroxy-12-[2'-(4''-(2'''-(3'''',5''''-dimethoxyphenyl)-2'''-hydroxyethyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1-hydroxy-12-[2'-(4''-(2'''-(3'''',5''''-dimethoxyphenyl)-2'''-hydroxyethyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4''-(2'''-(3'''',5''''-dimethoxyphenyl)-2'''-hydroxyethyloxy)-3''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4''-(2'''-(3'''',5''''-difluorophenyl)-2'''-hydroxyethyloxy)-3''-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone;

17-Ethyl-1-hydroxy-12-[2'-(4''-(2'''-(3'''',5''''-difluorophenyl-2'''-hydroxyethyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4''-(2'''-(3'''',5''''-difluorophenyl)-2'''-hydroxyethyloxy)-3''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4''-(2'''-(4''''-hydroxyphenyl)-2'''-hydroxyethyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1-hydroxy-12-[2'-(4''-(2'''-(4''''-hydroxyphenyl)-2'''-hydroxyethyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4''-(2'''-(4''''-hydroxyphenyl)-2'''-hydroxyethyloxy)-3''-hydroxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone;

17-Ethyl-1,14-dihydroxy-12-[2'-(4''-(m-fluorocinnamyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4''-(3''',5'''-difluorocinnamyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4''-(m-nitrocinnamyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12--[2'-(4''-(3'''-phenyl-2'''-propynyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12--[2'-(4''-(2'''-phenyl-2'''-propenyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4''-(p-hydroxycinnamyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4''-(p-hydroxyphenpropyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4''-(m-hydroxycinnamyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4''-(m-hydroxymethylbenzyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4''-(m-hydroxycinnamyloxy)-3''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4''-(3''',5'''-difluorocinnamyloxy)-3''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4''-(p-carboxybenzyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4''-(m-carboxybenzyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4''-(m-carbomethoxybenzyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4''-(m-isopropylcarboxamidobenzyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4''-(m-butylcarboxamidobenzyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4"-acetamidoxy-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4"-carboxymethoxy-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4"-(N-phenylacetamidoxy-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4"-(N-benzylacetamidoxy-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1-hydroxy-12-[2'-(4"-carboxymethyoxy-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1-hydroxy-12-[2'-(4"-(N-benzylamidoxymethyoxy-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1-hydroxy-12-[2'-(4"-(N-methyltyrosine)amidoxy-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4"-(2'''-(m-methylphenyl)-2'''-oxo-ethyloxy)-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4"-(2'''-(p-methylphenyl)-2'''-oxo-ethyloxy)-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4"-(2'''-phenyl-2'''-hydroxyethyloxy)-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4"-(2'''-(m-methylphenyl)-2'''-hydroxyethyloxy)-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4"-(2'''-(m-ethylphenyl)-2'''-oxo-ethyloxy)-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4"-(2'''-phenylethyloxy)-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4"-(2'''-phenyl-2'''-acetoxyethyloxy)-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4"-(2'''-morpholinoethyloxy)-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4"-(naphth-2-ylmethyloxy)-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12--[2'-(4"-(4''',5'''-methylenedioxybenzyloxy)-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4"-(4'''-N,N,-dimethylaminophenyloxy)-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4"-(3'''-fluorophenyloxy)-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'--(4"-(3'''-(2''''-dioxolanylphenyloxy)-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4"-(3'''-formylphenyloxy)-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4"-(3'''-carboxyphenyloxy)-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4"-(3''',4'''-dimethoxyphenyloxy)-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4"-(4'''-trifluoromethylphenyloxy)-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4"-(3''',5'''-bis-(trifluoromethyl)phenyloxy)-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1-hydroxy-12-[2'-(4"-(4'''-methylphenyloxy)-3"-hydroxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1-hydroxy-12-[2'-(4"-hydroxy-3"-(4''''-methylphenyloxy)cyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1-hydroxy-12-[2'-(4"-(4''''-hydroxyphenyloxy)-3"-hydroxycyclohexyl)-1'-methylvinyl]-23,25-dimethoxy-13,19,21,27-tetramethyl- 11,28-dioxa-4-azatricyclo[22.3.1.0^{4,9}]octacos-18-ene-2,3,10,16-tetraone;

17-Ethyl-1-hydroxy-12-[2'-(4''-hydroxy-3''-(4'''-hydroxyphenyloxy)cyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Ethyl-1-hydroxy-12-[2'-(4''-(4'''-hydroxymethylphenyloxy)-3''-hydroxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone and;

17-Ethyl-1-hydroxy-12-[2'-(4''-hydroxy-3''-(4'''-hydroxymethylphenyloxy)cyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Ethyl-1-hydroxy-12-[2'-(4''-hydroxy-3''-(4'''-formylphenyloxy)cyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Ethyl-1-hydroxy-12-[2'-(4''-(4'''-N,N-dimethylaminophenyloxy)-3''-hydroxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Ethyl-1-hydroxy-12-[2'-(4''-hydroxy-3''-(4'''-N,N-dimethylaminophenyloxy)cyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Ethyl-1-hydroxy-12-[2'-(4''-phenyloxy)-3''-hydroxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Ethyl-1-hydroxy-12-[2'-(4''-hydroxy-3''-phenyloxy)cyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Ethyl-1-hydroxy-12-[2'-(4''-(4'''-methoxyphenyloxy)-3''-hydroxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone and;

17-Ethyl-1-hydroxy-12-[2'-(4''-hydroxy-3''-(4'''-methoxyphenyloxy)cyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Ethyl-1-hydroxy-12-[2'-(4''-(3'''-methoxyphenyloxy)-3''-hydroxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone; and 17-Ethyl-1-hydroxy-12-[2'-(4''-hydroxy-3''-(3'''-methoxyphenyloxy)cyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone.

B. Preparation of Compounds Within the Scope of the Present Invention

The starting materials for the preparation of the compounds of this invention are represented by Formula II:

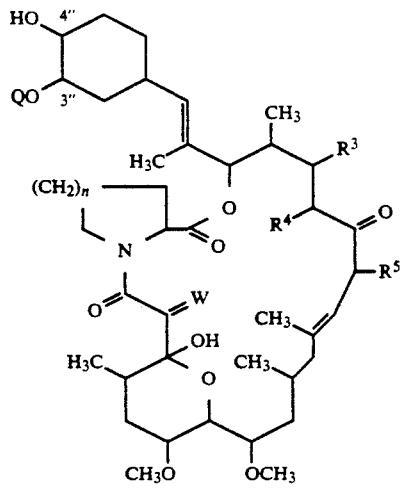

wherein:
Q is hydrogen or methyl;
W is O or (H, OH);
$R^3$ is hydrogen, hydroxy, or $C_1$-$C_6$ alkoxy;
$R^4$ is hydrogen, or $R^3$ and $R^4$ taken together form a double bond;
$R^5$ is methyl, ethyl, propyl or allyl; and
n is 1 or 2.

The production and characterization of compounds of Formula II is well known in the literature (see U.S. Pat. No. 4,894,366 issued Jan. 16, 1990; U.S. Pat. No. 4,929,611 issued May 29, 1990; U.S. Pat. No. 3,244,592 issued Apr. 15, 1966; EPO Publication No. 0,323,042; EPO Publication No. 0,356,399; PBJ Disclosure 63-17884; J. Am. Chem. Soc., 1987, 109, 5031; and J. Antibiotics, 1987, 40, 1249). Both biological fermentation and synthetic processes may be found. A synthetic route to compounds of Formula II can involve modifications of a route described in J. Am. Chem. Soc. 1989, 111, 1157.

Biological fermentation followed by synthetic modification is presently favored in the art as the method to produce compounds of Formula II. Organisms belonging to the genus Streptomyces such as Streptomyces tsukubaensis, No. 9993 and Streptomyces hygroscopicus, No. 7238 placed in an aqueous nutrient medium will produce desired compounds in isolable amounts. The nutrient medium contains sources of assimilable carbon and nitrogen, preferably under aerobic conditions. Produced in fermentation are four compounds of Formula II, (A) where Q is methyl, W is O, $R^3$ is hydroxyl, $R^4$ is hydrogen, $R^5$ is allyl and n is 2; (B) where Q is methyl, W is O, $R^3$ is hydroxyl, $R^4$ is hydrogen, $R^5$ is ethyl and n is 2; (C) where Q is methyl, W is O, $R^3$ is hydroxyl, $R^4$ is hydrogen, $R^5$ is methyl and n is 2; and (D) where Q is methyl W is O, $R^3$ is hydroxyl, $R^4$ is hydrogen, $R^5$ is allyl and n is 1.

A lyophilized sample of the isolated Streptomyces tsukubaensis, No. 9993 was deposited with the Fermentation Research Institute, Agency of Industrial Science and Technology (No. 1-3, Higashi 1-chome, Yatabemachi Tsukuba-gun, Ibaraki Prefecture, Japan) under the deposit number of FERM P-7886 (deposit date: Oct. 5th, 1984), and then converted to Budapest Treaty route of the same depository on Oct. 19, 1985 under the new deposit number of FERM BP-927.

Using the four compounds produced in fermentation above, the remaining compounds of Formula II may be easily produced. The allyl of $R^5$ may be conveniently reduced to propyl by well known methods, for example as described in U.S. Pat. No. 4,894,366. The hydroxy of $R^3$ may be protected by well known methods, for example as disclosed in EPO Publication No. 0,323,042. Likewise, the hydroxy at C-4" may also be protected. In addition, the hydroxy of $R^3$ may be reduced to a hydrogen or eliminated to form a double bond with $R^4$ (by methods disclosed in U.S. Pat. No. 4,894,366 or EPO Publication No. 0,323,042 or EPO Publication No. 0,413,532). The carbonyl of W may be reduced to the alcohol by methods disclosed in EPO Publication No. 0,323,042 or by methods disclosed in U.S. Pat. No. 5,064,835 or in EPO Publication No. 0,445,975.

The methyl of Q as produced may be replaced with hydrogen or demethylated and subsequently protected as desired, if necessary. This demethylation of compounds wherein Q is methyl may be carried out in a fermentation reaction using the compounds of Formula II as a feedstock. For instance, compound A named under Formula II above may be demethylated at Q above by using the microorganism Actinomycetales ATCC No. 53771 (described in U.S. Pat. No. 4,981,792, issued Jan. 1, 1991) or by using the microorganism *Streptomyces tsukubaensis*, No. 9993 (described in EPO Publication No. 0,353,678). Similarly, compound B named under Formula II above may be demethylated at Q above using the microorganism Actinoplanacete sp. ATCC No. 53771 (described in EPO Publication No. 0,349,061). In addition the compound of Formula II wherein Q is H, W is O, $R^3$ is hydroxy, $R^4$ is hydrogen, $R^5$ is ethyl and n is 2 may be produced directly by fermentation using the mutant microorganism *Streptomyces hygroscopicus* sup. *ascomyceticus*, No. 53855 (being a blocked mutant of *Streptomyces hygroscopicus* sup. *ascomyceticus*, No. 14891) (as described in EPO Publication 0,388,152). Similarly, the compound of Formula II wherein Q is hydrogen, W is O, $R^3$ is hydroxy, $R^4$ is hydrogen, $R^5$ is methyl and n is 2 may be produced directly by fermentation using the mutant microorganism *Streptomyces hygroscopicus* sup. *ascomyceticus*, No. 53855 (being a blocked mutant of *Streptomyces hygroscopicus* sup. *ascomyceticus*, No. 14891) (as described in EPO Publication 0,388,153). Also, the compound of Formula II wherein Q is hydrogen, $R^3$ is hydroxy, $R^4$ is hydrogen, $R^5$ is allyl, W is O and n is 2 and the compound of Formula II wherein the C-3" position is oxo (keto), $R^3$ is hydroxy, $R^4$ is hydrogen, $R^5$ is allyl, W is O and n is 2 may be produced directly by fermentation using the microorganism *Streptomyces tsukubaensis*, No. 9993 (described in EPO Publication No. 0,353,678). The hydroxy of C-3" may be protected by methods similar to those known for the protection of the hydroxyl groups of $R^3$ and/or C-4", for example as disclosed in U.S. Pat. No. 4,894,366.

Suitable protecting groups for hydroxyl include those groups well known in the art such as:

1-(lower alkylthio)(lower)alkyl, wherein "lower alkyl" indicates a straight, cyclic or branched chain of one to six carbon atoms, such as lower alkylthiomethyl (e.g. methylthiomethyl, ethylthiomethyl, propylthiomethyl, isopropylthiomethyl, butylthiomethyl, isobutylthiomethyl, hexylthiomethyl, etc.), and the like, in which the preferred one may be $C_1$-$C_4$ alkylthiomethyl and the most preferred one may be methylthiomethyl; trisubstituted silyl such as tri(lower)alkylsilyl (e.g. trimethylsilyl, triethylsilyl, tributysilyl, tri-i-propylsilyl, t-butyldimethylsilyl, tri-i-butylsilyl, etc.), lower alkyldiarylsilyl (e.g. methyl-diphenylsilyl, ethyl-diphenylsilyl, propyl-diphenylsilyl, t-butyldiphenylsilyl, etc.), and the like, in which the preferred one may be tri($C_1$-$C_4$)alkylsilyl and $C_1$-$C_4$ alkyl-diphenylsilyl, and the most preferred one may be tert-butyl-dimethylsilyl, tri-i-propylsilyl and tert-butyl-diphenylsilyl; acyl such as aliphatic acyl, aromatic acyl and aliphatic acyl substituted with aromatic group, which are derived from carboxylic acids; and the like.

Compounds A, B, C and D of Formula II, organisms to produce the same, conditions of fermentation, separation techniques, and chemical modification of the products are fully described in U.S. Pat. No. 4,894,366, issued Jan. 16, 1990 and U.S. Pat. No. 4,929,611, issued May 29, 1990. The novel processes for preparing the novel compounds of the present invention are illustrated as follows, wherein $R^1$, $R^2$, $R^3$, $R^5$, Q, W and n are as defined above unless otherwise indicated. It will be readily apparent to one of ordinary skill in the art reviewing the synthetic route depicted below that other compounds within Formula I can be synthesized by substitution of appropriate reactants and agents in the synthesis shown below.

REACTION SCHEME A

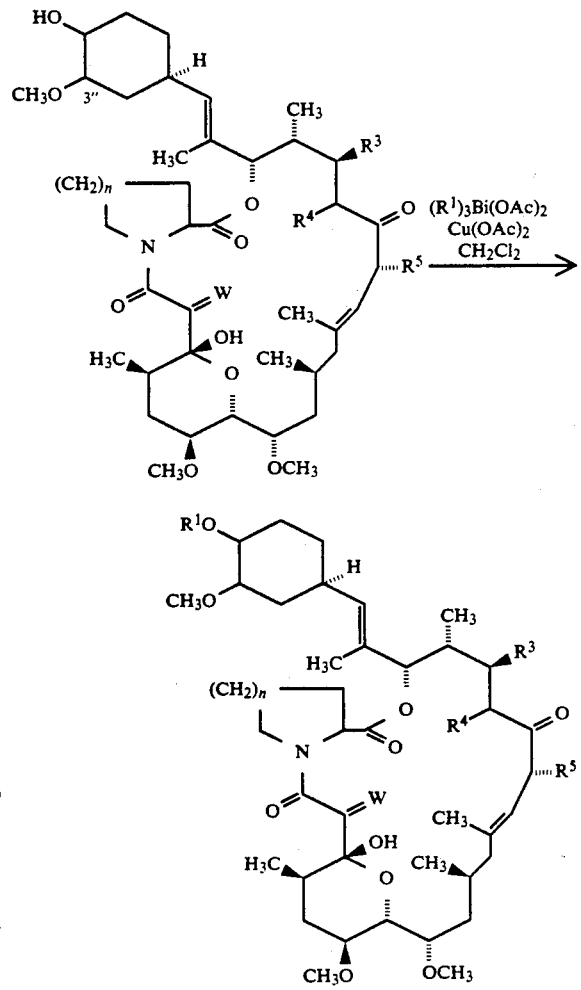

REACTION SCHEME B
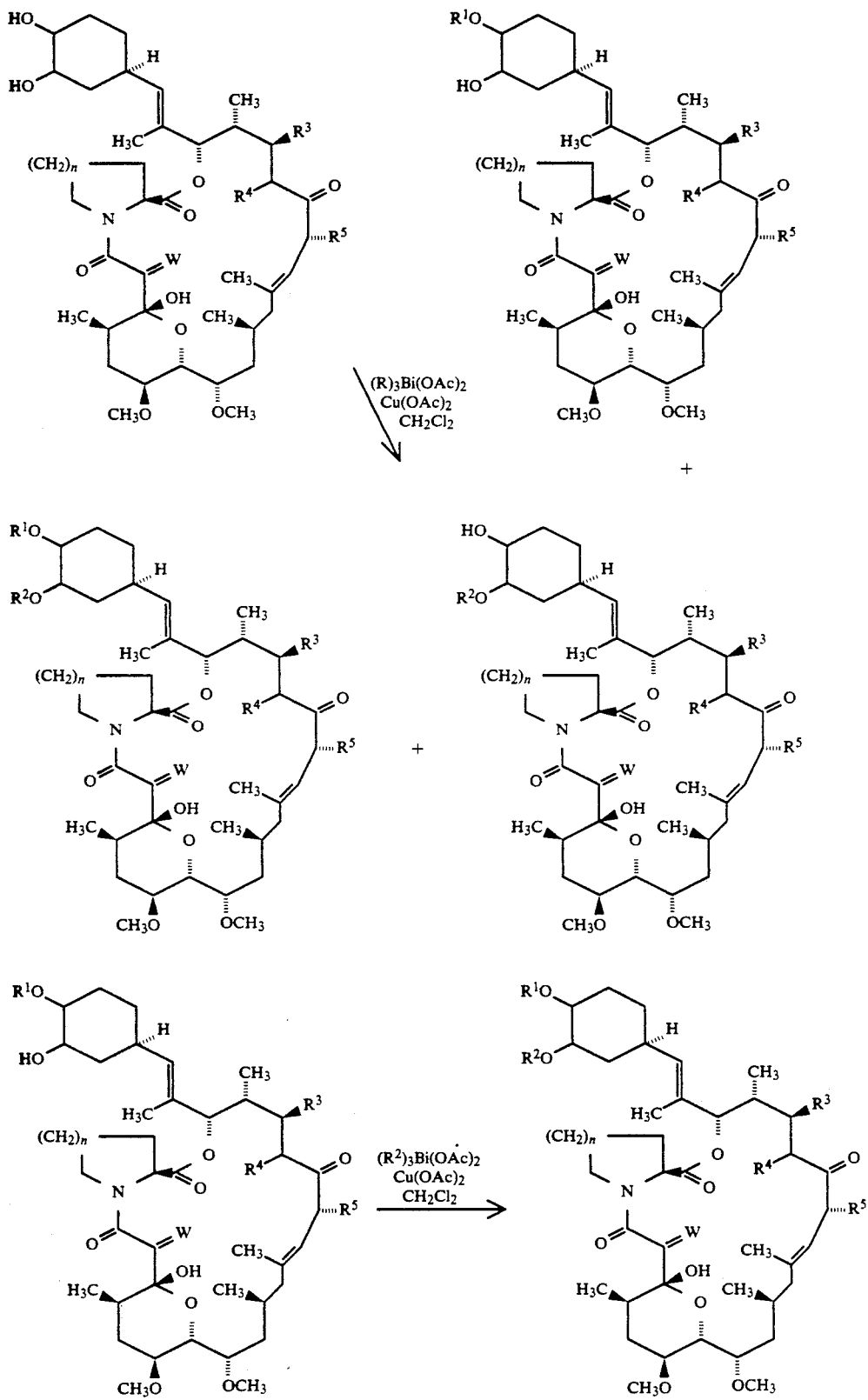

-continued
REACTION SCHEME B
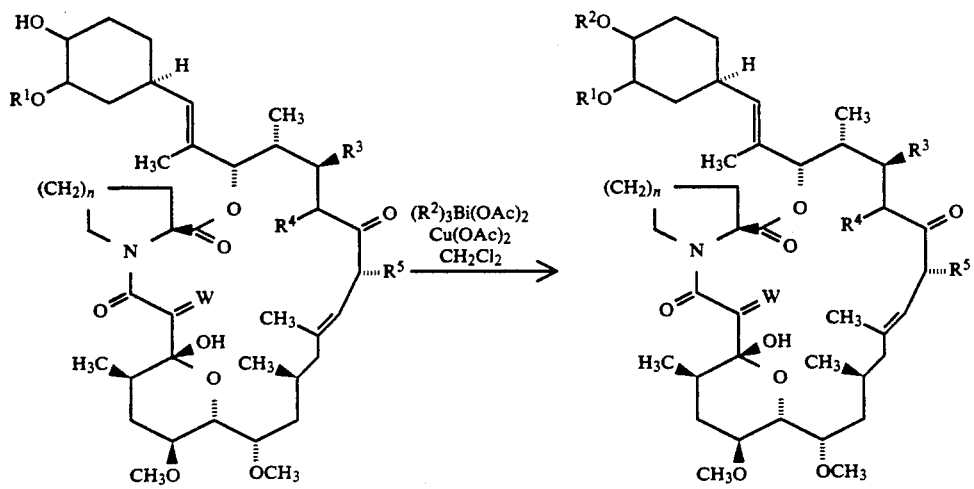
REACTION SCHEME C
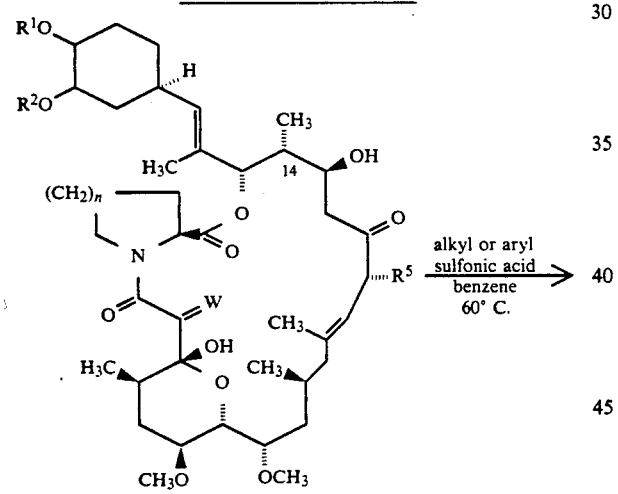
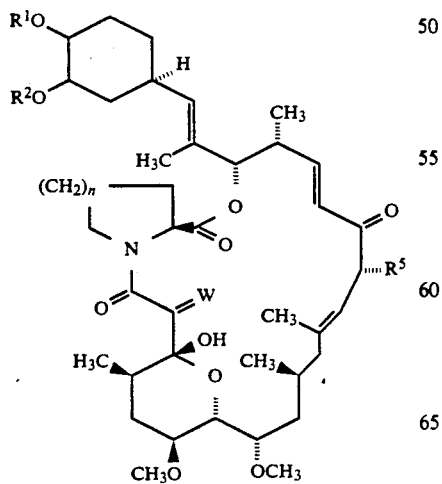
REACTION SCHEME D
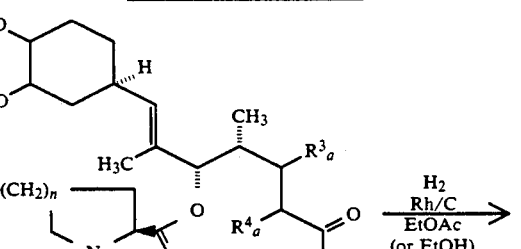
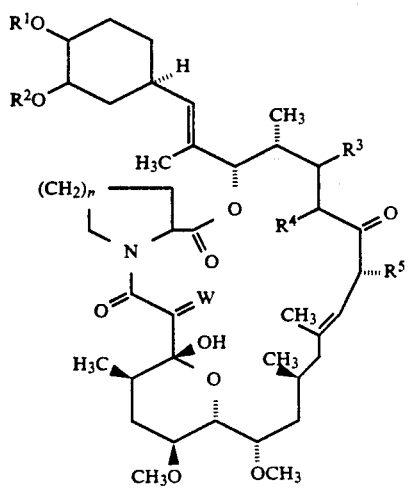

REACTION SCHEME E
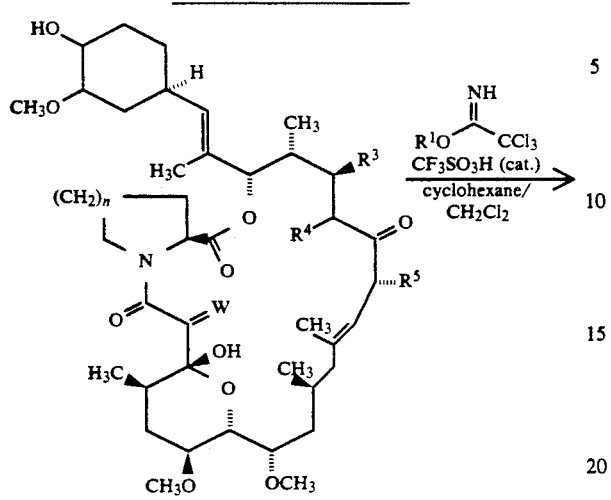
-continued
REACTION SCHEME E
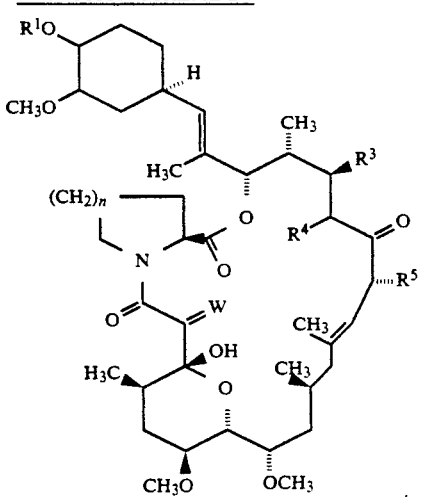
REACTION SCHEME E2
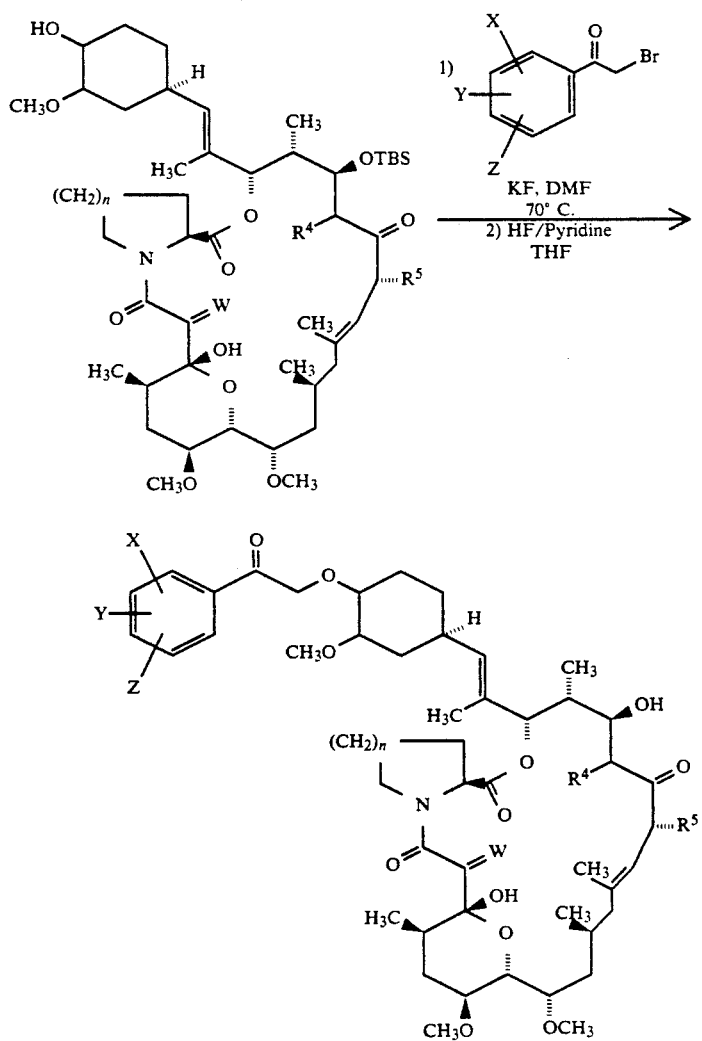

REACTION SCHEME F
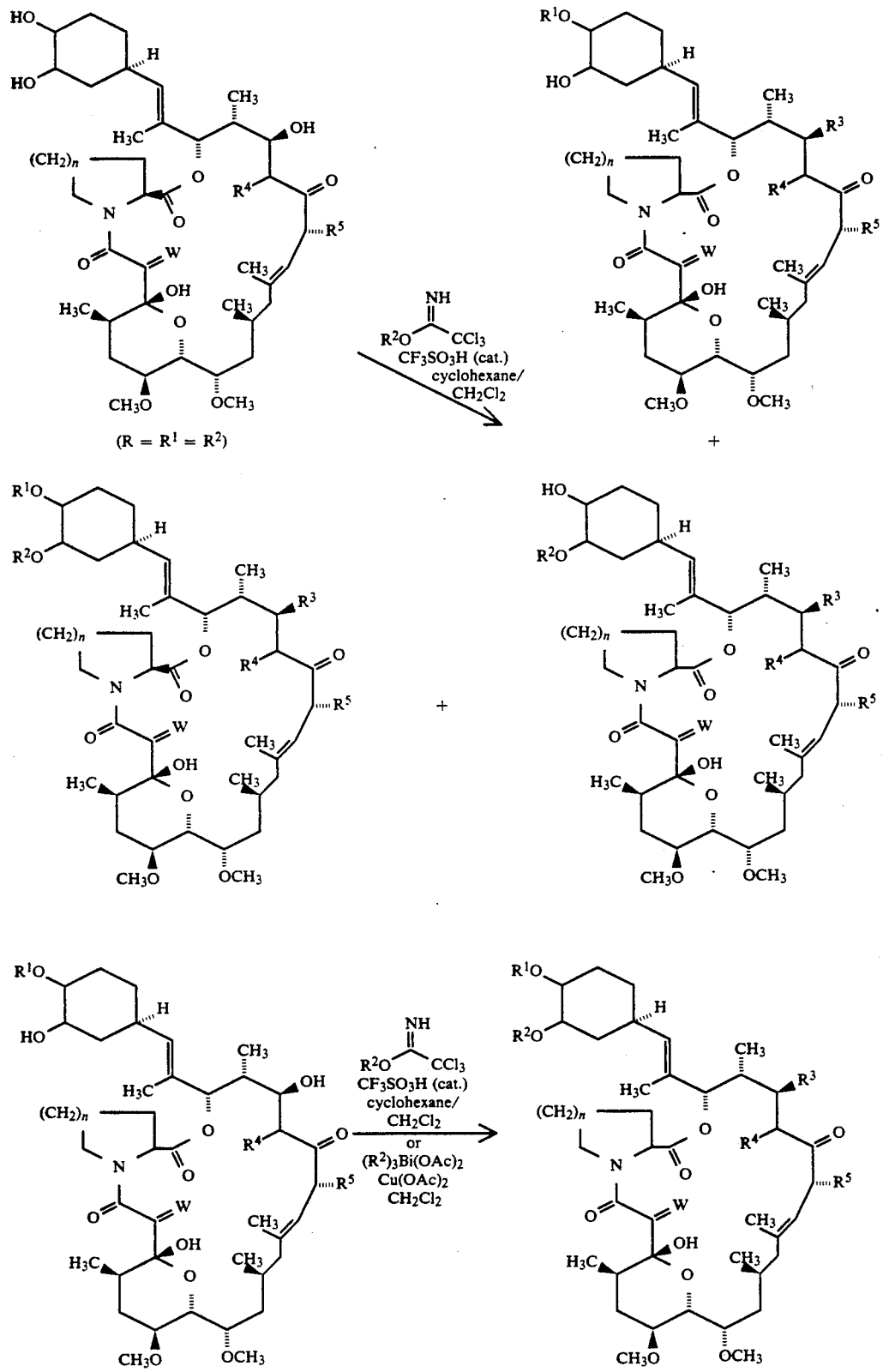

-continued
REACTION SCHEME F
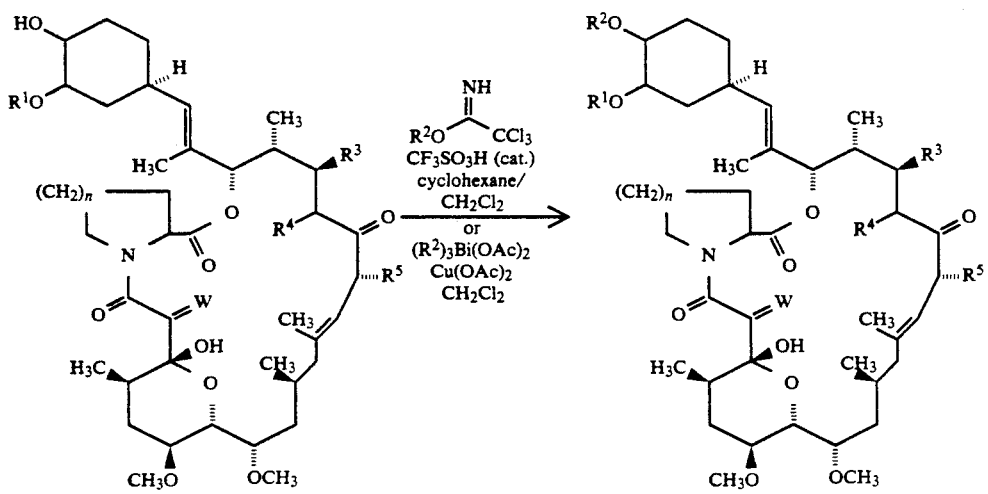
REACTION SCHEME G
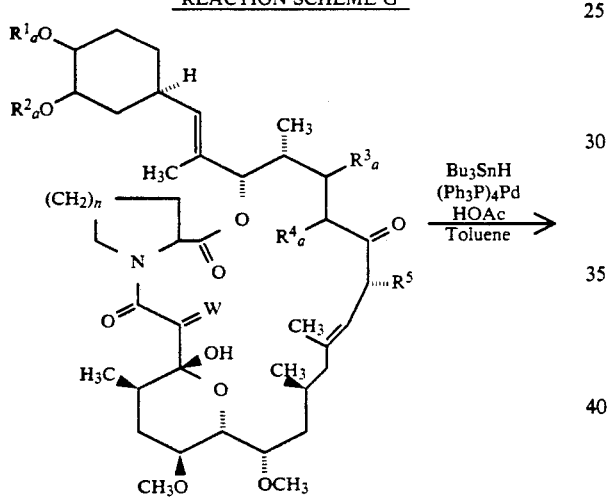
-continued
REACTION SCHEME G
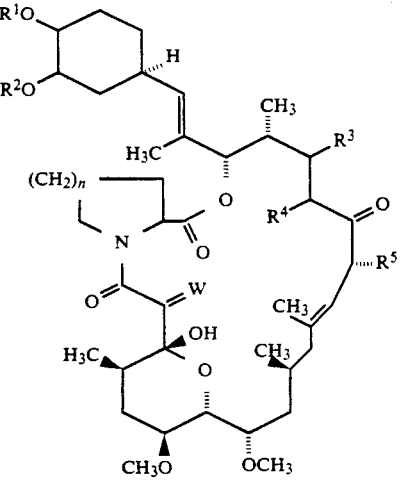
REACTION SCHEME H
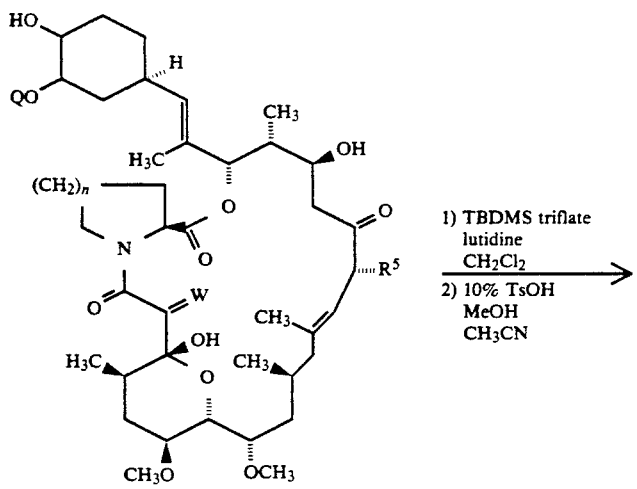
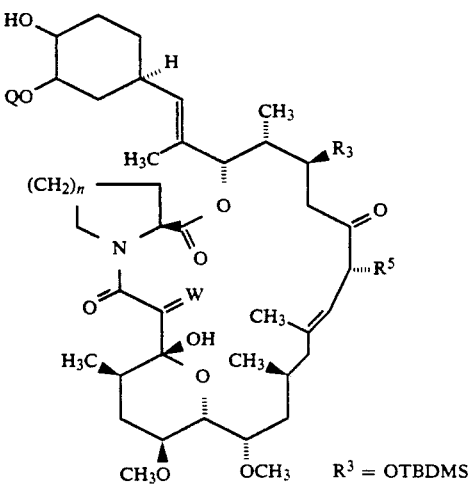

REACTION SCHEME I
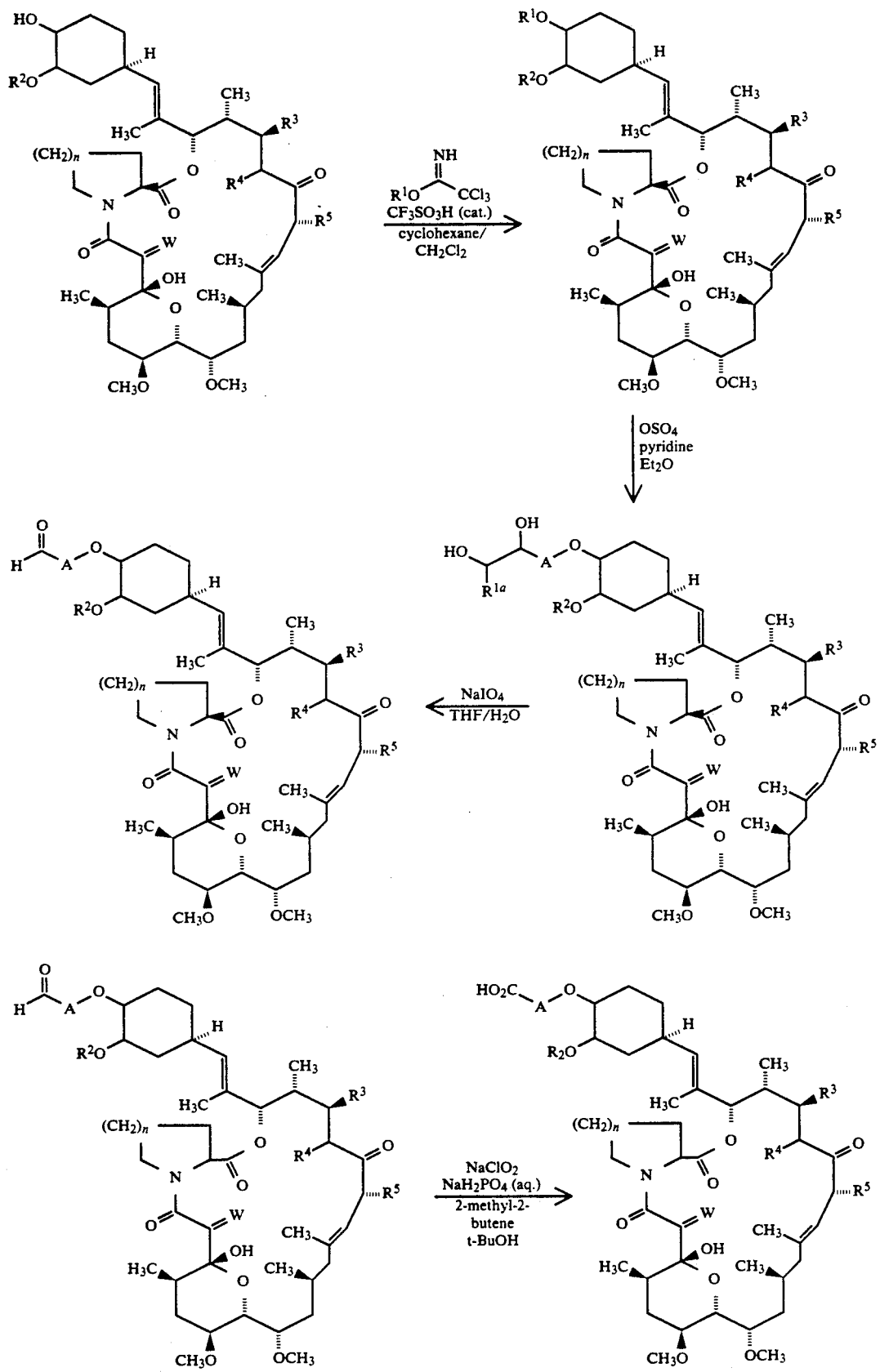

REACTION SCHEME J
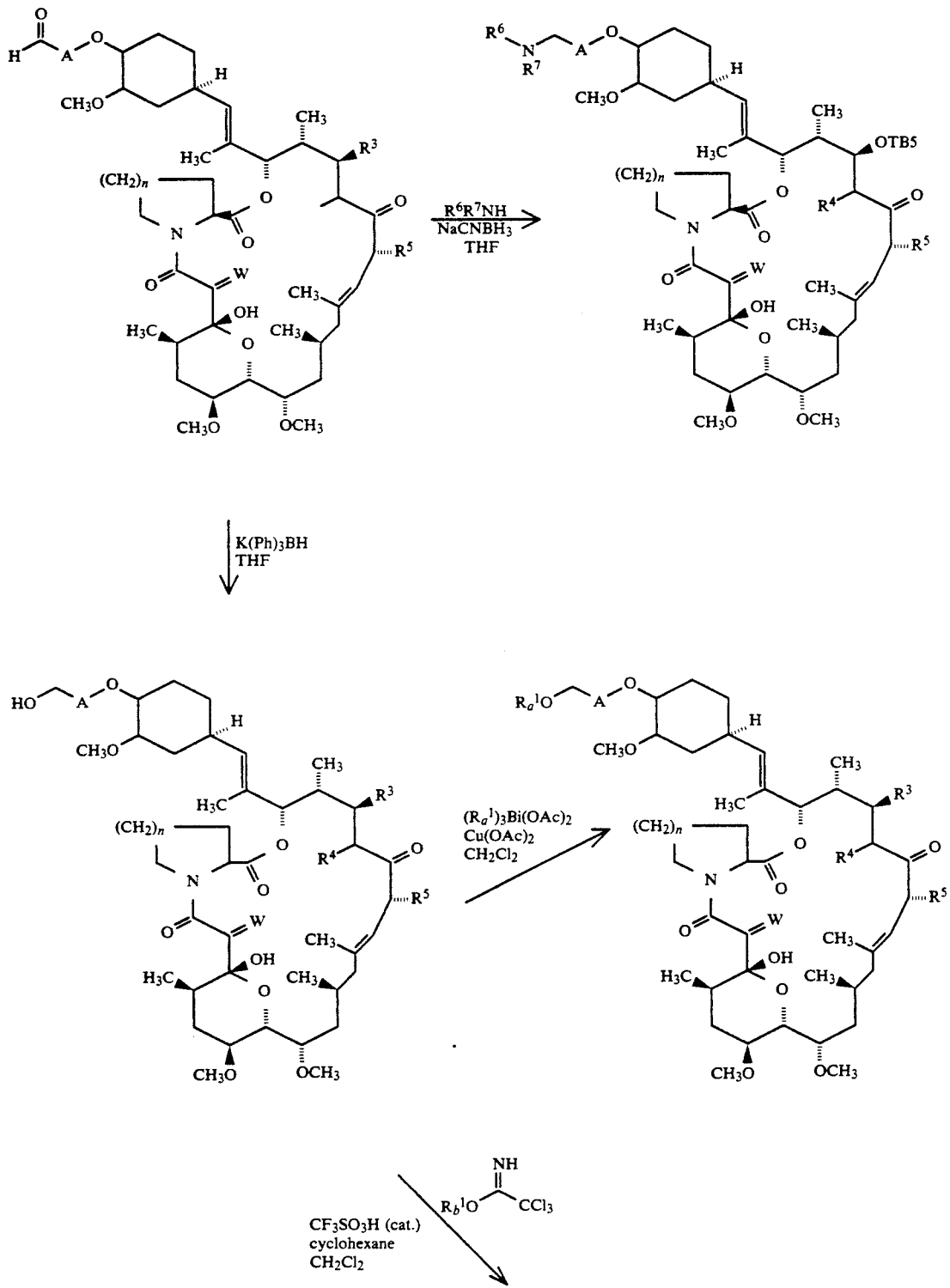

-continued
REACTION SCHEME J
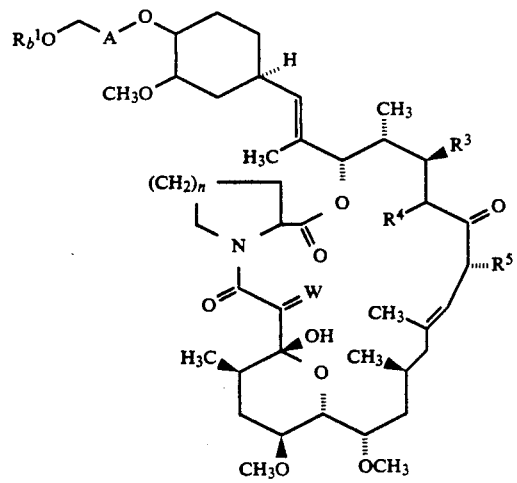
REACTION SCHEME K
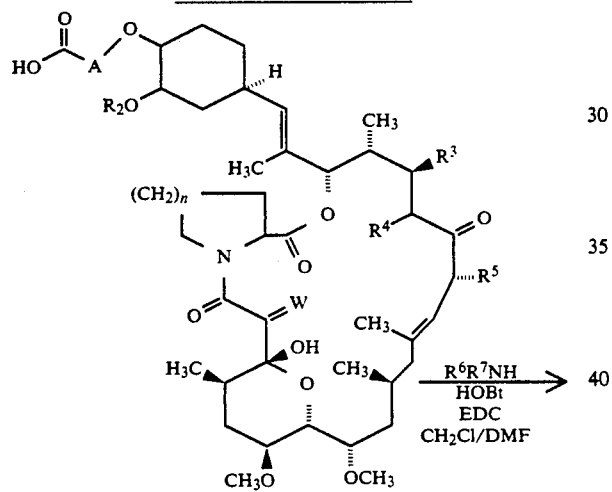
-continued
REACTION SCHEME K
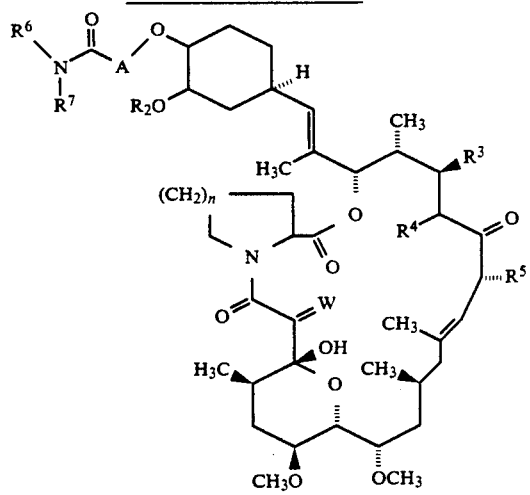
REACTION SCHEME L
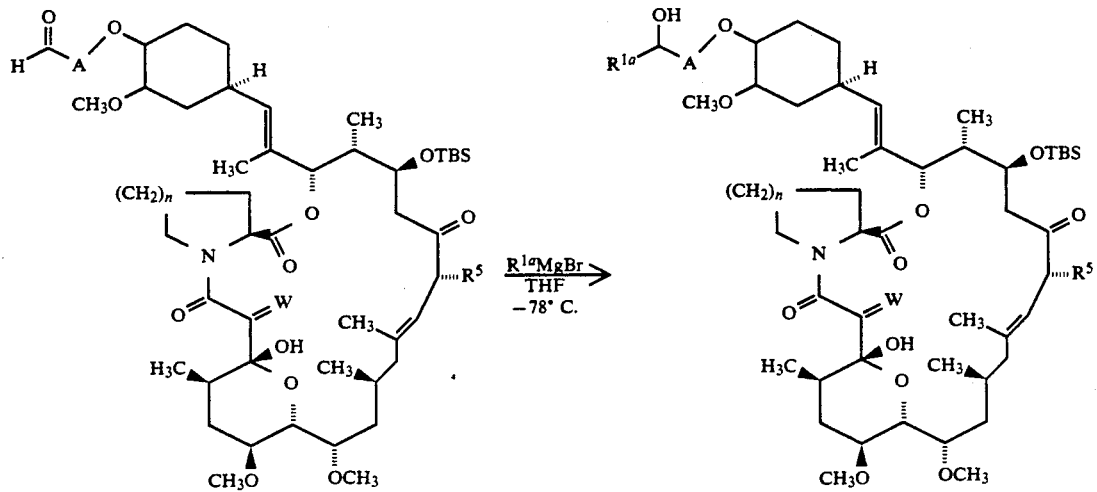

-continued
REACTION SCHEME L
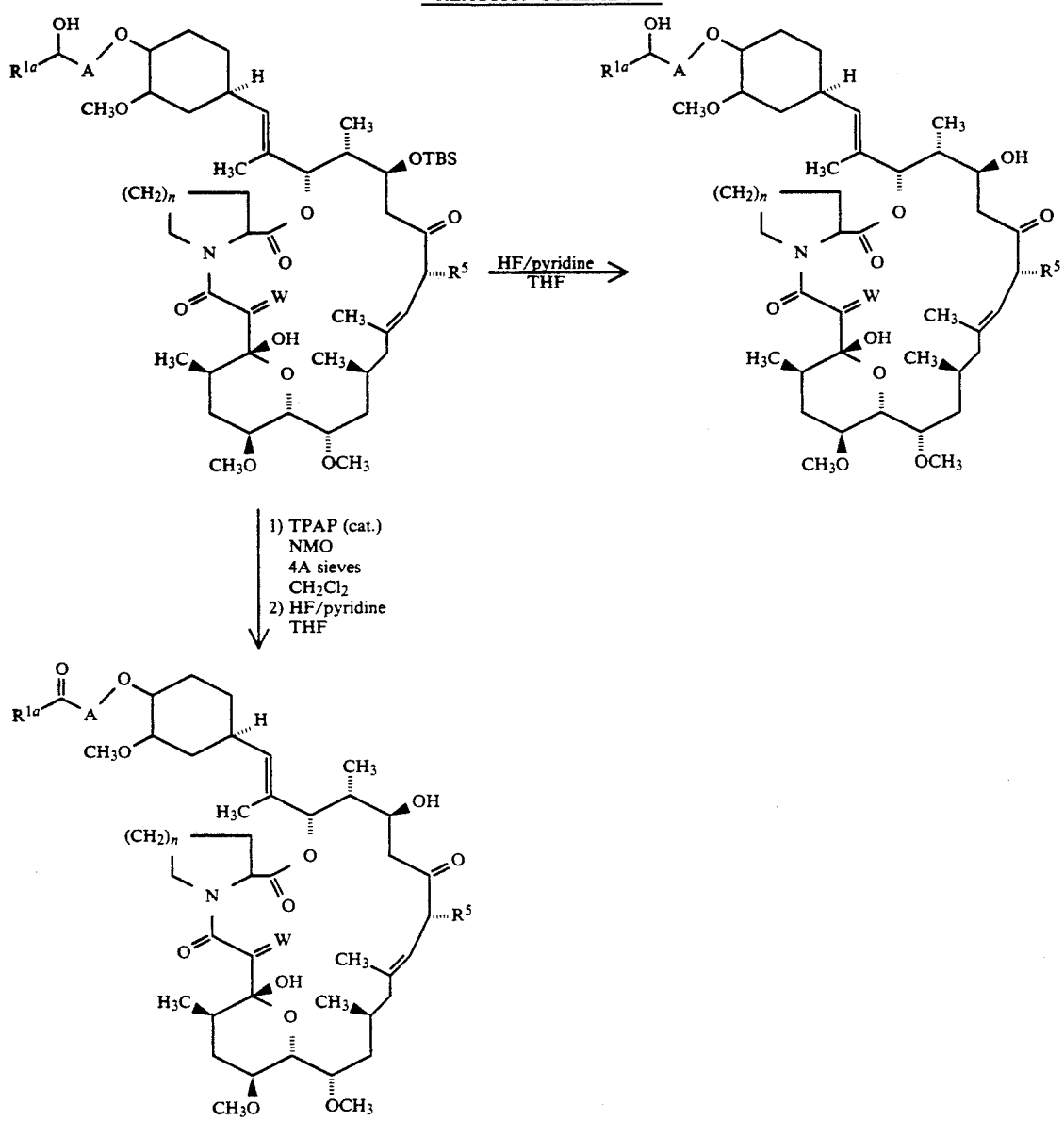

REACTION SCHEME M

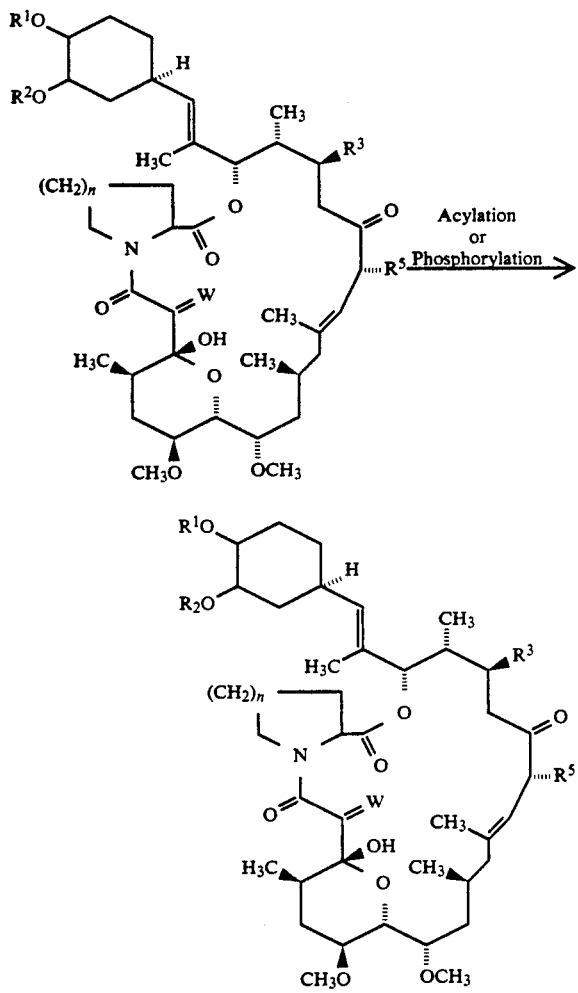

Reaction Scheme A:

As shown in Reaction Scheme A, a solution of a 4''-hydroxy-3''-methoxy macrolide in an inert organic solvent such as methylene chloride, benzene, toluene, chloroform, or the like or mixtures thereof is treated with a triarylbismuth diacetate reagent (wherein $R^1$ is aryl) (prepared immediately prior to use by the addition of acetic acid to a suspension of a triarylbismuth carbonate in an inert organic solvent such as methylene chloride, chloroform or the like or mixture thereof) in the presence of a catalytic amount of copper(II) acetate at a temperature of 20°–50° C., preferably room temperature, for a period of one hour to seven days, preferably one day, to give the 4''-O-aryl-3''-methoxy macrolide. Alternatively, the triarylbismuth(V) reagent can be prepared by treatment of a triarylbismuthine with a suitable oxidant such as peracetic acid, iodobenzene diacetate, bis(trifluoroacetoxy)iodobenzene and the like in an inert solvent such as methylene chloride, chloroform, benzene, toluene and the like. The triarylbismuth(V) reagent can be used without purification or can be purified by silica gel chromatograhy. Triarylbismuthines may be prepared by the reaction of an appropriate aryl Grignard reagent with bismuth trichloride in an inert organic solvent such as tetrahydrofuran, diethyl ether, or 1,4-dioxane, or mixtures thereof, at or near room temperature for a period of 1 to 48 hours. General procedures for the preparation and use of triaryl bismuth reagents may be found in Barton, D. H. E., et al., *J. Chem. Soc. Chem. Commun.*, 1986, 65 and references cited therein.

Reaction Scheme B:

Similarly, as shown in Reaction Scheme B, a solution of the 3'',4''-dihydroxy macrolide is treated with a triarylbismuth diacetate reagent as described in Reaction Scheme A, to give a mixture of the 3''-hydroxy-4''-O-aryl macrolide, the 3''-O-aryl-4''-hydroxy macrolide, and the 3'',4''-di-O-aryl macrolide. At this stage, a solution of 3''-hydroxy-4''-O-aryl macrolide, or 3''-O-aryl-4''-hydroxy macrolide can be treated with a different triarylbismuth diacetate reagent (prepared immediately prior to use by procedures analogous to those disclosed above), to give 3''-O-aryl-4''-O-aryl macrolides.

Reaction Scheme C:

As shown in Reaction Scheme C. the 14-hydroxy group of a macrolide (wherein $R^1$, $R^2$, $R^5$, W and n are as defined above) may be eliminated by treatment with p-toluenesulfonic acid, benzenesulfonic acid, methanesulfonic acid, p-nitrobenzenesulfonic acid, p-bromobenzenesulfonic acid, p-chlorobenzenesulfonic acid, or p-methoxybenzenesulfonic acid, or mixtures thereof, in an inert organic solvent such as benzene, or toluene or the like at a temperature of 40° C. to solvent reflex temperature, preferably 60° C., for about 0.5 to 6 hours, or a sufficient period of time to eliminate the 14-hydroxy group. Neutralization with an aqueous solution of a weak base such as aqueous saturated sodium bicarbonate gives the 14,15-dehydro macrolide. The 14-hydroxy group may also be eliminated by activation followed by basic elimination, as described in U.S. Pat. No. 4,894,366.

Reaction Scheme D:

As shown in Reaction Scheme D the macrolide (wherein $R^1_a$ and/or $R^2_a$ is alkenyl, substituted alkenyl, alkynyl or substituted alkynyl and wherein $R^3_a$ is hydroxy or $C_{1-6}$ alkoxy, $R^4_a$ is hydrogen, or $R^3_a$ and $R^4_a$ taken together form a double bond) is reduced under an atmosphere of hydrogen in the presence of a nobel metal catalyst, such as rhodium on carbon catalyst or rhodium on alumina catalyst, at a pressure of atmospheric pressure to 40 psig, at or near room temperature in an organic solvent such as ethyl acetate or ethanol for about 1 to 24 hours, or until the requisite amount of hydrogen is absorbed to reduce the olefin and give the reduced macrolide.

By changing the sequence of synthetic steps, all possible variations of substitution can be achieved. For example, the C-14 hydroxy group may be elminated and the resultant double bond reduced prior to the introduction of alkenyl or alkynyl substituents at C-3'' and/or C-4''.

Reaction Scheme E:

As shown in Reaction Scheme E, a solution of the 4''-hydroxy 3''-methoxy macrolide in an inert organic solvent such as methylene chloride, chloroform, pentane, hexane, cyclohexane, heptane or the like or mixtures thereof is treated with an alkyl, alkenyl or alkynyl trichloroacetimidate reagent (prepared by the reaction of an appropriate sodium alkoxide with trichloroacetonitrile, such as described by Wessel, H. P., Iversen, T., Bundle, D. R., *J. Chem. Soc., Perkin Trans. I*, 1985, 2247) in the presence of a mild acid catalyst such as trifluoromethanesulfonic acid, p-toluenesulfonic acid, methanesulfonic acid, benzenesulfonic acid, p-nitrobenzenesulfonic acid, p-bromobenzenesulfonic acid, p-chlorobenzenesulfonic acid, or p-methoxybenzenesulfonic acid, or mixtures thereof at a temperature of 20°–50° C. preferably room temperature, for a period of one hour to seven days, preferably one day, to give the 4''-O-alkyl, -alkenyl or -alkynyl 3''-methoxy macrolide.

Reaction Scheme E2:

Alternatively, as shown in Reaction Scheme E2, ketone derivatives can be prepared by direct alkylation of the macrolide by treatment with an unsubstituted or substituted 2-bromoacetophenone in an inert solvent such as N,N-dimethylformamide or tetrahydrofuran and a fluoride source such as potassium fluoride or cesium fluoride at 25°–70° C. for a period of 24–72 hours.

Reaction Scheme F:

Similarly, as shown in Reaction Scheme F, (wherein $R=R^1=R^2$) a solution of the 3'',4''-dihydroxy macrolide in an inert organic solvent such as methylene chloride, chloroform, pentane, hexane, cyclohexane, heptane or the like or mixtures thereof is treated with an alkyl, alkenyl, or alkynyl trichloroacetimidate (prepared by the reaction of an appropriate sodium alkoxide with trichloroacetonitrile, such as described by Wessel, H. P., Inversen, T., Bundle, D. R., *J. Chem. Soc., Perkin Trans. I*, 1985, 2247) in the presence of a mild acid catalyst such as trifluoromethanesulfonic acid, p-toluenesulfonic acid, methanesulfonic acid, benzenesulfonic acid, p-nitrobenzensulfonic acid, p-bromobenzenesulfonic acid, p-chlorobenzenesulfonic acid, or p-methoxybenzenesulfonic acid, or mixtures thereof of at a temperature of 20°–50° C., preferably 40° C., for a period of one hour to seven days, preferably 6 hours, to give a mixture of the 3''-O-alkyl, -alkenyl or -alkynyl 4''-hydroxy macrolide, the 3''-hydroxy 4''-O-alkyl, -alkenyl or -alkynyl macrolide and the 3'',4''-di-O-alkyl, -alkenyl or -alkynyl macrolide.

Reaction Scheme G:

The procedures described in Reaction Schemes C and D may optionally be conducted following the procedures of Reaction Scheme E or F. Alternatively, the procedures described in Reaction Scheme G may be performed. In Reaction Scheme G the macrolide (wherein $R^1_a$ and/or $R^2_a$ is alkenyl, substituted alkenyl, alkynyl or substituted alkynyl and wherein $R^3_a$ is hydroxy or $C_{1-6}$ alkoxy, $R^4_a$ is hydrogen, or $R^3_a$ and $R^4_a$ taken together form a double bond) is reduced with tri-n-butyltin hydride in the presence of tetrakis(triphenylphosphine)palladium(O) catalyst and acetic acid in an organic solvent such as toluene or tetrahydrofuran at or near room temperature for about 2 to 10 hours to give the reduced macrolide.

The procedures described in Reaction Scheme F may be conducted on the mono-substituted products of Reaction Scheme B (and visa versa) to obtain the mixed disubstituted compounds. In fact, within Reaction Schemes B and F, treatment of the mono-substituted product with a different reagent will afford the mixed disubstituted compounds.

Reaction Scheme H:

Protection of the C-3'', C-4'' and/or the C-14 hydroxy group may be accomplished by methods known in the prior art for compounds of Formula II such as by treatment with: 2,6-lutidine and triisopropylsilyl trifluoromethanesulfonate in a solution of methylene chloride; 2,6-lutidine and t-butyldimethylsilyl trifluoromethanesulfonate in a solution of methylene chloride; pyridine and acetic anhydride in a solution of methylene chloride; pyridine and benzoyl chloride in a solution of methylene chloride; pyridine and p-nitrobenzoyl chloride in a solution of methylene chloride; imidazole and t-butyldiphenylsilyl chloride in a solution of methylene chloride; and the like. For example, as shown in Reaction Scheme H, the C-4'', 14-dihydroxy C-3''-methoxy macrolide (or the C-3'', 4'', 14-trihydroxy macrolide) may be protected at C-14 as the t-butyldimethylsilyl ether by treatment with t-butyldimethylsilyl trifluoromethanesulfonate in methylene chloride to give the C-4'',3''-di-O-TBDMS macrolide (or the C-3'',4'', 14-tri-O-TBDMS macrolide). Treatment with toluenesulfonic acid in methanol results in selective removal of the C-4'' silyl ether (and C-3'' silyl ether, if present) to give the C-14-O-TMBDMS macrolide.

Reaction Scheme I:

As shown in Reaction Scheme I, the 4''-hydroxy-3''-$R^2$O-macrolide or alternatively the 3''-hydroxy-4''-$R^1$O-macrolide (not depicted) (wherein $R^3$ is protected hydroxy or hydrogen) may be reacted with an alkenyl trichloroacetimidate (wherein $R^1$ is $C_{3-10}$ alkenyl) under conditions described in Reaction Scheme F to give the C-4''-O-alkenyl macrolide. Treatment with a stochiometric amount of osmium tetraoxide in an inert organic solvent, such as diethyl ether or tetrahydrofuran, in the presence of an amine base, such as pyridine or 4-methylmorpholine N-oxide, at or near room temperature gives the corresponding glycol (wherein A is $C_{1-8}$ alkyl). Treatment of the glycol with sodium metaperiodate in a solution of tetrahydrofuran/water gives the aldehyde. Alternatively, the alkenyl macrolide may be treated with sodium metaperiodate in the presence of a catalytic amount of osmium tetroxide in an organic solvent to give the aldehyde directly. The aldehyde can be further oxidized to the carboxylic acid by treatment with sodium chlorite in buffered, aqueous tert-butanol.

Reaction Scheme J:

A variety of compounds may be prepared from the corresponding aldehyde as illustrated in Reaction Scheme J. The aldehyde may be reacted with a primary or secondary amine (wherein $R^6$ and $R^7$ are as defined above) in an organic solvent such as tetrahydrofuran to give an imine which is reduced in situ with a hydride reducing agent, such as potassium triphenyl borohydride or sodium cyanoborohydride, to give the macrolide bearing as amino alkoxy functionality at C-4''. The aldehyde may also be reduced to the corresponding alcohol by treatment with a hydride reducing agent, such as potassium triphenyl borohydride or sodium cyanoborohydride in an organic solvent such as tetrahydrofuran. The alcohol may be further modified by utlizing the methods of Reaction Scheme B (wherein $R^1_a$ is unsubstituted or substituted phenyl, naphthyl or biphenyl) or Reaction Scheme F (wherein $R^1_b$ is unsubstituted or substituted alkyl, alkenyl or alkynyl). The procedures described in Reaction Scheme J are readily applicable to the preparation of compounds bearing analogous functionality at C-3''.

Reaction Scheme K:

Amide derivatives may be prepared from the carboxylic acid as illustrated in Reaction Scheme K. The carboxylic acid may be coupled with a primary or secondary amine, $HNR^6R^7$ (wherein $R^6$ and/or $R^7$ are as defined) by any of the peptide coupling methods commonly used in the art, such as with BOP reagent, DCC/HOBT, or EDC/HOBT.

Reaction Scheme L:

Hydroxy and keto derivatives may be prepared from the corresponding aldehyde as illustrated in Reaction Scheme L. The aldehyde is reacted with a nucleophilic organometallic reagent such as a Grignard reagent, an organolithium reagent, or an organocerium reagent in an organic solvent such as methylene chloride or tetrahydrofuran to give the substituted hydroxy compound. Removal of hydroxy protecting groups at other positions of the macrolide (if necessary) gives the macrolide bearing a substituted hydroxy alkoxy functionality at C-4″. The alcohol may also be oxidized to the corresponding ketone by well known methods, such as with 4-methylmorpholine-N-oxide in the presence of tetrapropylammonium perruthenate catalyst under dehydrative conditions. Removal of hydroxy protecting groups (if necessary) gives the macrolide bearing a substituted keto alkoxy functionality at C-4″. The procedures described in Reaction Scheme L are readily applicable to the preparation of compounds bearing analogous functionality at C-3″.

Reaction Scheme M:

Hydroxy macrolides (wherein $R^1$, $R^2$, and/or $R^3$ bear a hydroxy group) may be further derivatized by alkylation, acylation or phosphorylation to give ether, ester or phosphate derivatives (wherein $R^1$, $R^2$ and/or $R^3$ bear an $-OR^{11}$ as defined above) by procedures well known to the practitioner of the art.

The object compounds of Formula I obtained according to the reactions as explained above can be isolated and purified in a conventional manner, for example, extraction, precipitation, fractional crystallization, recrystallization, chromatography, and the like.

It is to be noted that in the aforementioned reactions and the post-treatment of the reaction mixture therein, the stereoisomer(s) of starting and object compounds due to asymmetric carbon atoms(s) or double bond(s) of the object compounds of Formula I may occasionally be transformed into the other stereoisomer(s), and such cases are also included within the scope of the present invention.

In the present invention, compounds with asymmetric centers may occur as racemates, as diastereomeric mixtures and as individual diastereomers, with all isomeric forms of the compounds being included in the present invention. These may be prepared by methods such as those disclosed in publications which describe synthetic routes to fragments of the macrolide FR-900506 and the total synthesis of the macrolide FR-900506 itself (See for example, J. Am. Chem. Soc. 1989, 111, 1157; J. Am. Chem. Soc. 1990, 112, 2998; J. Org. Chem. 1990, 55, 2786; J. Am. Chem. Soc. 1990, 112, 5583. Tetrahedron Lett. 1988, 29, 277; Tetrahedron Lett. 1988, 29, 281; Tetrahedron Lett. 1988, 29, 2895; J. Org. Chem. 1988, 53, 4643; Tetrahedron Lett. 1988, 29, 4245; Tetrahedron Lett. 1988, 29, 4481; J. Org. Chem. 1989, 54, 9; J. Org. Chem. 1989, 54, 11; J. Org. Chem. 1989, 54, 12; J. Org. Chem. 1989, 54, 15; J. Org. Chem. 1989, 54, 17; Tetrahedron Lett. 1989, 30, 919; Tetrahedron Lett. 1989, 30, 1037; J. Org. Chem. 1989, 54, 2785; J. Org. Chem. 1989, 54, 4267; Tetrahedron Lett. 1989, 30, 5235; Tetrahedron Lett. 1989, 30, 6611; Tetrahedron Lett. 1989, 30, 6963; Synlett 1990, 38; J. Org. Chem. 1990, 55, 2284; J. Org. Chem. 1990, 55, 2771; J. Org. Chem. 1990, 55, 2776; Tetrahedron Lett. 1990, 31, 1439; Tetrahedron Lett. 1990, 31, 1443; Tetrahedron Lett. 1990, 31, 3007; Tetrahedron Lett. 1990, 31, 3283, 3287).

The compounds of the present invention are capable of forming salts with various inorganic and organic acids, and bases and such salts are also within the scope of this invention. Examples of such acid addition salts (which are negative counterions defined herein as $M^-$) include acetate, adipate, benzoate, benzenesulfonate, bisulfate, butyrate, citrate, camphorate, camphorsulfonate, ethanesulfonate, fumarate, hemisulfate, heptanoate, hexanoate, hydrochloride, hydrobromide, hydroiodide, methanesulfonate, lactate, maleate, methanesulfonate, 2-naphthalenesulfonate, oxalate, pamoate, persulfate, picrate, pivalate, propionate, succinate, tartrate, tosylate, and undecanoate. Base salts (which are positive counterions defined herein as $M^+$) include ammonium salts, alkali metal salts such as sodium, lithium and potassium salts, alkaline earth metal salts such as calcium and magnesium salts, salts with organic bases such as dicyclohexylamine salts, N-methyl-D-glucamine, and salts with amino acids such as arginine, lysine and so forth. Also, the basic nitrogen-containing groups may be quaternized with such agents as: lower alkyl halides, such as methyl, ethyl, propyl, and butyl chloride, bromides and iodides; dialkyl sulfates like dimethyl, diethyl, dibutyl; diamyl sulfates; long chain halides such as decyl, lauryl, myristyl and stearyl chlorides, bromides and iodides; aralkyl halides like benzyl bromide and others. The non-toxic physiologically acceptable salts are preferred, although other salts are also useful, such as in isolating or purifying the product.

The salts may be formed by conventional means, such as by reacting the free base form of the product with one or more equivalents of the appropriate acid in a solvent or medium in which the salt is insoluble, or in a solvent such as water which is removed in vacuo or by freeze drying or by exchanging the anions of an existing salt for another anion on a suitable ion exchange resin.

C. Utility of the compounds within the scope of the invention

The compounds of Formula I may be employed as immunosuppressants or antimicrobial compounds by methods and in dosages known in the prior art for compounds of Formula II. These compounds possess pharmacological activity such as immunosuppressive activity, antimicrobial activity, and the like, and therefore are useful for the treatment and prevention of the resistance to transplantation or transplantation rejection of organs or tissues such as heart, kidney, liver, duodenum, small-bowel, medulla ossium, skin, pancreatic islet-cell, etc., graft-versus-host diseases by medulla ossium transplantation, automimmune diseases such as rheumatoid arthritis, systemic lupus erthematosis, Hashimoto's thyroiditis, multiple sclerois, myasthenia gravis, type I diabetes, uveitis, allergic encephalomyelitis, glomerulonephritis, etc., and infectious diseases cuased by pathogenic microorganisms.

The compounds of Formula I are also useful for treating or preventing inflammatory and hyperproliferative skin diseases and cutaneous manifestations of immunologically-mediated illnesses such as: psoriasis, atopical dermatitiis, contact dermatitis and further eczematous dermatitises, seborrhoeic dermatitis, Lichen planus, Pemphigus, bullous Pemphigoid, Epidermolysis bullosa, urticaria, angioedemas, vasculitides, erythemas, acne, cutaneous eosinophilias or Alopecia areata. More particularly, the compounds of Formula I are useful in hair revitalizing, such as in the treatment or prevention of male pattern alopecia or alopecia senilis, by providing epilation prevention, hair germination, and/or a promotion of hair generation and hair growth.

The compounds of Formula I are further useful for treating or preventing reversible obstructive airways disease, including conditions such as asthma, including bronchial asthma, allergic asthma, intrinsic asthma, extrinsic asthma and dust asthma, particularly chronic or inveterate asthma (for example late asthma and airway hper-responsiveness), bronchitis and the like. The compounds of Formula I may also be useful for treating hepatic injury associated with ischemia.

The compounds of Formula I are also useful for treating multidrug resistance of tumor cells, (i.e. enhancing the activity and/or sensitivity of chmmoterapeutic agents), preventing or treating inflammation of mucosa or blood vessels, LTB$_4$-mediated diseases, gastric ulcers, vascular damage cuased by ischemic diseases and thrombosis, ischemic bowel disease, inflammatory bowel disease (e.g., Crohn's disease and ulcerative colitis) necrotizing enterocolitis, or intestinal lesions associated with thermal burns, cytomegalovirus infection, particularly HCMV infection, idiopathic thrombocytopenic purpura and Basedow's disease.

Further, the compounds of Formula I are also useful for treating or preventing renal diseases selected from interstitial nephritis, Goodpasture's syndrome, hemolytic-uremic syndrome and diabetic nephropathy; nervous diseases selected from multiple myositis, Guillain-Barre syndrom, Meniere's disease and radiculopathy; enocrine diseases selected from hyperthyroidism; hematic diseases selected from pure red cell aplasia, aplastic anemia, hypoplastic anemia, autoimmune hemolytic anemia, agranulocytosis and anerythroplasia; bone diseases such as ostoporosis; respiraoty diseases selected from sarcoidosis, fibroid lung and idiopathic interstitial pneumonia; eye diseases selected from herpetic keratitis, conical cornea, dystronphia epithelialis corneasa, corneal leukmas, ocular pemphigus, Mooren's ulcer, scleritis and Grave's ophthalmopathy; skin diseases selected from dermatomyositis, leukoderma vulgaris, ichthyosis vulgaris, photoallergic sensitivity and cutaneous T cell lymphoma; circulatory diseases selected from arteriosclerosis, aortitis syndrome, polyarteritis nodosa and myocardosis; collagen diseases selected from scleroderma, Wegener's granuloma and Sjogren's syndrome; adiposis; eosinophilic fascitis; periodontal disease; and muscular dystrophy.

The pharmaceutical compositions of this invention can be used in the form of a pharmaceutical preparation, for example, in solid, semisolid or liquid form, which contains one or more of the compounds of the present invention, as an active ingredient, in admixture with an organic or inorganic carrier or excipient suitable for external, enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, semisolid, or liquid form, and in addition auxiliary, stabilizing, thickening and coloring agents and perfumes may be used. For example, the compounds of Formula I may be utilized with hydroxypropyl methylcellulose essentially as described in U.S. Pat. No. 4,916,138, issued Apr. 10, 1990, or with a surfactant essentially as described in EPO Publication 0,428,169. Oral dosage forms may be prepared essentially as described by T. Hondo, et al., *Transplantation Proceedings*, 1987, XIX, Supp. 6, 17-22. Dosage forms for external application may be prepared essentially as described in EPO Publication 0,423,714. The active object compound is included in the pharmaceutical composition in an amount sufficient to produce the desired effect upon the process or condition of diseases.

For the treatment of these conditions and diseases caused by immunoirregularity a compound of formula I may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections intravenous, intramuscular, intrasternal injection or infusion techniques.

Dosage levels of the compounds of the present invention are of the order from about 0.005 mg to about 50 mg per kilogram of body weight per day, preferably from about 0.1 mg to about 10 mg per kilogram of body weight per day, are useful in the treatment of the above-indicated conditions (from about 0.7 mg to about 3.5 per patient per day, assuming a 70 kg patient). In addition, the compounds of the present invention may be administered on an intermittent basis; i.e. at daily, semiweekly, weekly, semi-monthly or monthly intervals.

The amount of active ingredient that may be combined with the carrier materials to produce a signle dosage form will vary depending upon the host treated and the particular mode of administration. For example, a formulation intended for the oral administration of humans may contain from 0.5 mg to 5 gm of active agent compounded with an appropriate and convenient amount of carrier material which may vary from about 5 to about 95 percent of the total composition. Dosage unit forms will generally contain from about 0.5 mg to about 500 mg of active ingredient, and preferably about 0.5 mg to about 100 mg of active ingredient. For external administration the compound of Formula I may be formulated within the range of, for example, 0.0001% to 60% by weight, preferably from 0.001 to 10% by weight, and most preferably from about 0.0005 to 0.8% by weight.

It will be understood, however, that the specific dose level for any particular patient will depend on a variety of factors including the activity of the specific compound employed, the age, body weight, general health, sex, diet, time of administration, route of administration, rate of excretion, drug combination and the severity of the particular disease undergoing therapy.

The Following examples are given for the purpose of illustrating the present invention and shall not be construed as being limitations on the scope or spirit of the instant invention.

EXAMPLE 1

17-Ethyl-1,14-dihydroxy-12-[2'-(4''-phenyloxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a stirred solution of 17-ethyl-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (100 mg, 0.126 mmol, 1 eq) and Cu(OAc)$_2$ (2.8 mg, 0.014 mmol. 0.11 eq) in CH$_2$Cl$_2$ (1 ml)

in a 16 mL screw-cap vial equipped with a magnetic stir-bar was added triphenyl bismuth diacetate [prepared immediately prior to use by addition of acetic acid (0.030 mL, 0.504 mmol, 4 eq) to a suspension of triphenyl bismuth carbonate (127 mg, 0.253 mmol. 2 eq) in CH$_2$Cl$_2$ (1 ml)]. The reaction vessel was capped and the mixture stirred for five days. The reaction mixture was diluted with several milliliters of saturated aqueous NaHCO$_3$ and extracted 4 times with CH$_2$Cl$_2$. The organic extracts were combined, dried over anhydrous Na$_2$SO$_4$, filtered and concentrated in vacuo. The product was isolated by preparative TLC on silica gel (eluted with 3:4 EtOAc/hexanes to afford 46 mg of 17-ethyl-1,14-dihydroxy 12-[2'-(4''-phenyloxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone. ($^1$H NMR, $^{13}$C NMR and mass spectral analysis were consistent with the desired structure.)

EXAMPLE 2

A.

17-Ethyl-1,14-dihydroxy-12-[2'-(3''-phenyloxy-4''-hydroxycyclohexyl)-1'-methylvinyl]-23,25-dimethoxy-13,19,21,-27-tetramethyl-11,28-dioxa-4-azatricyclo[22.3.1.0$^{4,9}$]octacos-18-ene-2,3,10,16-tetraone and

B.

17-Ethyl-1,14-dihydroxy-12-[2'-(4''-phenyloxy-3''-hydroxycyclohexyl)-1'-methylvinyl]-23,25-dimethoxy-13,19,21,-27-tetramethyl-11,28-dioxa-4-azatricyclo[22.3.1.0$^{4,9}$]octacos-18-ene-2,3,10,16-tetraone To a stirred solution of 17-ethyl-1,14-dihydroxy-12-[2'-(341 , 4''-dihydroxycylohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (500 mg, 0.644 mmol, 1 eq) and Cu(OAc)$_2$ (12 mg, 0.064 mmoo, 0.1 eq) in CH$_2$Cl$_2$ (10 ml) in a 25 ml recovery flask equipped with a magnetic stir-bar was added triphenyl bismuth diacetate [prepared immediately prior to use by addition of acetic acid (0.220 ml. 3860 mmol, 6 eq) to a suspension of triphenyl bismutt carbonate (483 mg, 0.965 mmol, 1.5 eq) in CH$_2$Cl$_2$ (10 ml)]. The reaction flask was capped and the mixture stirred at room temperature for 6 hours. The flask was then fitted with a condenser and the mixture was warmed to 40° C. After 40 hours the reaction mixture was cooled, diluted with saturated aqueous NaHCO$_3$ and extracted 4 times with CH$_2$Cl$_2$. The organic extracts were combined, dried over anhydrous Na$_2$SO$_4$, filtered and concentrated in vacuo. the products were separated and purified by flash column chromatography on silica gel [eluted with 4:1 hexanes/acetone followed by preparative tLC on silica gel (eluted with 2:1 hexanes/acetone] to yield 94 mg of 17-ethyl-1, 14-dihydroxy-1 2-[2'-(4''-phenyloxy-3''-hydroxycyclohexyl)-1'-methylvinyl]-23,25-dimethoxy-13,19,21,27-tetra-methyl-11,28-dioxa-4-azatricylo[22.3.1.0$^{4,9}$]-octacos-18-ene-2,3,10,16-tetraone and 110 mg of 17-ethyl-1,14-dihydroxy-12-[2'-(3''-hydroxycyclo-hexyl)-1'-methylvinyl]-23,25-dimethoxy-13, 19, 21, 27-tetramethyl-11, 28-dioxa-4-azatricyclo[22.3.1.0$^{4,9}$]-octacos-18-ene-2,3,10,16-tetraone. ($^1$H NMR, $^{13}$C NMR and mass spectral analysis were consistent with the desired structure).

EXAMPLE 3

17-Ethyl-1,14-dihydroxy-12-[2'-(4''''-fluo rophenyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a stirred mixture of 17-ethyl-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (100 mg, 0.126 mmol, 1 eq) and Cu-(OAc)$_2$ (3 mg, 0.0165 mmol, 0.13 eq) in CH$_2$Cl$_2$ (1 ml) in a 4 mL screw-cap vial equipped with a magnetic stir-bar was added tri(4-fluorophenyl)bismuth diacetate [prepared immediately prior to use by addition of acetic acid (0.030 mL, 0.504 mmol, 4 eq) to a suspension of tri(4-fluorophenyl)bismuth carbonate (100 mg, 0.181 mmol, 1.4 eq) in CH$_2$Cl$_2$ (1 mL)]. The reaction vessel was capped and the mixture stirred for two days. The reaction mixture was diluted with several milliliters of saturated aqueous NaHCO$_3$ and extracted 2 times with CH$_2$Cl$_2$. The organic extracts were combined, dried over anhydrous Na$_2$SO$_4$, filtered and concentrated in vacuo. The product was isolated by preparative TLC on silica gel (eluted with 3:1 hexanes/EtOAc) to afford 39 mg of 17-ethyl-1,14-dihydroxy-12-[2'-(4''-(4''''-fluo rophenyloxy)-3''-methoxycyclohexyl)-1'-methyl-vinyl]-23,25-dimethoxy-13,19,21,27-tetramethyl-11,28-dioxa-4-azatricyclo-22.3.1.0$^{4,9}$]octacos-18-ene-2,3,10,16-tetraone. ($^1$H NMR, $^{13}$C NMR and mass spectral analysis were consistent with the desired structure).

EXAMPLE 4

17-Ethyl-1,14-dihydroxy-12-[2'-(4''-(4''''-chlor ophenyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a stirred mixture of 17-ethyl-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (150 mg, 0.189 mmol, 1 eq) and Cu-(OAc)$_2$ (6.1 mg, 0.033 mmol, 0.17 eq) in CH$_2$Cl$_2$ (2.5 ml) in a round bottom flask equipped with a magnetic stir-bar was added tri(4-chlorophenyl)bismuth diacetate [prepared immediately prior to use by addition of acetic acid (0.075 ml, 1.3 mmol, 6.9 eq) to a suspension of tri(4-chlorophenyl)bismuth carbonate (200 mg, 0.331 mmol, 1.75 eq) in CH$_2$Cl$_2$ (2.5 ml)]. The reaction flask was then fitted with a reflux condenser and the mixture warmed to 40° C. After 20 hours the reaction mixture was cooled, diluted with saturated aqueous NaHCO$_3$ (10 mL) and extracted 4 times with CH$_2$Cl$_2$. The organic extracts were dried over anhydrous Na$_2$SO$_4$, filtered and concentrated in vacuo. The product was separated and purified two times by preparative TLC on silica gel (eluted with 2:1 hexanes/acetone) to give 40 mg 17-ethyl-1,14-dihydroxy-12-[2'-(4''-(4''''-ch lorophenyloxy)-3''-methoxycyclohexyl)-1'-methyl-vinyl[-23,25-dimethoxy-13,19,21,27-tetramethyl-11,28-dioxa-4-azatricyclo[22.3.1.0$^{4,9}$]octacos-18-ene-2,3,10,16-tetraone. ($^1$H NMR, $^{13}$C NMR, and mass spectral analysis were consistent with the desired strcture).

EXAMPLE 5

17-Ethyl-1,14-dihydroxy-12-[2'-(4"-(4'''-methylphenyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a stirred mixture of 17-ethyl-1,14-dihydroxy-12-[2'-(4"-hydroxy-3"-methoxycyclohexyl)-1'-methylvinyl]-23,25-dimethoxy-13,19,21,27-tetramethyl-11,28-dioxa-4-azatricyclo[22.3.1.0.$^{4,9}$]octacos-18-ene-2,3,10,16-tetraone (100 mg, 0.126 mmol, 1 eq) and Cu-(OAc)$_2$ (3 mg, 0.0165 mmol, 0.13 eq) in CH$_2$Cl$_2$ (1 ml) in a 4 mL screw cap vial equipped with a magnetic stir-bar was added tri(4-tolyl)bismuth diacetate [prepared immediately prior to use by addition of acetic acid (0.030 ml, 0.525 mmolo, 4.2 eq) to a suspension of tri(4-tolyl)-bismuth carbonate (130 mg, 0.234 mmol, 1.86 eq) in CH$_2$Cl$_2$ (1 ml)]. The reaction vessel was capped and the mixture stirred for 20 hours at which time TLC analysis showed the reaction to be incomplete. The mixture was treated with additional tri(4-tolyl) bismuth diacetate (0.234 mmol) and stirred for 24 hours then poured into saturated aqueous NaHCO$_3$ and extracted 2 times with CH$_2$Cl$_2$. The organic extracts were combined, drried over anhydrous Na$_2$SO$_4$, filtered and concentrated in vacuo. The product was isolated by preparative TLC on silica gel (eluted with 2:1 hexanes/EtOAc) to give 47 mg 17-ethyl-1,14-dihydroxy-12-[2'-(4"-(4'''-methylphenyloxy)-3"-methoxy-cyclohexyl)-1'-methylvinyl]-23,25-dimethoxy-13,19,21,27-tetramethyl-11,28-dioxa-4-azatricyclo[ 22.3.1.0$^{4,9}$]octacos-18-ene-2,3,10,16-tetraone. ($^1$H NMR, $^{13}$C NMR, and mass spectral analysis were consistent with the desired structure.)

EXAMPLE 6

A.

17-Ethyl-1,14-dihydroxy-12-[2'-(3"-(4'''-methylphenyloxy)-4"-hydroxycylohexy)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone and

B.

17-Ethyl-1,14-dihydroxy-12-[2'-(4"-(4'''-methylphenyloxy)-3"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a stirred mixture of 17-ethyl-1,14-dihydroxy-12-[2'-(3", 4"-dihydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (200 mg, 0.257 mmol, 1 eq) and Cu(OAc)$_2$ (10 mg, 0.055 mmol, 0.2 eq) in CH$_2$Cl$_2$ (2 ml) in a round bottom flask equipped with a magnetic stir-bar was added tri(4-tolyl)bismuth diacetate [prepared immediately prior to use by addition of acetic acid (0.075 ml, 1.31 mmol, 5.1 eq) to a suspension of tri(4-tolyl) bismuth carbonate (300 mg, 0.553 mmol, 2.1 eq) in CH$_2$Cl$_2$(2 ml)]. The reaction flask was fitted with a reflux condenser and the mixture warmed to 40° C. for 5 hours then stirred without heating. After 18 hours the reaction mixture was diluted with saturated aqueous NaHCO$_3$ and extracted 2 times with CH$_2$Cl$_2$. The organic extracts were combined, dried over anhydrous Na$_2$SO$_4$, filtered and concentrated in vacuo. The products were separated and purified by preparative TLC on silica gel (eluted with 2:1 hexanes/acetone) to zfford 31 mg of 17-ethyl-1,14-dihydroxy-12-[2-'-(3"-(4'''-methylphenyloxy)-4"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone and 42 mg of 17-ethyl-1,14-dihydroxy-12-[2'-(4"-(4'''-methylphenyloxy)-3"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone. ($^1$H NMR and $^{13}$C NMR analysis were consistent with the desired structures).

EXAMPLE 7

17-Ethyl-1,14-dihydroxy-12-[2'-(4"-(4'''-phenoxyphenyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone A stirred mixture of 17-ethyl-1,14-dihydroxy-12-[2'-(4"-hydroxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (150 mg, 0.19 mmol, 1 eq) and Cu(OAc)$_2$ (6.0 mg, 0.033 mmol, 0.17 eq) in CH$_2$Cl$_2$ (2.5 ml) in a round bottom flask equipped with a magnetic stir-bar and reflux condenser was heated to 40° C. then treated with tri(4-phenoxyphenyl)bismuth diacetate [prepared immediately prior to use by addition of acetic acid (0.075 mL, 1.31 mmol, 6.9 eq) to a suspension of tri(4-phenoxyphenyl)bismuth carbonate (225 mg, 0.29 mmol, 1.5 eq) in CH$_2$Cl$_2$ (2.5 ml)]. After 18 hours TLC analysis showed the reaction to be incomplete and additional tri(4-phenoxyphenyl) bismuth diacetate (0.10 mmol) was added. The reaction mixture was stirred with heating for 5 hours then cooled, diluted with saturated aqueous NaHCO$_3$, and extracted 2 times with CH$_2$Cl$_2$. The extracts were combined, dried over Na$_2$SO$_4$, filtered, and concentrated in vacuo. The product was isolated and purified by preparative TLC on silica gel (2:1 hexanes/acetone) to give 66 mg of 17-ethyl-1,14-dihydroxy-12-[2'-(4"-(4'''-penoxyphenyloxy)-3"-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone. ($^1$H NMR, $^{13}$C NMR, and mass spectral analysis were consistent with the desired structure).

EXAMPLE 8

A.

17-Ethyl-1,14-dihydroxy-12-[2'-(4"-(4'''-phenoxyphenyloxy)-3"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone and

B.

17-Ethyl-1,14-dihydroxy-12-[2'-(3"-(4'''-phenoxyphenyloxy)-4"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a stirred mixture of 17-ethyl-1,14-dihydroxy-12-[2'-(3",4"-dihydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (150 mg, 0.19 mmol, 1 eq) and Cu-(OAc)$_2$ (7 mg, 0.039 mmol, 0.21 eq) in CH$_2$Cl$_2$ (2 mL) in a round bottom flask equipped with a magnetic stir-bar was added tri(4-phenoxyphenyl)bismuth diacetate [prepared immediately prior to use by addition of acetic acid (0.070 ml, 1.22 mmol, 6.4 eq) to a suspension of tri(4-phenoxyphenyl)bismuth carbonate (230 mg, 0.30 mmol., 1.58 eq) in $CH_2Cl_2$ (2 mL)]. The reaction flask was fitted with a reflux condenser and the mixture warmed to 40° C. After 4 hours the mixture was cooled, diluted with saturated aqueous $NaHCO_3$, and extracted 2 times with $CH_2Cl_2$. The extracts were combined, dried over $Na_2SO_4$, filtered, and concentrated in vacuo. The products were separated and purified 3× by preparative TLC on silica gel (3:2 hexanes/acetone) to afford 35 mg of 17-ethyl-1,14-dihydroxy-12-[2'-(4''-(4-'''-phenoxyphenyloxy)-3''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone and 42 mg of 17-ethyl-1,14-dihydroxy-12-[2'-(3''-(4'''-phenoxyphenyloxy)-4''-hydroxycyclohexyl)-1'-methylvinyl[     -23,25-dimethoxy-13,19,21,27-tetramethyl-11,28-dioxa-4-azatricyclo[22.3.1.0$^{4,9}$]octacos-18-ene-2,3,10,16-tetraone. ($^1$H NMR, $^{13}$C NMR, and mass spectal analysis were consistent with the desired structures).

EXAMPLE 9

17-Ethyl-1,14-dihydroxy-12-[2'-(4''-(naphth-1-yloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a stirred mixture of 17-ethyl-1,14-dihydroxy-12-[2'-(4''-hydroxy-3''-methoxycyclohexyl)-1'-methylvinyl[-23,25-dimethoxy-13,19,21,27-tetramethyl-11,28-dioxa-4-azatricyclo[22.3.1.0$^{4,9}$]octacos-18-ene-2,3,10,16-tetraone (150 mg, 0.19 mmol, 1 eq) and Cu(OAc)$_2$ (6 mg, 0.033 mmol, 0.17 eq) in $CH_2Cl_2$ (2 ml) in a round bottom flask equipped with a magentic stir-bar was added tri(1-naphthyl)bismuth diacetate [prepared immediately prior to use by addition of acetic acid (0.070 ml, 1.22 mmol, 6.4 eq) to a suspension of tri(1-naphthyl)bismuth carbonate (150 mg, 0.23 mmol, 1.2 eq) in $CH_2Cl_2$ (2 ml)]. The reaction flask was then fitted with a reflux condenser and the mixture was warmed to 40° C. for 4 hours. After stirring an additional 16 hours at room temperature TLC analysis showed the reaction to be incomplete. The reaction mixture was further treated with tri(1-naphthyl)bismuth diacetate (0.15 mmol) and heated to 40° C. for 4 hours. The mixture was cooled, diluted with saturated aqueous $NaHCO_3$, and extracted 2 times with $CH_2Cl_2$. The extracts were combined, dried over anhydrous $Na_2SO_4$, filtered, and concentrated in vacuo. The product was isolated and purified 2 times by preparation TLC on silica gel (3:1 hexanes/acetone) to give 38 mg of 17-ethyl-1,14-dihydroxy-12-[2'-(4''-(naphth-1-yloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone. ($^1$H NMR analysis was consistent with the desired structure).

EXAMPLE 10

A.

17-Ethyl-1,14-dihydroxy-12-[2'-(3''-(naphth-1-yloxy)-4''-hydroxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone and

B.

17-Ethyl-1,14-dihydroxy-12-[2'-(4''-(naphth-1-yloxy)-3''-hydroxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone To a stirred mixture of 17-ethyl-1,14-dihydroxy-12-[2'-(3'',4''-dihydroxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,-10,16-tetraone (250 mg, 0.32 mmol, 1 eq) and Cu(OAc)$_2$ (15 mg, 0.08 mmol, 25 eq) in $CH_2Cl_2$ (5 ml) in a round bottom flask equipped with a magnetic stir-bar was added tri(1-naphthyl) bismuth diacetate [prepared immediately prior to use by addition of acetic acid (0.100 ml, 1.75 mmol, 5.46 eq) to a suspension of tri(1-naphthyl) bismuth carbonate (350 mg, 0.54 mmol, 1.69 eq) in $CH_2Cl_2$ (5 ml)]. The reaction flask was fitted with a reflux condenser and the mixture warmed to 40° C. for 5 hours then stirred at room temperature. After 16 hours the mixture was diluted with saturated aqueous $NaHCO_3$ extracted 2 times with $CH_2Cl_2$. The extracts were combined, dried over anhydrous $Na_2SO_4$, filtered, and concentrated in vacuo. The products were separated and purified by preparative TLC on silica gel (eluted with 3:1 hexanes/acetone) to yield 49 mg of 17-ethyl-1,14-dihydroxy-12-[2'-(3''-(naphth-1-yloxy)-4''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone and 39 mg of 17-ethyl-1,14-dihydroxy-12-[2'-(4''-(naphth-1-yloxy)-3''-hydroxycyclohexyl)-1'-methylvinyl]-23,25-dimethoxy-13,19,21, 27-tetramethyl-1,28-dioxa-4-azatricyclo[22.3.1.0$^{4,9}$]-octacos-18-ene-2,3,10,16-tetraone. ($^1$H NMR analysis was consistent with the desired structure).

EXAMPLE 11

17-Ethyl-1,14-dihydroxy-12-[2'-(4''-(naphth-2-yloxy)-3''-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone To a stirred mixture of 17-ethyl-1,14-dihydroxy-12-[2'-(4''-hydroxy-3''-methoxycyclohexyl)-1'-methylvinyl]- 23,25-dimethoxy-13,19,21,27-tetramethyl-11,28-dioxa-4-azatricyclo[22.3.1.0$^{4,9}$]octacos-18-ene-2,3,10,16-tetraone (150 mg, 0.189 mmol, 1 eq) and Cu(OAc)$_2$ (6 mg, 0.033 mmol, 0.17 eq) in $CH_2Cl_2$ (2.5 mL) in a round bottom flask equipped with a magnetic stir-bar was added tri(2-naphthyl)bismuth diacetate [prepared immediately prior to use by addition of acetic acid (0.075 ml, 1.31 mmol, 6.9 eq) to a suspension of tri(2-naphthyl)bismuth carbonate in $CH_2Cl_2$ (2.5 ml)]. The reaction flask was fitted with a reflux condenser and the mixture warmed to 40° C. After 4 hours the heating was discontinued and the mixture stirred at room temperature for 16 hours. The mixture was then diluted with saturated aqueous $NaHCO_3$ and extracted 2 times with $CH_2Cl_2$. The extracts were combined, dried over anhydrous Na$_2$SO$_4$, filtered, and concentrated in vacuo. The product was isolated and purified by preparative TLC on silica gel (3:1 hexanes/acetone) to afford 32 mg of 17-ethyl-1,14-dihydroxy-12-[2'-(4''-(naphth-2-yloxy)-3''-methoxycyclohexyl)-1'-methylvinyl]-23,25-dimethoxy-13,19,21-27-tetramethyl-11,28-dioxa-4-azatricyclo[22.3.1.0$^{4,9}$]-octacos-18-ene-2,3,10,16-tetraone. ($^1$H NMR, $^{13}$C NMR, and mass spectral analysis were consistent with the desired structure).

EXAMPLE 12

A.

17-Ethyl-1,14-dihydroxy-12-[2'-(4''-(naphth-2-yloxy)-3''-hydroxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone and

B.

17-Ethyl-1,14-dihydroxy-12-[2'-(3''-(naphth-2-yloxy)-3''-hydroxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone To a stirred mixture of 17-ethyl-1,14-dihydroxy-12-[2'-(3'',4''-dihydroxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,-10,16-tetraone (250 mg, 0.32 mmol, 1 eq) and Cu(OAc)$_2$ (10 mg, 0.055 mmol, 0.17 eq) in CH$_2$Cl$_2$ (5.5 ml) in a round bottom flask equipped with a magnetic stir-bar was added tri(2-naphthyl) bismuth diacetate [prepared immediately prior to use by addition of acetic acid (0.100 ml, 1.75 mmol, 5.46 eq) to a suspension of tri(2-naphthyl)bismuth carbonate (350 mg, 0.538 mmol, 1.7 eq) in CH$_2$Cl$_2$ (5.5 ml)]. The reaction flask was fitted with a reflux condenser and the mixture warmed to 40° C. for 4 hours then stirred at room temperature. After 3 days the reaction mixture was diluted with saturated aqueous NaHCO$_3$ and extracted 3 times with CH$_2$Cl$_2$. The extracts were combined, dried over anhydrous Na$_2$SO$_4$, filtered, and concentrated in vacuo. The products were separated and purified by preparative TLC on silica gel (eluted with 3:1 hexanes/acetone) to give 63 mg of 17-ethyl-1,14-dihydroxy-12-[2'-(3''-(napth-2-yloxy)-4''-hydroxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone and 49 mg of 17-ethyl-1,14-dihyroxy-12-[2'-(4''-(naphth-2-yloxy)- 3''-hydroxycyclohexyl)-1'-methylvinyl]-23,25-dimethoxy-13,19,21,27-tetramethyl-11,28-dioxa-4-azatricyclo[22.3.1.0$^{4,9}$ octacos-18-ene-2,3,10,16-tetraone. ($^1$H NMR was consistent with the desired structure).

EXAMPLE 13

17-Ethyl-1-hydroxy-12-[2'-(4''-(naphth-2-yloxy)-3''-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone To a stirred mixture of 17-ethyl-1-hydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,-10,16-tetraone (300 mg, 0.39 mmol, 1 eq) and Cu(OAc)$_2$ (15 mg, 0.083 mmol, 0.21 eq) in CH$_2$Cl$_2$ (5 ml) in a round bottom flask equipped with a magnetic stir-bar was added tri(2-naphthyl)bismuth diacetate [prepared immediately prior to use by addition of acetic acid to a suspension of tri(2-naphthyl)bismuth carbonate (300 mg, 0.461 mmol, 1.2 eq) in CH$_2$Cl$_2$ (5 ml)]. The reaction flask was fitted with a reflux condenser and the mixture warmed to 40° C. After 6 hours the mixture was allowed to cool to room temperature and stirred an additional 16 hours. The reaction mixture was diluted with saturated aqueous NaHCO$_3$ and extracted 2 times with CH$_2$Cl$_2$. The extracts were combined, dried over anhydrous Na$_2$SO$_4$, filtered, and concentrated in vacuo. The product was isolated and purified by preparative TLC (3:1 hexanes-/acetone) to give 109 mg of 17-ethyl-1-hydroxy-12--[2'-(4''-(naphth-2-yloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone. ($^1$H NMR and $^{13}$C NMR analysis were consistent with the desired structure).

EXAMPLE 14

17-Ethyl-1,14-dihydroxy-12-[2'-(4''-(6'''-methoxynaphth-2-yloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of tri-(6-methoxy-2-naphthyl)bismuth diacetate (52 mg, 0.069 mmol, 1.1 eq) in methylene chloride (2 ml) in a 10 ml round bottom flask equipped with a stir bar was added 17-ethyl-1,14-dihydroxy-12-[2'-(4''-hydroxy-3''-methoxycyclohexyl)-1'-methylvinyl]-23,25-dimethoxy-13,9,21,27-tetramethyl-11,28-dioxa-4-azatricyclo[22.3.1.0$^{4,9}$]octacos-18-ene-2,3,10,16-tetraone (50 mg, 0.063 mmol, 1 eq). To the reaction mixture was added a catalytic amount of Cu(OAc)$_2$ (approximately 20 mg). The reaction flask was fitted with a reflux condenser and the mixture was warmed to 40° C. After 1 hour the mixture was cooled, diluted with saturated aqueous NaHCO$_3$ and extracted 4 times with CH$_2$Cl$_2$. The organic extracts were combined, dried over anhydrous Na$_2$SO$_4$, filtered and concentrated in vacuo. The product was isolated by two preparative thin layer chromatographys on silica gel (first chromatography eluted with 2:1 hexanes/acetone, isolated band at R$_f$=0.26 second chromatography eluted with 3.5% methanol/CH$_2$Cl$_2$, isolated band at R$_f$=0.62) to give 20 mg of 17-ethyl-1,14-dihydroxy-12-[2'-(4''-(6'''-methoxy-naphth-2-yloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone. ($^1$H NMR and mass spectral analysis were consistent with the desired structure).

EXAMPLE 14A

General procedure for the preparation of triarylbismuthines

To a stirred suspension of magnesium (486 mg, 20 mmol) in dry tetrahydrofuran (10 mL) is added slowly a solution of aryl halide (20 mmol) in dry tetrahydrofuran (10 mL). If necessary the mixture is warmed gently to effect Grignard formation. To the stirred solution of the Grignard reagent is added a solution of bismuth trichloride (1.9 g, 6 mmol) dissolved in dry tetrahydrofuran (20 mL). The resulting mixture is stirred for 24 hours. The reaction mixture is poured into a separatory funnel containing brine and extracted 4× with CH$_2$Cl$_2$. The organic extracts were combined and dried over anhydrous Na$_2$SO$_4$. The mixture was filtered and concentrated in vacuo. The triarylbismuthine is isolated and purified by flash column chromatography on silica gel.

EXAMPLE 14B

Tri(6-Methoxy-2-naphthyl)bismuth diacetate

To a stirred solution of tris(6-methoxynaphth-2-yl)bismuthine (100 mg, 0.158 mmol) in $CH_2Cl_2$ (8 mL) was added iodobenzene diacetate (200 mg, 0.621 mmol). The $CH_2Cl_2$ was removed in vacuo and the residue was dissolved in several milliliters of 4:1 hexanes/acetone plus small amount of $CH_2Cl_2$. The solution was passed through a silica gel plug and eluted with 4:1 hexanes/acetone. The filtrate was concentrated in vacuo. The residue was dissolved in 4:1 hexanes/acetone plus small amount of $CH_2Cl_2$ and passed through a second silica gel plug and eluted with 4:1 hexanes/acetone. The filtrate was concentrated in vacuo leaving 52 mg yellow residue that was used without further purification.

EXAMPLE 15

A.

17-Ethyl-1,14-dihyd roxy-12-[2'-(3''-(6'''-methoxynaphth-2-yloxy)-4''-hydroxycyclohexyl)-1'-methylvinyl]-23,25-dimethoxy-13,19,2,27-tetramethyl-11,28-dioxa-4-azatricyclo-[22.3.1.0$^{4,9}$] octacos-18-ene-2,3,10,16-tetraone and

B.

17-Ethyl-1,14-dihydroxy-12-[2'-(4''-(6'''-methoxynap hth-2-yloxy)-3''-hydroxycyclohexyl)-1'-methylvinyl]-23,25-dimethoxy-13,19,21,27-tetramethyl-11,28-dioxa-4-azatricyclo-[22.3.1.0$^{4,9}$]-octacos-18-ene-2,3,10,16-tetraone To a solution of tri-(6-methoxy-2-naphthyl) bismuth diacetate (22 mg, 0.028 mmol, 1 eq) in methylene chloride (2 ml) in a 10 mL round bottom flask equipped with a stir bar was added 17-ethyl-1,14-dihydroxy-12-[2'-(3'',4''-dihydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (22 mg, 0.028 mmol, 1 eq). To the reaction mixture was added a catalytic amount of $Cu(OAc)_2$ (approximately 20 mg). The reaction flask was fitted with a reflux condenser and the mixture was warmed to 40° C. After 1 hour the mixture was cooled, diluted with saturated aqueous $NaHCO_3$ and extracted 4 times with $CH_2Cl_2$. The organic extracts were combined, dried over anhydrous $Na_2SO_4$, filtered and concentrated in vacuo. The product was isolated by preparative thin layer chromatography on silica gel (eluted with 2:1 hexanes/acetone) to give 7.1 mg of 17-ethyl-1,14-dihydroxy-12-[2'-(4''-(6'''-methoxynaphth-2-yloxy)-3''-h ydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,-10,16-tetraone ($R_f$=0.35) and 9 mg of 17-ethyl-1,14-dihydroxy-12-[2'-(3''-(6'''-methoxy-naphth-2-y loxy)-4''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone ($R_f$=0.28). ($^1$H NMR and mass spectral analysis were consistent with the desired structures).

EXAMPLE 16

17-Ethyl-1,14-dihydroxy-12-[2'-(4''-(4'''-methoxyp henyloxy)-3''-methoxycyclohexyl)-1''-methylvinyl]-23,25-dimethoxy-13,19,21,27-tetramethyl-11,28-dioxa-4-aza-tricyclo[22.3.1.0$^{4,9}$]octacos-18-ene-2,3,10,16-tetraone To a stirred solution of tris(4-methoxyphenyl)bismuthine (200 mg, 0.377 mmol) in $CH_2Cl_2$ (4 mL) was added bis(trifluoroacetoxy)iodobenzene (162 mg, 0.377 mmol). The mixture was stirred 5 minutes, then passed through a silica gel plug and eluted with EtOAc. The eluant was concentrated in vacuo. The residue was dissolved in $CH_2Cl_2$ (4 mL) in a 50 mL round bottom flask equipped with a magnetic stir bar. To this stirred mixture was added 17-ethyl-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (132 mg, 0.167 mmol) and $Cu(OAc)_2$ (10 mg 0.055 mmol). The flask was capped and the mixture stirred 48 hours. The reaction was quenched by addition of saturated aqueous $NaHCO_3$ and extracted 44× with $CH_2Cl_2$. The organic extracts were combined and dried over anhydrous $Na_2SO_4$. The mixture was filtered and concentrated in vacuo. The products were isolated by preparative TLC on silica gel (2:1 hexanes/acetone) to afford 26.8 mg of 17-ethyl-1,14-dihydroxy-12-[2'-(4''-(4'''-methoxyphenyloxy)-3''-methoxycyclohexyl)-1'-methylvinyl]-23,25-dimethoxy-13,19,21,27-tetramethyl-11,28-dioxa- 4-azatricyclo[22.3.1.0$^{4,9}$]octacos-18-ene-2,3,10,16-tetraone ($R_f$=0.35). ($^1$H NMR and mass spectral analysis were consistent with the desired structure).

EXAMPLE 17

17-Ethyl-1,14-dihydroxy-12-[2'-(4''-(3'''-methoxy phenyloxy)-3''-methoxycyclohexyl)-1''-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a stirred solution of tris(3-methoxyphenyl)bismuthine (200 mg, 0.377 mmol) in $CH_2Cl_2$ (3 mL) was added bis(trifluoroacetoxy)iodobenzene (162 mg, 0.377 mmol). The mixture was stirred 5 minutes, then passed through a silica gel plug and eluted with EtOAc. The eluant was concentrated in vacuo. The residue was dissolved in $CH_2Cl_2$ (4 mL) in a 50 mL round bottom flask equipped with a magnetic stir bar. To this stirred mixture was added 17-ethyl-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (112 mg, 0.141 mmol) and $Cu(OAc)_2$ (10 mg 0.055 mmol). The flask was capped and the mixture stirred 48 hours. The reaction was quenched by addition of saturated aqueous $NaHCO_3$ and extracted 44× with $CH_2Cl_2$. The organic extracts were combined and dried over anhydrous $Na_2SO_4$. The mixture was filtered and concentrated in vacuo. The products were isolated by radjal chromatography on silica gel (2 mm plate eluted with 3:1 hexanes/acetone) and then by preparative TLC on silica gel (eluted with 2:1 hexanes/acetone) to afford 78.4 mg of 17-ethyl-1,14-dihydroxy-12-[2'-(4''-(3'''-methoxyphenyloxy)-3''-methoxycyclohexyl)-1'-methylvinyl]-23,25-dimethoxy-13,19,21,27-tetramethyl-11,28-dioxa-4-azatricyclo-[22.3.1.0$^{4,9}$ octacos-18-ene-2,3,10,16-tetraone ($R_f$=0.40). ($^1$H NMR and mass spectral analysis were consistent with the desired structure).

EXAMPLE 18

17-Ethyl-1,4-dihydroxy-12-[2'-(4"-(6'''-tert-butyldimethylsilyloxynaphth-2-yloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone To a stirred solution of tris(6-tert-butyldimethylsilyloxynaphth-2-yl)bismuthine (100 mg, 0.215 mmol) in CH$_2$Cl$_2$ (4 mL) was added peracetic acid (0.05 mL, 0.238 mmol, 32 wt % in dilute acetic acid). To this stirred solution was added THF (1 mL), 17-ethyl-1,1-4-dihydroxy-12-[2'-(4"-hydroxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (100 mg, 0.126 mmol) and Cu(OAc)$_2$ (catalytic amount). The flask was fitted with a reflux condenser and the mixture was heated to 40° C. for 2 hours. The mixture was allowed to cool and was stirred 72 hours. The reaction was quenched with saturated aqueous NaHCO$_3$ and extracted 4× with CH$_2$Cl$_2$. The organic extracts were combined and dried over anhydrous Na$_2$SO$_4$. The mixture was filtered and concentrated in vacuo. The products were isolated by preparative TLC on silica gel (eluted with 2:1 hexanes/acetone) to afford 47 mg of 17-ethyl-1,14-dihydroxy-12-[2'-(4"-(6'''-tert-butyl-dimethylsilyloxynaphth-2-yloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone ($R_f$=0.56). ($^1$H NMR and mass spectral analysis were consistent with the desired structure).

EXAMPLE 19

17-Ethyl-1,14-dihydroxy-12-[2'-(4"-(6'''-hydroxynaphth-2-yloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone To a stirred solution of 17-ethyl-1,14-dihydroxy-12-[2'-(4"-(6'''-tert-butyldimethylsilyloxynaphth-2-yloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (73 mg, 0.07 mmol) in CH$_2$Cl$_2$ (2 mL) was added a solution of p-toluenesulfonic acid in methanol (2 mL, 10% solution). The flask was capped and the mixture stirred 4 hours. The reaction was quenched with saturated aqueous NaHCO$_3$ and extracted 4× with CH$_2$Cl$_2$. The organic extracts were combined and dried over anhydrous Na$_2$SO$_4$. The mixture was filtered and concentrated in vacuo. The product was isolated by preparative TLC on silica gel (eluted with 2:1 hexanes/acetone) to afford 44.2 mg of 17-ethyl-1,14-dihydroxy-12-[2'-(4"-(6'''-hydroxynaphth-4-yloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone ($R_f$=0.23). ($^1$H NMR and mass spectral analysis were consistent with the desired structure).

EXAMPLE 20

17-Ethyl-1,14-dihydroxy-12-[2'-(4"-(4'''-tert-butyldimethylsilyloxyphenyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone To a stirred solution of tris(4-tert-butyldimethylsilyloxyphenyl)bismuthine (187 mg, 0.252 mmol) in CH$_2$Cl$_2$ (4 mL) was added peracetic acid (0.053 mL, 0.252 mmol, 32 wt % solution in dilute acetic acid). To this stirred solution was added 17-ethyl-1,14-dihydroxy-12-[2'-(4"-hydroxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (100 mg, 0.126 mmol), CU(OAc)$_2$ (8.5 mg, 0.046 mmol), and tetrahydrofuran (0.5 mL.). After stirring 48 hours the reaction mixture was quenched with saturated aqueous NaHCO$_3$ and extracted 4× with CH$_2$Cl$_2$. The organic extracts were combined and dried over anhydrous Na$_2$SO$_4$. The mixture was filtered and concentrated in vacuo. The products were isolated by preparative TLC on silica gel (eluted with 2:1 hexanes/acetone) to afford 81 mg of 17-ethyl-1,14-dihydroxy-12-[2'-(4"-(4'''-tert-buytl-dimethylsilyloxyphenyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ne-2,3,10,16-tetraone ($R_f$=0.49). ($^1$H NMR and mass spectral analysis were consistent with the desired structure).

EXAMPLE 21

17-Ethyl-1,14-dihydroxy-12-[2'-(4"-(4'''-hydroxyphenyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone To a stirred solution of 17-ethyl-1,14-dihydroxy-12-[2'-(4"-(4'''-tert-butyldimethylsilyloxynaphth-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (74.8 mg, 0.075 mmol) in CH$_2$Cl$_2$ was added a solution of p-toluenesulfonic acid in methanol (2 mL, 10% p-TsOH on methanol). The mixture was stirred 4 hours. The reaction mixture was quenched with saturated aqueous NaHCO$_3$ and extracted 4× with CH$_2$Cl$_2$. The organic extracts were combined and dried over anhydrous Na$_2$SO$_4$. The mixture was filtered and concentrated in vacuo. The products were isolated by preparative TLC on silica gel (eluted with 2:1 hexanes/acetone) to afford 52 mg of 17-ethyl-1,14-dihydroxy-12-[2'-(4"-(4'''-hydroxyphenyloxy)-3"-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone ($R_f$=0.25). ($^1$H NMR and mass spectral analysis were consistent with the desired structure).

EXAMPLE 22

17-Ethyl-1,14-dihydroxy-12-[2'-(4"-(4'''-methylthiophenyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a stirred solution of tris(4-methylthiophenyl)bismuthine (146 mg, 0.252 mmol) in CH$_2$Cl$_2$ was added peracetic acid (0.106 mL, 0.504 mmol). To this solution was added 17-ethyl-1,14-diydroxy-12-[2'-(4"-hydroxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (100 mg, 0.126 mmol), Cu(OAc)$_2$ (1 mg, 0.061 mmol), and tetrahydrofuran (0.5 mL). The mixture was stirred for 96 hours. The reaction mixture was quenched with saturated aqueous NaHCO$_3$ and extracted 4× with CH$_2$Cl$_2$. The organic extracts were combined and dried over anhydrous Na$_2$SO$_4$. The mixture was filtered and concentrated in vacuo. The products were isolated by preparative TLC on silica gel (eluted with 2:1 hexanes/acetone) to afford 15.5 mg of 17-ethyl--1,14-dihydroxy-12-[2'-(4"-(4'''-methylthiopheny loxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (R$_f$=0.47). ($^1$H NMR and mass spectral were analysis consistent with the desired structure).

EXAMPLE 23

17-Ethyl-1,14-dihydroxy-12-[2'-(4"-(2'''-me thylphenyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a stirred solution of tris(2-methylphenyl)bismuthine (50 mg, 0.014 mmol) in CH$_2$Cl$_2$ (2 mL) was added bis(trifluoroacetoxy)iodobenzene (45 mg, 0.104 mmol). To this stirred solution was added 17-ethyl-1,14-dihydroxy-12-[2'-(4"-hydroxy-3"-methoxycyclohexyl)-1'-methylvinyl]-23,25-dimethoxy-13,19,21,27-tetramethyl-11,28-dioxa-4-azatricyclo [22.3.1.0$^{4,9}$]octacos-18-ene-2,3,10,16-tetraone (82 mg, 0.104 mmol), Cu(OAc)$_2$ (catalytic), and acetic acid (0.060 mL, 0.104 mmol). The flask was fitted with a reflux condenser and the mixture warmed to 40° C. and stirred overnight. The reaction mixture was cooled and diluted with CH$_2$Cl$_2$. The reaction mixture was quenched with saturated aqueous NaHCO$_3$ and extracted 4× with CH$_2$Cl$_2$. The organic extracts were combined and dried over anhydrous Na$_2$SO$_4$. The mixture was filtered and concentrated in vacuo. The products were isolated by preparative TLC on silica gel (eluted with 2:1 hexanes/acetone) to afford 23.8 mg of 17-ethyl-1,14-dihydroxy-12-[2'-(4"(2'''--methylphenyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (R$_f$=0.46). ($^1$H NMR and mass spectral analysis were consistent with the desired structure).

EXAMPLE 24

17-Ethyl-1,14-dihydroxy-12-[2'-(4"-(3'''-methy lphenyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a stirred solution of tris(3-methylphenyl)bismuthine (189 mg, 0.392 mmol) in CH$_2$Cl$_2$ (3 mL) was added bis(trifluoroacetoxy)iodobenzene (168 mg, 0.392 mmol). To this stirred solution was added 17-ethyl-1,14--dihydroxy-12-[2'-(4"-hydroxy-3"-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone (150 mg, 0.189 mmol) and Cu(OAc)$_2$ (catalytic). The flask was capped and the mixture stirred overnight. The reaction mixture was quenched with saturated aqueous NaHCO$_3$ and extracted 4× with CH$_2$Cl$_2$. The organic extracts were combined and dried over anhydrous Na$_2$SO$_4$. The mixture was filtered and concentrated in vacuo. The products were isolated by radial chromatography on silica gel (eluted with 3:1 hexanes/ethyl acetate) to afford 70.9 mg of 17-ethyl-1,14-dihydroxy-12-[2'-(4"-(3'''-methylphenyloxy)-3"-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone. ($^1$H NMR and mass spectral analysis were consistent with the desired structure).

EXAMPLE 25

17-Ethyl-1,14-dihydroxy-12-[2'-(4"-(3''',4'''-dimethylphenyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a stirred solution of tris(3,4-dimethylphenyl)bismuthine (200 mg, 0.381 mmol) in CH$_2$Cl$_2$ (3 mL.) was added bis(trifluoroacetoxy)iodobenzene (165 mg, 0.383 mmol). One mL of this solution was transferred to a 10 mL flask. To this solution was added 17-ethyl-1,14--dihydroxy-12-[2'-(4"-hydroxy-3"-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone (100 mg, 0.128 mmol) and Cu(OAc)$_2$ (catalytic). The mixture was stirred overnight. The reaction mixture was quenced with saturated aqueous NaHCO$_3$ and extracted 4× with CH$_2$Cl$_2$. The organic extracts were combined and dried over anhydrous Na$_2$SO$_4$. The mixture was filtered and concentrated in vacuo. The products were isolated by radial chromatography on silica gel (eluted with 3.5% methanol/CH$_2$Cl$_2$) and then purified by preparative TLC on silica gel (eluted with 3:1 hexanes/acetone) to afford 24.3 mg of 17-ethyl-1,14-dihydroxy-12-[2'-(4"-(3''',4'''-dimethylphenylo xy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone. ($^1$H NMR and mass spectral analysis were consistent with the desired structure).

EXAMPLE 26

A.

17-Ethyl-1,14-dihydroxy-12-[2'-(3"-(4'''-metho xyphenyloxy)-4"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone and

B.

17-Ethyl-1,14-dihydroxy-12-[2'-(4"-(4'''-metho xyphenyloxy)-3"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a stirred solution of tri(4-methoxyphenyl)bismuthine (136 mg., 0.257 mmol., 2 eq.) in methylene chloride (4 mL.) was added peracetic acid (0.054 mL., 0.257 mmol., 2 eq., 32% solution in dilute acetic acid). To this stirred solution was added b 17-ethyl-1,14-d ihydroxy-12-[2'-(3",4"-dihydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene- 2,3,10,16-tetraone (100 mg., 0.126 mmol., 1 eq.), THF (0.5 mL.), and copper (II) acetate (7 mg., 0.038 mmol., 0.3 eq). The mixture was allowed to stir for 7 days. The reaction was quenched with saturated aqueous NaCl plus 2 drops 2N HCl and extracted 4× with methylene chloride. The organic extracts were combined, dried over anhydrous Na$_2$SO$_4$, filtered, and concnetrated in vacuo. The products were separated by preparative TLC on silica gel (2:1 hexanes/acetone). Each compound was repurified 2× by preparative TLC on silica gel (3:1 hexanes/acetone then 3.5% MeOH/CH$_2$Cl$_2$) affording 23.4 mg of 17-ethyl-1,14-dihydroxy-12-[2'-(4''-(4'''-methoxypheny loxy)-3''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone and 28.4 mg of 17-ethyl-1,14-dihydroxy-12-[2'-(3''-(4'''-methoxyphenyloxy)-4''-hydroxycyclohexyl)-1'-methylvinyl]-23,25-dimethoxy-13,19,21,27-tetramethyl-11,28-dioxa-4-azatricyclo [22.3.1.0$^{4,9}$]octacos-18-ene-2,3,10,16-tetraone. ($^1$H NMR and mass spectral analysis were consistent with the desired structures).

EXAMPLE 27

A.

17-Ethyl-1,14-dihydroxy-12-[2'(3''-(3'''-methoxyphenyloxy)-4''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone and

B.

17-Ethyl-1,14-dihydroxy-12-[2'-(4''-(3'''-methoxyphenyloxy)-3''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a stirred solution of tri(3-methoxyphenyl)bismuthine (136 mg., 0.257 mmol., 2 eq.) in methylene chloride (4 mL.) was added peracetic acid (0.054 mL., 2 eq., 32% solution in dilute acetic acid). To this stirred solution was added 17-ethyl-1,14-dihydroxy-12-[2'-(3'',4'-'-dihydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (100 mg., 0.126 mmol., 1 eq.), THF (0.5 mL.), and copper (II) acetate (7 mg., 0.038 mmol., 0.3 eq.). The mixture was allowed to stir for 7 days. The reaction was quenched with saturated aqueous NaCl plus 2 drops 2N HCl and extracted 4× with methylene chloride. The organic extracts were combined, dried over anhydrous Na$_2$SO$_4$, filtered, and concentrated in vacuo. The products were separated by preparative TLC on silica gel (2:1 hexanes/acetone). Each compound was repurified 2× by preparative TLC on silica gel (2:1 hexanes/acetone then 3.5% MeOH/CH$_2$Cl$_2$) affording 27 mg of 17-ethyl-1,14-dihydroxy-12-[2'-(4''-(3'''-methoxyphenyloxy)-3''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone and 35 mg of 17-ethyl-1,14-dihydroxy-12-[2'-[3''-(3'''-methoxyphenyloxy)-4''-hydroxycyclohexyl)-1'-methylvinyl]-23,25-dimethoxy- 13,19,21,27-tetramethyl-11,28-dioxa-4-azatricyclo [22.3.1.0$^{4,9}$]octacos-18-ene-2,3,10,16-tetraone. ($^1$H NMR and mass spectral analysis were consistent with the desired structures).

EXAMPLE 28

A.

17-Ethyl-1,14-dihydroxy-12-[2'-(3''-(4'''-tertbutyldimethylsilyloxyphenyloxy)-4''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone and

B.

17-Ethyl-1,14-dihydroxy-12-[2'-(4''-(4'''-tertbutyldimethylsilyloxyphenyloxy)-3''-hydroxycyclohexyl)-1'-methylvinyl]-23,25-dimethyoxy-13,19,21,27-tetramethyl-11,28-dioxa-4-azatricyclo[22.3.1.0$^{4,9}$]octacos-19-ene-2,3,10,16-tetraone To a stirred solution of tri(4-tert-butyldimethylsilyloxyphenyl)bismuthine (213 mg., 0.257 mmol., 2 eq.) in methylene chloride (4 mL.) was added peracetic acid (0.054 mL., 0.257 mmol., 2 eq. 32% solution in dilute acetic acid). To this stirred solution was added 17-ethyl-1,14-dihydroxy-12-[2'-(3'',4''-dihydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (100 mg., 0.126 mmol., 1 eq.), THF (0.5 mL.), and copper (II) acetate (7 mg., 0.038 mmol., 0.3 eq.). The mixture was allowed to stir for 7 days. The reaction was quenched with saturated aqueous NaCl plus 2 drops 2N HCl and extracted 4× with methylene chloride. The organic extracts were combined, dried over anhydrous Na$_2$SO$_4$, filtered, and concentrated in vacuo. The products were separated by preparative TLC on silica gel (2:1 hexanes/acetone) affording 41.9 mg. of 17-ethyl-1,14-dihydroxy-12-[2'-(4''(4'''-tert-butyldimethylsilyloxyphenyloxy)-3''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone and 42.5 mg. of 17-ethyl-1,14-dihydroxy-12-[2'-(3''-(4'''-tert-butyldimethylsilyloxyphenyloxy)-4''-hydroxycylohexyl)-1'-methylvinyl]-23,25-dimethoxy-13,19,21,27-tetramethyl-11,28-dioxa-4-azatricyclo [22.3.1.0$^{4,9}$]octacos-18-ene-2,3,10,16-tetraone. ($^1$H NMR and mass spectral analysis were consistent with the desired structures).

EXAMPLE 29

17-Ethyl-1,14-dihydroxy-12-[2'-(3''-(4'''-hydroxyphenyloxy)-4''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a stirred solution of 17-ethyl-1,14-dihydroxy-1-2-[2'-(3''-(4'''-tert-butyldimethylsilyloxyphenyloxy)-4''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (42.5 mg) in CH$_2$Cl$_2$ (1.5 mL.) at 0° C. was added a solution of p-toluenesulfonic acid in methanol (1.5 mL. of a 10% w/v solution). The mixture was stirred 3H at 0° C. and then 3H at room temperature. The reaction mixture was quenched with saturated aqueous NaHCO$_3$ and extracted 4× with CH$_2$Cl$_2$. The organic extracts were combined and dried over anhydrous Na$_2$SO$_4$. The mixture was filtered and concentrated in vacuo. The product was isolated by preparative TLC on silica gel (eluted with 2:1 hexanes/acetone) affording 25.7 mg of 17-ethyl-1,14-dihydroxy-12-[2'-(3''-(4'''-hydroxyphenyloxy)-4''-hydroxycyclohexyl)-1'-methylvinyl]23,25-dimethoxy-13,19,21,27-tetramethyl-11,28-dioxa-4-azatricyclo[22.3.1.0^4,9]octacos-18-ene-2,3,10,16-tetraone. (^1H NMR and mass spectral anaylsis were consistent with the desired structure).

EXAMPLE 30

17-Ethyl-1,14-dihydroxy-12-[2'-(4''-(4'''-hydroxyphenyloxy)-3''-hydroxycyclohexyl)-1'-methylvinyl]-23,25-dimethoxy-13,19,21,27-tetramethyl-11,28-dioxa-4-azatricyclo[22.3.1.0^4,9]octacos-18-ene-2,3,10,16-tetraone To a stirred solution of 17-ethyl-1,14-dihydroxy-1-2-[2'-(4''-(4'''-tert-butyldimethylsilyloxyphenyloxy)-3''-hydroxycyclohexyl)-1'-methylvinyl]-23,25-dimethoxy-13,19,21,27-tetramethyl-11,28-dioxa-4-azatricyclo[22.3.1.0^4,9]octacos-18-ene-2,3,10,16-tetraone (41.9 mg) in CH$_2$Cl$_2$ (1.5 mL.) at 0° C. was added a solution of p-toluenesulfonic acid in methanol (1.5 mL. of a 10% w/v solution). The mixture was stirred 3H at 0° C. and then 3H at room temperature. The reaction mixture was quenched with saturated aqueous NaHCO$_3$ and extracted 4× with CH$_2$Cl$_2$. The organic extracts were combined and dried over anhydrous Na$_2$SO$_4$. The mixture was filtered and concentrated in vacuo. The product was isolated by preparative TLC on silica gel (eluted with 2:1 hexane/acetone) affording 23.9 mg of 17-ethyl-1,14-dihydroxy-12-[2'-(4''-(4'''-hydroxyphenyloxy)-3''-hydroxycyclohexyl)-1'-methylvinyl]-23,25-dimethoxy-13,19,21,27-tetramethyl-11,28-dioxa-4-azatricyclo[22.3.1.0^4,9]octacos-18-ene-2,3,10,16-tetraone. (^1H NMR and mass spectral analysis are consistent with the desired structure).

EXAMPLE 31

A.
17-ethyl-1,14-dihydroxy-12-[2'-(3''-(6'''-tert-butyldimethylsilyloxynaphth-2-yloxy)-4''-hydroxycyclohexyl)-1'-methylvinyl]-23,25-dimethoxy-13,19,21,27-tetramethyl-11,28-dioxa-4-azatricyclo[22.3.1.0^4,9]octacos-18-ene-2,3,10,16-tetraone and 17-Ethyl-1,14-dihydroxy-12-[2'-(4''-(6'''-tert-butyldimethylsilyloxy-naphth-2-yloxy)-3''-hydroxycyclohexyl)-1'-methylvinyl]methylvinyl]-23,25-dimethoxy-13,19,21,27-tetramethyl-11,28-dioxa-4-azatricyclo-[22.3.1.0^4,9]octacos-18-ene-2.3.10.16-tetraone To a stirred solution of tri(6-tert-butyldimethylsilyloxynaphth-2-yl)bismuthine (252 mg., 0.257 mmol., 2 eq.) in methylene chloride (4 mL.) was added peracetic acid (0.054 mL., 0.257 mmol., 2 eq., 32% solution in dilute acetic acid). To this stirred solution was added 17-ethyl-1,14-dihydroxy-12-[2'-( 3'',4''-dihydroxycyclohexyl)-1'-methylvinyl]-23,25-dimethoxy-13,19,21,27-tetramethyl-11,28-dioxa-4-azatricyclo[22.3.1.0^4,9]octacos-18-ene-2,3,10,16-tetraone (100 mg., 0.126 mmol., 1 eq.), THF (0.5 mL.), and copper (II) acetate (7 mg., 0.038 mmol., 0.3 eq.). The mixture was allowed to stir for 7 days. The reaction was quenched with saturated aqueous NaCl plus 2 drops 2N HCl and extracted 4× with methylene chloride. The organic extracts were combined, dried over anhydrous Na$_2$SO$_4$, filtered, and concentrated in vacuo. The products were separated by preparative TLC on silica gel (2:1 hexanes/acetone) affording 39.8 mg. of 17-ethyl-1,14-dihydroxy-12-[2'--(4''-(6'''-tert-butyldimethylsilyloxynaphth-2-yloxy)-3''-hydroxycyclohexyl)-1'-methylvinyl]-23,25-dimethoxy-13,19,21,27-tetramethyl-11,28-dioxa-4-azatricyclo[22.3.1.0^4,9]octacos-18-ene-2,3,10,16-tetraone and 41.6 mg. of 17-ethyl-1,14-dihydroxy-12-[2'-(3''-(6'''-tert-butyldimethylsilyloxynaphth-2-yloxy)-4''-hydroxycylohexyl)-1'-methylvinyl]-23,25-dimethoxy-13,19,21,27-tetramethyl-11,28-dioxa-4-azatricyclo[22.3.1.0^4,9]octacos-18-ene-2,3,10,16-tetraone. (^1H NMR and mass spectral analysis were consistent with the desired structures).

EXAMPLE 32

17-Ethyl-1,14-dihydroxy-12-[2'-(4''-(6'''-hydroxynaphth-2-yloxy)-3''-hydroxycyclohexyl)-1'-methylvinyl]-23,25-dimethoxy-13,19,21,27-tetramethyl-11,28-dioxa-4-azatricyclo[22.3.1.0^4,9]octacos-18-ene-2,3,10,16-tetraone To a stirred solution of 17-ethyl-1,14-dihydroxy-12-[2'-(4''-(6'''-tert-butyldimethylsilyloxynaphth-2-yloxy)-3''-hydroxycyclohexyl)-1'-methylvinyl]-23,25-dimethoxy-13,19,21,27-tetramethyl-11,28-dioxa-4-azatricyclo[22.3.1.0^4,9]octacos-18-ene-2,3,10,16-tetraone (39.8 mg) in CH$_2$Cl$_2$ (1.5 mL.), at 0° C. was added a solution of p-toluenesulfonic acid in methanol (1,5 mL. of a 10% w/v solution). The mixture was stirred 1.25 h at 0° C. and then 1.75 h at room temperature. The reaction mixture was quenched with saturated aqueous NaHCO$_3$ and extracted 4× with CH$_2$Cl$_2$. The organic extracts were combined and dried over anhydrous Na$_2$SO$_4$. The mixture was filtered and concentrated in vacuo. The product was isolated by preparative TLC on silica gel (eluted 2× with 2:1 hexanes/acetone) affording 17 mg of 17-ethyl-1,14-dihydroxy-12-[2'-(4''-(6'''-hydroxynaphth-2-yloxy)-3''-hydroxycyclohexyl)-1'-methylvinyl]-23,25-dimethoxy-13,19,21,27-tetramethyl-11,28-dioxa-4-azatricyclo[22.3.1.0^4,9]octacos-18-ene-2,3,10,16-tetraone. (^1H NMR and mass spectral analysis were consistent with the desired structure).

EXAMPLE 33

17-Ethyl-1,14-dihydroxy-12-[2'-(3''-(6'''-hydroxynaphth-2-yloxy)-4''-hydroxycyclohexyl)-1'-methylvinyl]-23,25-dimethoxy-13,19,21,27-tetramethyl-11,28-dioxa-4-azatricyclo[22.3.1.0^4,9]octacos-18-ene-2,3,10,16-tetraone To a stirred solution of 17-ethyl-1,14-dihydroxy-12-[2'-(3''-(6'''-tert-butyldimethylsilyloxynaphth-2-yloxy)-4''-hydroxycyclohexyl)-1'-methylvinyl]-23,25-dimethoxy-13,19,21,27-tetramethyl-11,28-dioxa-4-azatricyclo[22.3.1.0^4,9]octacos-18-ene-2,3,10,16-tetraone (41.6 mg) in CH$_2$Cl$_2$ (1.5 mL.) at 0° C. was added a solution of p-toluenesulfonic acid in methanol (1.5 mL. of a 10% w/v solution). The mixture was stirred 1.25 h at 0° C. and then 1.75 h at room temperature. The reaction mixture was quenched with saturated aqueous NaHCO$_3$ and extracted 4× with CH$_2$Cl$_2$. The organic extracts were combined and dried over anhydrous Na$_2$SO$_4$. The mixture was filtered and concentrated in vacuo. The product was isolated by preparative TLC on silica gel (eluted 2× with 2:1 hexanes/acetone) affording 20.8 mg of 17-ethyl-1,14-dihydroxy-12-[2'-(3''-(6'''-hydroxynaphth-2-yloxy)-4''-hydroxycyclohexyl)-1'-methylvinyl]23,25-dimethoxy-13,19,21,27-tetramethyl-11,28-dioxa-4-azatricyclo[22.3.1.0^4,9]octacos-18-ene-2,3,10,16-tetraone. (^1H NMR and mass spectral analysis were consistent with the desired structure).

EXAMPLE 34

17-Ethyl-1,14-dihydroxy-12-[2-(4''-(ethoxycarbomethoxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a stirred solution of 17-ethyl-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (200 mg., 0.253 mmol., 1 eq.) in diethyl ether (6 mL.) was added boron trifluoride etherate (0.009 mL., 0.073 mmol., 0.3 eq.) and ethyl diazoacetate (0.080 mL., 0.760 mmol., 3 eq.). The reaction mixture was stirred 12 h. The reaction mixture was quenched with saturated aqueous NaHCO₃ and extracted 4× with CH₂Cl₂. The organic extracts were combined and dried over anhydrous Na₂SO₄. The mixture was filtered and concentrated in vacuo. The products were isolated by preparative TLC on silica gel (3:2 EtOAc/hexanes) and a second preparative TLC (eluted 2× with 3:1 hexanes/acetone) affording 24.7 mg of 17-ethyl-1,14-dihydroxy-12-[2'-(4''-(ethoxycarbomethoxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone. ($^1$H NMR, $^{13}$C NMR and mass spectral analysis were consistent with the desired structure).

EXAMPLE 35

17-Ethyl-1,14-dihydroxy-12-[2'-(4''-(3''',4'''-dichlorophenyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a stirred solution of tri(3,4-dichlorophenyl)bismuthine (163 mg., 0.25 mmol.) in CH₂Cl₂ (2 mL.) was added bis(trifluoroacetoxy)iodobenzene (107 mg., 0.25 mmol.). The mixture was stirred for 15 minutes then treated with Cu(OAc)₂ followed by a solution of 17-ethyl-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (100 mg., 0.126 mmol.) in CH₂Cl₂ (2 mL.). After stirring an additional 2 hours the reaction mixture was quenched by addition of saturated aqueous NaHCO₃ and extracted 2× with CH₂Cl₂. The organic extracts were combined, dried over anhydrous Na₂SO₄, filtered, and concentrated in vacuo. The product was separated and purified by preparative TLC on silica (eluted with 3:1 Hexane/Acetone) to give 51 mg 17-ethyl-1,14-dihydroxy-12-[2'-(4''-(3''',4'''-dichlorophenyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone ($^1$H NMR, $^{13}$H NMR, and mass spectral analysis are consistent with the desired structure).

EXAMPLE 36

17-Ethyl-1,14-dihydroxy-12-[2'-(4''-(phenanthr-9-yl)-3''-methoxycyclohexyl)-1'-methylvinyl]-23,25-dimethoxy-13,19,21,27-tetramethyl-11,28-dioxa-4-azatricyclo [22.3.1.0$^{4,9}$]octacos-18-ene-2,3,10,16-tetraone To a stirred solution on tri(9-phenanthryl)bismuthine (150 mg., 0.20 mmol) in CH₂Cl₂ (3 mL) was added peracetic acid (0.050 mL, 0.22 mmol, 32 wt. % solution in dilute acetic acid). After 15 minutes the solution was treated with 17-ethyl-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (100 mg, 0.126 mmol) and Cu(OAc)₂ (10 mg, 0.055 mmol) and stirred for 18 hours. The reaction mixture was quenched with saturated aqueous NaHCO₃ and extracted 3× with CH₂Cl₂. The extracts were combined, dried with Na₂SO₄, filtered and concentrated in vacuo. The product was isolated and purified by preparative TLC on silica gel (eluted with 2:1 hexane/acetone to give 12 mg of 17-ethyl-1,14-dihydroxy-12-[2'-(4''-(phenanthr-9-yl)-3''-methoxycyclohexyl)-1'-methylvinyl]-23,25-dimethoxy-13,19,21,27-tetramethyl-11,28-dioxa-4-azatricyclo [22.3.1.0$^{4,9}$ octacos-18-ene-2,3,10,16-tetraone ($^1$H NMR was consistent with the desired structure).

EXAMPLE 37

17-Ethyl-1,14-dihydroxy-12--[2'-(4''-(3''',4'''-methylenedioxyphenyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2.3.10.16-tetraone To a stirred solution of tri(3,4-methylenedioxyphenyl)bismuthine (150 mg., 0.26 mmol) in CH₂Cl₂ (2 mL) was added peracetic acid (0.060 mL, 0.26 mmol, 32 wt % solution in dilute acetic acid). After approximately 10 minutes the solution was treated with Cu(OAc)₂ (25 mg, 0.138 mmol) and 17-ethyl-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (100 mg, 0.126 mmol) and stirred for 18 hours. The reaction mixture was quenched with saturated aqueous NaHCO₃ and extracted 2× with CH₂Cl₂. The extracts were combined, dried with anhydrous Na₂SO₄, filtered, and concentrated in vacuo. The product was isolated and purified by preparative TLC on silica gel (eluted with 2:1 Hexane/Acetone) to give 37 mg of 17-ethyl-1,14-dihydroxy-12-[2'-(4''-(3'''-methylenedioxyphenyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone ($^1$H NMR and mass spectral analysis were consistent with the desired structure).

EXAMPLE 38

17-Ethyl-1,14-dihydroxy-12-[2'--(4''-(2''',3'''-dihydrobenzofuran-5-yl)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2.3.10.16-tetraone To a stirred solution of tri(2,3-dihydrobenzofuran-5-yl)bismuthine (32 mg, 0.056 mmol) in CH₂Cl₂ (1 mL) was added peracetic acid (0.020 mL, 0.09 mmol, 32 wt % solution in dilute acetic acid). After approximately 15 minutes the solution was treated with Cu(OAc)₂ (20 mg, 0.11 mmol) and 17-ethyl-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (50 mg, 0.06 mmol) and stirred for three days. The reaction mixture was quenched with saturated aqueous NaHCO₃ and extracted with CH₂Cl₂. The extracts were combined, dried with anhydrous Na₂SO₄, filtered and concentrated in vacuo. The product was purified by preparative TLC on silica gel (eluted with 2:1 Hexane/acetone) to give 14 mg of 17-ethyl-1,14-dihydroxy-12-[2'-(4''-(2''',3'''-dihydrobenzofuran-5-yl)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone characterized by ($^1$H NMR and mass spectral analysis were consistent with the desired structure).

EXAMPLE 39

17-Allyl-1,14-dihydroxy-12-[2'-(4''-(naphth-2-yl)-3''-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone A mixture of 17-allyl-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18ene-2,3,10,16-tetraone (400 mg, 0.5 mmol) and Cu(OAc)$_2$ (35 mg, 0.19 mmol) in CH$_2$Cl$_2$ (6 mL) was warmed to 40° C. for 15 minutes then treated with tri(2-naphthyl)bismuth diacetate [prepared immediately prior to use by addition of acetic acid (0.18 mL, 3 mmol) to a suspension of tri(2-naphthyl)bismuth carbonate (600 mg, 0.92 mmol) in CH$_2$Cl$_2$ (6 mL)]. Heating was maintained for 4 hours after which time the mixture was stirred at room temperature for 18 hours. The reaction mixture was quenched with saturated aqueous NaHCO$_3$ and extracted with CH$_2$Cl$_2$. The extracts were combined, dried with Na$_2$SO$_4$, filtered and concentrated in vacuo. The product was isolated and purified by preparative TLC on silica gel (eluted with 3:1 Hexane/Acetone) to give 234 mg of 17-allyl-1,14-dihydroxy-12-[2'-(4''-(naphth-2-yl)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18ene-2,3,10,16-tetraone ($^1$H NMR and mass spectral analysis were consistent with the desired structure).

EXAMPLE 40

17-Ethyl-1,14-dihydroxy-12-[2'-(4''-(1''',4'''-benzodioxane-6-yl)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a stirred solution of tris(1,4-benzodioxan-6-yl)bismuthine (90 mg, 0.146 mmol) in CH$_2$Cl$_2$ (1 mL) was added peracetic acid (0.030 mL, 0.13 mmol, 32 wt % in dilute acetic acid). After 20 minutes the mixture was treated with 17-ethyl-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (100 mg, 0.126 mmol) followed by Cu(OAc)$_2$ (15 mg, 0.08 mmol) and stirred for 2 days. The reaction mixture was quenched with saturated aqueous NaHCO$_3$ and extracted with CH$_2$Cl$_2$. The extracts were combined, dried with Na$_2$SO$_4$, filtered and concentrated in vacuo. The product was purified by preparative TLC on silica gel (eluted with 4% CH$_3$OH in CH$_2$Cl$_2$) to give 18 mg of 17-ethyl-1,14-dihydroxy-12-[2'-(4''-(1''',4'''-benzodioxane-6-yl)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone ($^1$H NMR and mass spectral analysis were consistent with the desired structure).

EXAMPLE 40B

17-Ethyl-1-hydroxy-12-[2'-(4'''-dimethylamino)phenyloxy-3''-hydroxycyclohexyl)-1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone (A) and 17-Ethyl-1-hydroxy-12-[2'-(4''-hydroxy-3''-(4'''-dimethylamino)phenyloxycyclohexyl)-1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone (B)

Peracetic acid (850 ml) was added to a solution of tri(4-dimethylaminophenyl)bismuthine (1.27 g) in 30 ml tetrahydrofuran. After 10 minutes 17-ethyl-1-hydroxy-12-[2'-(3'',4''-dihydroxycyclohexyl)-1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone (100 mg) was added followed by copper acetate (280 mg) and the mixture heated to 60° C. for 48 hours. The mixture was then cooled and quenched by pouring into saturated sodium bicarbonate, extracting with ether (3×25 ml). The combined organic washes were dried with magnesium sulphate and concentrated. The crude residue was purified by column chromatography on silica gel eluting with 70% hexane:30% ethyl acetate to give the title compounds A (93 mg) and B (102 mg) each as white solids.

EXAMPLE 41

17-Ethyl-1,2,14-trihydroxy-12-[2'-(4''-(naphth-2-yl)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-3,10,16-trione A solution of 1,2-diiodoethane (42 mg, 0.15 mmol) in dry THF (1 mL) was added dropwise to a stirred mixture of samarium metal (46.5 mg, 0.31 mmol) in dry THF (1 mL) and stirred for 1.5 hours. The reaction mixture was then cooled to −78° C. (dry ice/acetone) and treated with a solution of 17-ethyl- 1,14-dihydroxy-12-[2'-(4''-(naphth-2-yl)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (100 mg, 0.109 mmol) in 1:1 THF/CH$_3$OH. The mixture was maintained at −78° C. for 15 minutes then allowed to warm to room temperature. The reaction was quenched with cold saturated aqueous K$_2$CO$_3$ and quickly extracted with CH$_2$Cl$_2$. The extracts were combined, dried with Na$_2$SO$_4$, filtered and concentrated in vacuo. Purified by preparative TLC on silica gel (eluted with 7% CH$_3$OH in CH$_2$Cl$_2$) to give 22 mg of 17-ethyl-1,2,14-trihydroxy-12-[2'-(4''-(naphth-2-yl)-3''-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-3,10,16-trione ($^1$H NMR and mass spectral analysis are consistent with the desired structure).

EXAMPLE 42

17-Ethyl-1,14-dihydroxy-12-[2'-(4"-allyloxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1,14-dihydroxy-12-[2'-(4"-hydroxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (200 mg in 3.0 ml 33% methylene chloride in cyclohexane), allyl trichloroacetimidate (88 μl neat) was added and the reagents allowed to mix for 5 minutes. Trifluoromethanesulfonic acid (4.5 μl neat) was added slowly via syringe and the mixture stirred at room temperature. After 18 hours the reaction was quenched by the addition of saturated sodium bicarbonate and extracted with ethyl acetate (3×5 ml). The combined organics were washed with brine and dried over magnesium sulfate. Purification of the concentrate by flash chromatography on silica gel (ethyl acetate:hexane (1:2)+1% methanol) gave the title compound (156 mg).

MASS: (FAB) 838 (M+Li)

Partial $^1$H NMR δ: 5.82 (m, 1H); 4.85 (m), 4.20 (brs, 1H); 4.59 (brd J=4.5 Hz, 1H); 4.41 (brd J=14 Hz, 1H); 4.03 (dt J=4.0, 1.0 Hz, 2H).

EXAMPLE 43

17-Ethyl-1,14-dihydroxy-12-[2'-(4"-(2-butynyloxy)-3"-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone To a solution of 17-ethyl-1,14-dihydroxy-12-[2'-(4"-hydroxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (50 mg in 1.5 ml 33% methylene chloride in cyclohexane), 2-butynyl trichloroacetimidate (20 μl neat) was added and the reagents allowed to mix for 5 minutes. Trifluoromethanesulfonic acid (2 μl neat) was added slowly via syringe and the mixture stirred at room temperature. After 16 hours the reaction was quenched by the addition of saturated sodium bicarbonate and extracted with ethyl acetate (3×5 ml). The combined organics were washed with brine and dried over magnesium sulfate. Purification of the concentrate by preparative TLC on silica gel (ethyl acetate:hexane (1:1)+1% methanol) gave the title compound (17 mg).

MASS: (FAB) 843 (M+Na)

Partial $^1$H NMR δ: 5.32 (Major amide rotamer), 5.29 (minor amide rotamer) (brd J=3.0 Hz, 1H); 4.83m, 4.21M (brs, 1H); 4.59 (brd J=4.0 Hz, 1H); 4.42 (brd J=14.0 Hz, 1H); 4.26 (m, 2H); 1.83 (t J=2.0 Hz, 3H).

EXAMPLE 44

17-Ethyl-1,14-dihydroxy-12-[2'-(4"-cinnamyloxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1,14-dihydroxy-12-[2'-(4"-hydroxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (50 mg in 1.5 ml 33% methylene chloride in cyclohexane), cinnamyl trichloroacetimidate (26 μl neat) was added and the reagents allowed to mix for 5 minutes. Trifluoromethanesulfonic acid (2 μl neat) was added slowly via syringe and the mixture stirred at room temperature. After 15 minutes the reaction was quenched by the addition of saturated sodium bicarbonate and extracted with ethyl acetate (3×5 ml). The combined organics were washed with brine and dried over magnesium sulfate. Purification of the concentrate by preparative TLC on silica gel (ethyl acetate:hexane (1:1)+1% methanol) gave the title compound (10 mg).

MASS: (FAB) 907 (M+Na)

Partial $^1$H NMR δ: 6.62 (d J=15 Hz, 1H); 6.30 (dt J=15, 6.0 Hz, 1H); 5.33M, 5.19 m (brd J=3.0 Hz, 1H); 4.83m, 4.21M (brs, 1H); 4.58 (brd J=4.0 Hz, 1H); 4.41 (brd J=14 Hz, 1H); 4.30 (d J=6.0 Hz, 2H).

EXAMPLE 45

17-Ethyl-1,14-dihydroxy-12-[2'-(3"-methoxy-4"-phenylpropyloxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone To a solution of 17-ethyl-1,14-dihydroxy-12-[2'-(4"-cinnamyloxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (37 mg in 2 ml ethanol) was added 4 mg of 5% rhodium on carbon catalyst. The reaction flask was fitted with a hydrogen balloon, evacuated and recharged with hydrogen (3 times) and stirred at room temperature. After 1.5 hours, the mixture was filtered over Celite, concentrated and purified by preparative TLC on silica gel (ethyl acetate:hexane (1:2)+1% methanol) to give the title compound (19.5 mg).

MASS: (FAB) 932 (M+Na); 916 (M+Li)

Partial $^1$H NMR δ: 5.31M, 5.28m (d J=3.0 Hz, 1H); 4.85m, 4.21M (brs, 1H); 4.58 (brd J=4.0 Hz, 1H); 4.41 (brd J=14 Hz, 1H); 2.69 (t J=8.0 Hz, 2H).

EXAMPLE 46

A.

17-Ethyl-1,14-dihydroxy-12-[2'-(4"-allyloxy-3"-hydroxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone and

B.

17-Ethyl-1,14-dihydroxy-12-[2'-(3"-allyloxy-4"-hydroxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone To a solution of 17-ethyl-1,14-dihydroxy-12-[2'-(3",4"-dihydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (100 mg in 1.5 ml 33% methylene chloride in cyclohexane), allyl trichloroacetimidate (53 μl neat) was added and the reagents allowed to mix for 5 minutes. Trifluoromethanesulfonic acid (2 μl neat) was added slowly via syringe and the mixture stirred at room temperature. After 3 hours the reaction was quenched by the addition of saturated sodium bicarbonate and extracted with ethyl acetate (3×5 ml). The combined organics were washed with brine and dried over magnesium sulfate. Purification of the concentrate by flash chromatography on silica gel (ethyl acetate:hexane (1:1)+1% methanol) gave the title compounds (21 mg 4"-ether; 17 mg 3"-ether).

A. (4"-ether):

Partial $^1$H NMR δ: 5.93 (m, 1H); 4.87m, 4.19M (brs, 1H); 4.59 (brd J=4.0 Hz, 1H); 4.41 (brd J=14 Hz, 1H); 2.67 (brd J=3.7 Hz, 1H).

B. (3''-ether):
Partial $^1$H NMR δ: 5.93 (m, 1H); 4.83m, 4.23M (brs, 1H); 4.59 (brd J=4.0 Hz, 1H); 4.41 (brd J=14 Hz, 1H); 2.63 (brs, 1H).

EXAMPLE 47

A.
17-Ethyl-1,14-dihydroxy-12-[2'-(3''-hydroxy-4''-isopropoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone and B.
17-Ethyl-1,14-dihydroxy-12-[2'-(4''-hydroxy-3''-isopropoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone To a solution of 17-ethyl-1,14-dihydroxy-12-[2'-(3'',4''-dihydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (110 mg in 1.5 ml 33% methylene chloride in cyclohexane), isopropyl trichloroacetimidate (52 μl neat) was added and the reagents allowed to mix for 5 minutes. Trifluoromethanesulfonic acid (2 μl neat) was added slowly via syringe and the mixture stirred at room temperature. After 3 hours the reaction was quenched by the addition of saturated sodium bicarbonate and extracted with ethyl acetate (3×5 ml). The combined organic were washed with brine and dried over magnesium sulfate. Purification of the concentrate by preparative TLC on silica gel (ethyl acetate:hexane (1:1)+1% methanol) gave the title compounds (15 mg 4''-ether; 16 mg 3''-ether).

A. (4''-ether):
MASS: (FAB) 826 (M+Li)
Partial $^1$H NMR δ: 5.31 (d J=3.0 Hz, 1H); 4.85m, 4.18M (brs, 1H); 4.58 (brd J=4.0 Hz, 1H); 4.40 (brd J=14 Hz, 1H); 2.63 (brs, 1H).

B. (3''-ether):
MASS: (FAB) 826 (M+Li)
Partial $^1$H NMR δ: 5.31 (d J=3.0 Hz, 1H); 4.81m, 4.22M (brs, 1H); 4.58 (brd J=4.0 Hz, 1H); 4.40 (brd J=14 Hz, 1H); 2.60 (brs, 1H).

EXAMPLE 48

A.
17-Ethyl-1,14-dihydroxy-12-[2'-(4''-sec-butenyloxy-3''-hydroxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone and B.
17-Ethyl-1,14-dihydroxy-12-[2'-(3''-sec-butenyloxy-4''-hydroxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone To a solution of 17-ethyl-1,14-dihydroxy-12-[2'-(3'',4''-dihydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (150 mg in 3 ml 33% methylene chloride in cyclohexane), sec-butenyl trichloroacetimidate (62 μl neat) was added and the reagents allows to mix for 5 minutes. Trifluoromethanesulfonic acid (2 μl neat) was added slowly via syringe and the mixture stirred at room temperature. After 15 hours the reaction was quenched by the addition of saturated sodium bicarbonate and extracted with ethyl acetate (3×8 ml). The combined organic were washed with brine and dried over magnesium sulfate. Purification of the concentrate by preparative TLC on silica gel (ethyl acetate:hexane (1:1)+1% methanol) gave the title compounds (11 mg 4''-ether; 3''-ether).

A. (4''-ether):
MASS: (FAB) 831 (M+Na)
Partial $^1$H NMR δ: 5.65 (m, 1H); 4.58 (brd J=3.0 Hz, 1H); 4.87m, 4.18M (brs, 1H); 4.58 (brd J=4.0 Hz, 1H); 4.41 (brd J=14 Hz, 1H).

B. (3''-ether):
MASS: (FAB) 831 (M+Na)
Partial $^1$H NMR δ: 5.65 (m, 1H); 5.31 (brs, 1H); 4.82m, 4.22M (brs, 1H); 4.58 (brd J=4.0 Hz, 1H); 4.41 (brd J=14 Hz, 1H).

EXAMPLE 49

A.
17-Ethyl-1,14-dihydroxy-12-[2'-(4''-(trans-2'''-butenyloxy)-3''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone and B.
17-Ethyl-1,14-dihydroxy-12-[2'-(3''-(trans-2'''-butenyloxy)-4''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1,14-dihydroxy-12-[2'-(3'',4''-dihydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (115 mg in 3 ml 33% methylene chloride in cyclohexane), trans-2-butenyl trichloroacetimidate (48 μl neat) was added and the reagents allowed to mix for 5 minutes. Trifluoromethanesulfonic acid (2 μl neat) wad added slowly via syringe and the mixture stirred at room temperature. After 35 minutes the reaction was quenched by the addition of saturated sodium bicarbonate and extracted with ethyl acetate (3×8 ml). The combined organics were washed with brine and dried over magnesium sulfate. Purification of the concentrate by preparation TLC on silica gel (ethyl acetate:hexane (1:1)+1% methanol) gave the title compounds (14 mg 4''-ether; 12 mg 3''-ether).

A. (4''-ether):
MASS: (FAB) 831 (M+Na)
Partial $^1$H NMR δ: 5.65 (m, 1H); 5.31 (brd J=3.0 Hz, 1H); 4.86m, 4.19M (brs, 1H); 4.59 (brd J=4.0 Hz, 1H); 4.41 (brd J=14 Hz, 1H); 2.68 (brs, 1H).

B. (3''-ether):
MASS: (FAB) 831 (M+Na)
Partial $^1$H NMR δ: 5.65 (m, 1H); 5.30 (brs, 1H); 4.81m, 4.22M (brs, 1H); 4.59 (brd J=4.0 Hz, 1H); 4.41 (brd J=14 Hz, 1H); 2.64 (brs, 1H).

EXAMPLE 50

A.
17-Ethyl-1,14-dihydroxy-12-[2'-(3"-hydroxy-4"-(3"'-methyl-2-butenyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone and B.
17-Ethyl-1,14-dihydroxy-12-[2'-(4"-hydroxy-3"-(3"'-methyl-2-butenyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1,14-dihydroxy-12-[2'-(3",4"-dihydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (100 mg in 2 ml methylene chloride), 3-methyl-2-butenyl trichloroacetimidate (39 μl neat) was added and the reagents allowed to mix for 5 minutes. Camphorsulfonic acid (5 mg) was added and the mixture stirred at room temperature. After 21 hours the reaction was quenched by the addition of saturated sodium bicarbonate and extracted with ethyl acetate (3×8 ml). The combined organics were washed with brine and dried over magnesium sulfate. Purification of the concentrate by preparative TLC on silica gel (ethyl acetate:hexane (1:1)+1% methanol) gave the title compounds (24 mg 4"-ether; 21 mg 3"-ether).

A. (4"-ether):
MASS: (FAB) 845 (M+Na)
Partial $^1$H NMR δ: 4.87m, 4.19M (brs, 1H); 4.58 (brd J=4.0 Hz, 1H); 4.41 (brd J=14 Hz, 1H); 2.70 (brs, 1H); 1.75 (s, 3H); 1.67 (s, 3H).

B. (3"-ether):
MASS: (FAB) 845 (M+Na)
Partial $^1$H NMR δ: 4.82m, 4.23M (brs, 1H); 4.58 (brd J=4.0 Hz, 1H); 4.41 (brd J=14 Hz, 1H); 2.67 (brs, 1H); 1.75 (s, 3H); 1.67 (s, 3H).

EXAMPLE 51

A.
17-Ethyl-1,14-dihydroxy-12-[2-(3"-hydroxy-4"-(2"'-methylpropenyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone and B.
17-Ethyl-1,14-dihydroxy-12-[2-(4"-hydroxy-3"-(2"'-methylpropenyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1,14-dihydroxy-12-[2'-(3",4"-dihydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (200 mg in 3 ml 33% methylene chloride in cyclohexane), 2-methylpropenyl trichloroacetimidate (84 μl neat) was added and the reagents allowed to mix for 5 minutes. Trifluoromethanesulfonic acid (2 μl neat) was added slowly via syringe and the mixture stirred at room temperature. After 1 hour the reaction was quenched by the addition of saturated sodium bicarbonate and extracted with ethyl acetate (3×8 ml). The combined organics were washed with brine and dried over magnesium sulfate. Purification of the concentrate by preparative TLC on silica gel (ethyl acetate : hexane (1:1) + 1% methanol) gave the title compounds (34 mg 4"-ether; 24 mg 3"-ether).

A. (4"-ether):
MASS: (FAB) 831 (M+Na)
Partial $^1$H NMR δ: 5.32 (brs, 1H); 4.87 (brs, 1H); 4.59 (brs, 1H); 4.41 (brd J=14 Hz, 1H); 4.19M (brs, 1H); 2.60 (brs, 1H); 1.74 (s, 3H).

B. (3"-ether):
MASS: (FAB) 831 (M+Na)
Partial $^1$H NMR δ: 5.32 (brs, 1H); 4.87 (brs, 1H); 4.81 m, 4.23M (brs, 1H); 2.63 (brs, 1H); 1.74 (s, 3H).

EXAMPLE 52

17-Ethyl-1,14-dihydroxy-12-[2'-(3"-cinnamyloxy-4"-hydroxycyclohexyl)-1'-methylvinyl]-23,25-dimethoxy-13,19,21,27-tetramethyl-11,28-dioxa-4-azatricyclo-[22.31.0$^{4,9}$]octacos-18-ene-2,3,10,16-tetraone To a solution of 17-ethyl-1,14-dihydroxy-12-[2'-(3",4"-dihydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (100 mg in 3 ml 33% methylene chloride in cyclohexane), cinnamyl trichloroacetimidate (52 μl neat) was added and the reagents allowed to mix for 5 minutes. Trifluoromethanesulfonic acid (2 μl neat) was added slowly via syringe and the mixture stirred at room temperature. After 15 minutes the reaction was quenched by the addition of saturated sodium bicarbonate and extracted with ethyl acetate (3×8 ml). The combined organics were washed with brine and dried over magnesium sulfate. Purification of the concentrate by preparative TLC on silica gel (ethyl acetate:hexane (1:1)+1% methanol) gave the title compound (17 mg).
MASS: (FAB) 893 (M+Na)
Partial $^1$H NMR δ: 6.61 (d J=15 Hz, 1H); 6.28 (dt J=15, 6.0 Hz, 1H); 5.32 m, 5.19M (brd J=3.0 Hz); 4.82 m, 4.22M (brs,1H); 4.52 (brd J=4.0 Hz, 1H); 4.41 (brd J=14 Hz, 1H); 2.66 (brs, 1H).

EXAMPLE 53

17-Ethyl-1-hydroxy-12-[2'-(4"-hydroxy-3"-isopropoxycyclohexyl)-1'-methylviinyl]-23,25-dimethoxy-13,19,21,27-tetramethyl-11,28-dioxa-4-azaticyclo[22.3.1.0$^{4,9}$]octacos-18-ene-2,3,10,16-tetraone To a solution of 17-ethyl-1-hydroxy-12-[2'-(3",4'-'-dihydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (69 mg in 3 ml 33% methylene chloride in cyclohexane), isopropyl trichloroacetimidate (22 μl neat) was added and the reagents allowed to mix for 5 minutes. Trifluoromethanesulfonic acid (2 μl neat) was added slowly via syringe and the mixture stirred at room temperature. After 24 hours the reaction was quenched by the addition of saturated sodium bicarbonate and extracted with ethyl acetate (3×8 ml). The combined organics were washed with brine and dried over magnesium sulfate. Purification of the concentrate by preparative TLC on silica gel (ethyl acetate:hexane (1:1)+1% methanol) gave the title compound (12 mg).
MASS: (FAB) 803 (M+Li)
Partial $^1$H NMR δ: 4.87 (brd J=10 Hz, 1H); 4.56 (d J=4.0 Hz, 1H); 4.42 m, 4.33 M (brs, 1H); 2.61 (brs, 1H); 1.16 (d J=7.0 Hz, 6H).

EXAMPLE 54

A.
17-Ethyl-1,14-dihydroxy-12-[2'-(4"-sec-butenyloxy-3"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone and

B.
17-Ethyl-1,14-dihydroxy-12-[2'-(3"-sec-butenyloxy-4"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1,14-dihydroxy-12-[2'-(3",4"-dihydroxycyclohexyl)-1-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (150 mg in 3 ml 33% methylene chloride in cyclohexane), sec-butenyl trichloroacetimidate (62 μl neat) was added and the reagents allowed to mix for 5 minutes. Trifluoromethanesulfonic acid (2 μl neat) was added slowly via syringe and the mixture stirred at room temperature. After 15 minutes the reaction was quenched by the addition of saturated sodium bicarbonate and extracted with ethyl acetate (3×8 ml). The combined organics were washed with brine and dried over magnesium sulfate. Purification of the concentrate by preparative TLC on silica gel (ethyl acetate:hexane (1:1)+1% methanol) gave the title compounds (11 mg 4"-ether; 13 mg 3"-ether).

A. (4"-ether):
MASS: (FAB) 831 (M+Na)
Partial $^1$H NMR δ: 5.65 (m, 1H); 5.32 (brd J=3.0 Hz, 1H); 4.87m, 4.18M (brs, 1H); 4.58 (brd J=4.0 Hz, 1H); 4.41 (brd J=14 Hz, 1H).

B. (3"-ether):
MASS (FAB) 831 (M+Na)
Partial $^1$H NMR δ: 5.65 (m, 1H); 5.31 (brs, 1H); 4.82m, 4.22M (brs, 1H); 4.58 (brd J=4.0 Hz, 1H); 4.41 (brd J=14 Hz, 1H).

EXAMPLE 55

17-Ethyl-1-hydroxy-12-[2'-(4"-cinnamyloxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-12-[2'-(4"-hydroxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (100 mg in 3 ml 33% methylene chloride in cyclohexane), cinnamyl trichloroacetimidate (54 μl neat) was added and the reagents allowed to mix for 5 minutes. Trifluoromethanesulfonic acid (2 μl neat) was added slowly via syringe and the mixture stirred at room temperature. At 30 minutes the reaction was quenched by the addition of saturated sodium bicarbonate and extracted with ethyl acetate (3×8 ml). The combined organics were washed with brine and dried over magnesium sulfate. Purification of the concentrate by preparative TLC on silica gel (ethyl acetate:hexane (1:2)+1% methanol) gave the title compound (45 mg).

MASS: (FAB) 891 (M+Li)
Partial $^1$H NMR δ: 6.62 (d J=15 Hz, 1H); 6.31 (dt J=15, 6.0 Hz, 1H); 4.56 (brd J=4.0 Hz, 1H); 4.31 (d J=6.0 Hz, 2H).

EXAMPLE 56

17-Ethyl-1-hydroxy-12-[2'-(3"-methoxy-4"-phenylpropyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-12-[2'-(4'-cinnamyloxy-3"-methoxycyclohexyl)-1'-methyvinyl]-23,25-dimethoxy-13,19,21,27-tetramethyl-11,28-dioxa-4-azatricyclo[22.3.1.0$^{4,9}$]octacos-18-ene-2,3,10,16-tetraone (16 mg in 2 ml ethanol) was added 2 mg of 5% rhodium on carbon catalyst. The reaction flask was fitted with a hydrogen balloon, evacuated and recharged with hydrogen (3 times) and stirred at room temperature. After 30 minutes, the mixture was filtered over diatomacous earth, concentrated and purified by preparative TLC on silica gel (ethyl acetate:hexane (1:2)+1% methanol) to give the title compound (5.5 mg).

MASS: (FAB) 916 (M+Na)
Partial $^1$NMR δ: 4.58 (brd J=4.0 Hz, 1H); 4.42m, 4.32M (brs, 1H); 4.40 (brd J=14 Hz, 1H); 2.69 (t J=8.0 Hz, 2H).

EXAMPLE 57

17-Ethyl-1,14-dihydroxy-12-[2'-(4"-sec-phenethyloxy-3"-methoxycyclohexyl)-1'-methylvinyl]-23,25-dimethoxy-13,19,21,27-tetramethyl-11,28-dioxa-4-azatricyclo[22.3.1.9$^{4,9}$]octacos-18-ene-2,3,10,16-tetraone To a solution of 17-ethyl-1,14-dihydroxy-12-[2'-(4"-hydroxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (75 mg in 3 ml 33% methylene chloride in cyclohexane), sec-phenethyl trichloroacetimidate (38 μl neat) was added and the reagents allowed to mix for 5 minutes. Trifluoromethanesulfonic acid 3 μl neat) was added slowly via syringe and the mixture stirred at room temperature. After 30 minutes the reaction was quenched by the addition of saturated sodium bicarbonate and extracted with ethyl acetate (3×10 ml). The combined organics were washed with brine and dried over magnesium sulfate. Purification of the concentrate by flash chromatography on silica gel (ethyl acetate:hexane (1:2)+1% methanol) gave the title compound (13 mg).

MASS: (FAB) 918 (M+Na) 902 (M+Li)
Partial $^1$H NMR δ: 5.28 (m, 1H); 4.56 (m, 1H); 4.41 (brd J=14 Hz, 1H); 4.86m, 4.20M (brs, 1H).

EXAMPLE 58

17-Ethyl-1,14-dihydroxy-12-[2'-(4"-(2'''-methylcinnamyloxy)-3"-methoxyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1,14-dihydroxy-12-[2'-(4"-hydroxy-3"-methoxycyclohexy)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (50 mg in 1.5 ml 33% methylene chloride in cyclohexane), 2-methylcinnamyl trichloroacetimidate (28 μl neat) was added and the reagents allowed to mix for 5 minutes. Trifluoromethanesulfonic acid (3 μl neat) was added slowly via syringe and the mixture stirred at room temperature. After 20 minutes the reaction was quenched by the addition of saturated sodium bicarbonate and extracted with ethyl acetate (3×10 ml). The combined organics were washed with brine and dried over magnesium sulfate. Purification of the concentrate by flash chromatography on silica gel (ethyl acetate:-hexane (1:2)+1% methanol) gave the title compound (9 mg).

MASS: (FAB) 944 (M+Na)

Partial $^1$H NMR δ: 6.53 (brs, 1H); 5.32 (brd, J=3 Hz, 1H); 4.85m, 4.21M (brs, 1H); 4.59 (brd J=4 Hz, 1H); 4.41 (brd J=14 Hz, 1H); 4.16 (brs, 2H); 1.90 (brs, 3H).

EXAMPLE 59

17-Ethyl-1,14-dihydroxy-12-[2'-(4''-(-4'''-methyl-2''',4'''-hexadienyloxy)-3''-methoxycyclohexyl)-1'-methylvinyl]-23,25-dimethoxy-13,19,21,27-tetramethyl-11,28-dioxa-4-azatricycl[22.3.1.0$^{4,9}$]octacos-18-ene-2,3,10,16-tetraone To a solution of 17-ethyl-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (200 mg in 6 ml 33% methylene chloride in cyclohexane), 4-methyl-2,4-hexadienyl trichloroacetimidate (97 μl neat) was added and the reagents allowed to mix for 5 minutes. Trifluoromethanesulfonic acid (5 μl neat) was added slowly via syringe and the mixture stirred at room temperature. After 4 hours the reaction was quenched by the addition of saturated sodium bicarbonate and extracted with ethyl acetate (3×20 ml). The combined organics were washed with brine and dried over magnesium sulfate. Purification of the concentrate by flash chromatography on silica gel (ethyl acetate:-hexane (1:2)+1% methanol) gave the title compound (8 mg).

MASS: (FAB) 892 (M+Li)

Partial $^1$H NMR δ: 6.25 (d J=15 Hz, 1H); 5.64 (dt J=15,7 Hz, 1H); 5.31 (brd J=3 Hz, 1H); 4.83m, 4.21M (brs, 1H); 4.59 (brd J=4 Hz, 1H); 4.41 (brd J=14 Hz, 1H); 4.18 (brd J=7 Hz, 2H).

EXAMPLE 60

17-Ethyl-1,14-dihydroxy-12-[2'-(4''-(p-methoxy cinnamyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (200 mg in 6 ml 33% methylene chloride in cyclohexane), p-methoxycinnamyl trichloroacetimidate (117 μl neat) was added and the reagents allowed to mix for 5 minutes. Trifluoromethanesulfonic acid (3 μl neat) was added slowly via syringe and the mixture stirred at room temperature. After 20 minutes the reaction was quenched by the addition of saturated sodium bicarbonate and extracted with ethyl acetate (3×20 ml). The combined organics were washed with brine and dried over magnesium sulfate. Purification of the concentrate by flash chromatography on silica gel (ethyl acetate:-hexane (1:2)+1% methanol) gave the title compound (16 mg).

MASS: (FAB) 960 (M+Na) 944 (M+Li)

Partial $^1$H NMR δ: 7.29 (brd J=9 Hz, 2H); 6.85 (brd J=9 Hz, 2H); 5.32M, 5.19m (brd J=3 Hz, 1H); 4.84m, 4.21M (brs, 1H); 4.61 (brd J=5 Hz, 2H); 4.41 (brd J=14 Hz, 1H).

EXAMPLE 61

17-Ethyl-1,14-dihydroxy-12-[-2'-(4''-(3''',4'''-methylenedioxycinnamyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (200 mg in 6 ml 33% methylene chloride in cyclohexane), 3',4'-methylenedioxycinnamyl trichloroacetimidate (122 μl neat) was added and the reagents allowed to mix for 5 minutes. Trifluoromethanesulfonic acid (3 μl neat) was added slowly via syringe and the mixture stirred at room temperature. After 30 minutes the reaction was quenched by the addition of saturated sodium bicarbonate and extracted with ethyl acetate (3×20 ml). The combined organics were washed with brine and dried over magnesium sulfate. Purification of the concentrate by flash chromatography on silica gel (ethyl acetate:hexane (1:2)+1% methanol) gave the title compound (10 mg).

MASS: (FAB) 974 (M+Na)

Partial $^1$H NMR δ: 6.54 (d J=16 Hz, 1H); 6.14 (dt J=16,6 Hz, 1H); 5.95 (s, 2H) 5.33M, 5.19m (brd J=3 Hz, 1H); 4.59 (brd J=4 Hz, 1H); 4.41 (brd J=14 Hz, 1H); 4.27 (brd J=6 Hz, 2H).

EXAMPLE 62

17-Ethyl-1,14-dihydroxy-12-[2'-(4''-(4''',4'''-dimethyl-2'''-trans-pentenyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (200 mg in 6 ml 33% methylene chloride in cyclohexane), 4,4-dimethyl-2-trans-pentenyl trichloroacetimidate (98 μl neat) was added and the reagents allowed to mix for 5 minutes. Trifluoromethanesulfonic acid (10 μl neat) was added slowly via syringe and the mixture stirred at room temperature. After 1.5 hours the reaction was quenched by the addition of saturated sodium bicarbonate and extracted with ethyl acetate (3×20 ml). The combined organics were washed with brine and dried over magnesium sulfate. Purification of the concentrate by flash chromatography on silica gel (ethyl acetate:hexane (1:2)+1% methanol) gave the title compound (17 mg).

MASS: (FAB) 894 (M+Li)

Partial $^1$H NMR δ: 5.70 (d J=16 Hz, 1H); 5.48 (dt J=16,7 Hz, 1H); 5.31 (brd J=3 Hz, 1H); 4.84m, 4.21M) (brs, 1H); 4.59 (brd J=4 Hz, 1H); 4.41 (brd J=14 Hz, 1 H); 4.18 (brd J=7 Hz, 2H); 1.01 (s, 9H).

EXAMPLE 63

17-Ethyl-1,14-dihydroxy-12-[2'-(4''-(-3''''-cyclohexyl-2'''-trans-propenyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (200 mg in 6 ml 33% methylene chloride in cyclohexane), 3-cyclohexyl-2-trans-propenyl trichloroacetimidate (108 μl neat) was added and the reagents allowed to mix for 5 minutes. Trifluoromethanesulfonic acid (7 μl neat) was added slowly via syringe and the mixture stirred at room temperature. After 1 hour the reaction was quenched by the additio of saturated sodium bicarbonate and extracted with ethyl acetate (3×20 ml). The combined organics were washed with brine and dried over magnesium sulfate. Purification of the concentrate by flash chromatography on silica gel (ethyl acetate:hexane (1:2)+1% methanol) gave the title compound (20 mg).

MASS: (FAB) 936 (M+Na)

Partial $^1$H NMR δ: 5.32M, 5.19m (brd J=3 Hz, 1H); 4.84m, 4.21M (brs, 1H); 4.59 (brd J=4 Hz, 1H); 4.41 (brd J=14 Hz, 1H); 4.06 (brd J=5 Hz, 2H).

EXAMPLE 64

17-Ethyl-1,14-dihydroxy-12-[2'-(4''-p-fluorocinnamyloxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (200 mg in 6 ml 33% methylene chloride in cyclohexane), p-fluorocinnamyl trichloroacetimidate (112 μl neat) was added and the reagents allowed to mix for 5 minutes. Trifluoromethanesulfonic acid (7 μl neat) was added slowly via syringe and the mixture stirred at room temperature. After 20 minutes the reaction was quenched by the addition of saturated sodium bicarbonate and extracted with ethyl acetate (3×20 ml). The combined organics were washed with brine and dried over magnesium sulfate. Purification of the concentrate by flash chromatography on silica gel (ethyl acetate:hexane (1:2)+1% methanol) gave the title compound (33 mg).

MASS: (FAB) 932 (M+Li)

Partial $^1$H NMR δ: 7.37 (d J=6 Hz, 1H); 7.31 (d J=6 Hz, 1H); 7.01 (d J=9 Hz, 1H); 6.96 (d J=9 Hz, 1H); 6.57 (d J=16 Hz, 1H); 6.21 (dt J=16, 6 Hz, 1H); 5.32M, 5.19m (brd J=3 Hz, 1H); 4.83m, 4.21M (brs, 1H); 4.59 (brd J=4 Hz, 1H); 4.41 (brd J=14 Hz, 1H); 4.29 (d J=6 Hz, 2H).

EXAMPLE 65

17-Ethyl-1,14-dihydroxy-12-[2'-(4''-p-chlorocinnamyloxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (200 mg in 6 ml 33% methylene chloride in cyclohexane), p-chlorocinnamyl trichloroacetimidate (119 μl neat) was added and the reagents allowed to mix for 5 minutes. Trifluoromethanesulfonic acid (7 μl neat) was added slowly via syringe and the mixture stirred at room temperature. After 30 minutes the reaction was quenched by the addition of saturated sodium bicarbonate and extracted with ethyl acetate (3×20 ml). The combined organics were washed with brine and dried over magnesium sulfate. Purification of the concentrate by flash chromatography on silica gel (ethyl acetate:hexane (1:2)+1% methanol) gave the title compound (34 mg).

MASS: (FAB) 948 (M+Li)

Partial $^1$H NMR δ: 6.58 (d J=16 Hz, 1H); 6.27 (dt J=16, 6 Hz, 1H); 5.32M, 5.19m (brd J=3 Hz, 1H); 4.84m, 4.21M (brs, 1H); 4.59 (brd J=4 Hz, 1H); 4.41 (brd J=14 Hz, 1H); 4.30 (d J=6 Hz, 1H).

EXAMPLE 66

17-Ethyl-1,14-dihydroxy-12-[2'-(4''-p-bromocinnamyloxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (200 mg in 6 ml 33% methylene chloride in cyclohexane), p-bromocinnamyl trichloroacetimidate (135 μl neat) was added and the reagents allowed to mix for 5 minutes. Trifluoromethanesulfonic acid (7 μl neat) was added slowly via syringe and the mixture stirred at room temperature. After 1 hour the reaction was quenched by the addition of saturated sodium bicarbonate and extracted with ethyl acetate (3×20 ml). The combined organics were washed with brine and dried over magnesium sulfate. Purification of the concentrate by flash chromatography on silica gel (ethyl acetate:hexane (1:2)+1% methanol) gave the title compound (19 mg).

MASS: (FAB) 984, 986 (M+)

Partial $^1$H NMR δ: 7.42 (d J=9 Hz, 2H); 7.20 (d J=9 Hz, 2H); 6.56 (d J=16 Hz, 1H); 6.29 (dt J=16, 6 Hz, 1H); 5.31M, 5.19m (brd J=3 Hz, 1H); 4.85m, 4.21M (brs, 1H); 4.59 (brd J=4 Hz, 1H); 4.41 (brd J=14 Hz, 1H); 4.28 (d J=6 Hz, 2H).

EXAMPLE 67

17-Ethyl-1,14-dihydroxy-12-[2'-(3''-methoxy-4''-p-fluorophenpropyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1,14-dihydroxy-12-[2'-(4''-p-fluorocinnamyloxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (22 mg in 2 ml ethanol) was added 6 mg of 5% rhodium on carbon catalyst. The reaction flask was fitted with a hydrogen balloon, evacuated and recharged with hydrogen (3 times) and stirred at room temperature. After 45 minutes, the mixture was filtered over Celite, concentrated and purified by preparative TLC on silica gel (ethyl acetate:hexane (1:2)+1% methanol) to give the title compound (7.5 mg).

MASS: (FAB) 934 (M+Li)

Partial $^1$H NMR δ: 7.16 (d J=6 Hz, 1H); 7.12 (d J=6 Hz, 1H); 6.97 (d J=9 Hz, 1H); 6.92 (d J=9 Hz, 1H); 5.32M, 5.19m (brd J=3 Hz, 1H); 4.85m, 4.21M (brs, 1H); 4.59 (brd J=4 Hz, 1H); 4.41 (brd J=14 Hz, 1H); 2.67 (t J=8 Hz, 2H).

EXAMPLE 68

17-Ethyl-1-hydroxy-12-[2'-(3'',4''-diallyloxy-cyclohexyl)-1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone To a solution of 17-ethyl-1-hydroxy-12-[2'-(3'',4''-diallyloxy-cyclohexyl)-1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone (20 mg in 0.75 ml 33% methylene chloride in cyclohexane), allyl trichloroacetimidate (16 μL neat) was added and the reagents allowed to mix for 5 minutes. Trifluoromethanesulfonic acid (2.0 μL neat) was added slowly via syringe and the mixture stirred at room temperature. After 5 hours the reaction was quenched by the addition of saturated sodium bicarbonate and extracted with ethyl acetate (3×5 ml). The combined organics were washed with brine and dried over magnesium sulfate. Purification of the concentrate by flash chromatography on silica gel (ethyl acetate:hexane (1:3)+1% methanol) gave the title compound (6.8 mg). ($^1$H NMR was consistent with the desired structure).

EXAMPLE 69

17-Ethyl-1-hydroxy-12-[2'-(3'',4''-dipropyloxycyclohexyl)-1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone To a solution of 17-ethyl-1-hydroxy-12-[2'-(3'',4''-dipropyloxycyclohexyl)-1'-methylvinyl]-23,25-dimethoxy-13,19,21,27-tetramethyl-11,28-dioxa-4-azatricyclo[22.3.1.04,9]-octacos-18-ene-2,3,10,16-tetraone (6.8 mg in 600 μl ethyl acetate) was added 4 mg of 5% rhodium on carbon catalyst. The reaction flask was fitted with a hydrogen balloon, evacuated and recharged with hydrogen (3 times) and stirred at room temperature. After 25 minutes, the mixture was filtered over Celite, concentrated and purified by flash chromatography on silica gel (ethyl acetate:hexane (1:3)+1% methanol) to give the title compound (4.5 mg).

MASS: (FAB) 852 (M+Li)

Partial $^1$H NMR δ: 4.59 (brm, 1H); 4.42m, 4.33M (brs, 1H); 4.41 (brd, J=14 Hz, 1H); 3.54 (m, 4H).

EXAMPLE 70

17-Ethyl-1,14-dihydroxy-12-[2'-(4''-(2'''-benzylamino)ethoxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Step A: 17-Ethyl-1-hydroxy-14-(tert-butyldimethylsiloxy)-12-[2'-(4''-(tert-butyldimethylsiloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (2.35 g) in dry methylene chloride (20 ml) was added an excess of 2,6-lutidine (1.04 ml) and the mixture was stirred at room temperature. After 10 minutes, tert-butyldimethylsilyl trifluoromethanesulfonate (1.50 ml) was added via syringe. After 1 hour the reaction mixture was diluted with ethyl acetate, extracted from saturated sodium bicarbonate, washed with brine and the organic phase dried over magnesium sulfate. Removal of the solvent in vacuo and flash chromatography on silica gel (ethyl acetate: hexane (1:3)+1% methanol) gave the title compound (2.91 g). ($^1$H NMR was consistent with the desired structure).

Step B: 17-Ethyl-1-hydroxy-14-(tert-butyldimethylsiloxy)-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-14-(tert-butyldimethylsiloxy)-12-[2'-(4''-(tert-butyldimethylsiloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (2.91 g) in acetonitrile (15 ml) was added a solution of 2% hydrogen fluoride in aqueous acetonitrile (2 ml), and the mixture stirred at room temperature. After 4 hours, the solution was diluted with ethyl acetate, extracted with saturated sodium bicarbonate solution and the organic phase dried over magnesium sulfate. Purification of the concentrate by flash chromatography on silica gel (ethyl acetate:hexane (1:1)+1% methanol) gave the title compound (1.51 g). ($^1$H NMR was consistent with the desired structure).

Step C: 17-Ethyl-1-hydroxy-14-(tert-butyldimethylsiloxy)-12-[2'-(4''-allyloxy-3''-methoxycyclohexyl-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To solution of 17-ethyl-1-hydroxy-14-(tert-butyldimethylsiloxy)-12-[2'-(4''-hydroxy-3''-methoxycyclohexyl)-1''-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (820 mg in 9 ml 33% methylene chloride in cyclohexane) allyl trichloroacetimidate (366 μl neat) was added and the reagents allowed to mix for 5 minutes. Trifluoromethanesulfonic acid (16 μl neat) was added slowly via syringe and the mixture stirred at room temperature. After 17 hours the reaction was quenched by the addition of saturated sodium bicarbonate and extracted with ethyl acetate (3×15 ml). The combined organics were washed with brine and dried over magnesium sulfate. Purification of the concentrate by flash chromatography on silica gel (ether:hexane (2:3)) gave the title compound (800 mg). ($^1$H NMR was consistent with the desired structure).

Step D: 17-Ethyl-1-hydroxy-14-(tert-butyldimethylsiloxy)-12-[2'-(4"-(2''',3'''-dihydroxypropyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl--1-hydroxy-14-(tert-butyldimethylsiloxy)-12-[2'-(4"-allyloxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (344 mg in 3 ml dry diethyl ether) was added 150 μl pyridine followed by 1.6 ml of a 0.25M osmium tetraoxide solution in THF and the mixture stirred at room temperature. After 15 minutes, 10 ml of a 20% sodium bisulfite solution were added and the mixture diluted with 20 ml ethyl acetate. The layers were separated and the organic portion re-extracted with 20% sodium bisulfate (3×20 ml) then washed with a saturated brine solution and dried over sodium sulfate. The concentrate was purified by flash chromatography on silica gel (ethyl acetate:hexane (1:1)+1% methanol, then methylene chloride:hexane:methanol (10:2:1)) to give the title compound (300 mg) ($^1$H NMR was consistent with the desired structure).

Step E: 17-Ethyl-1-hydroxy-14-(tert-butyldimethylsiloxy)-12-[2'-(4"-ethanaloxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-14-(tert-butyldimethylsiloxy)-12-[2'-(4"-(2''',3'''-dihydroxypyroploxy)-3"-methoxycyclohexyl)-1'-methylvinyl]-23,25-dimethoxy-13,19,21,27-tetramethyl-11,28-dioxa-4-aza-tricyclo[22.3.1.0$^{4,9}$]octacos-18-ene-2,3,10,16-tetraone (284 mg in 6 ml of in 20% aqueous tetrahydrofuran) was added sodium metaperiodate (72.3 mg) and the mixture stirred vigorously for 2 hours. At this time an additional 50 mg of sodium metaperiodate were added. After 1.5 hours the mixture was diluted with ethyl acetate and extracted from half-saturated sodium bicarbonate. The organic portion was dried over magnesium sulfate and purified by flash chromatography on silica gel (ethyl acetate:hexane (1:1)+1% methanol) to give the title compound (151 mg).($^1$H NMR was consistent with the desired structure).

Step F: 17-Ethyl-1-hydroxy-14-(tert-butyldimethylsilioxy)-12-[2'-(4"-(2'''-benzylamino)-ethoxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1--hydroxy-14-(tert-butyldimethylsiloxy)-12-[2'-(4"-ethanaloxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (9.5 mg in 0.25 ml dry terahydrofuran) was added benzylamine (2.5 μl) and the mixture stirred for 10 minutes at room temperature. This was cooled to −78° C. and acetic acid (10 μl) was added followed by potassium triphenylborohydride (25 μl of a 0.5M solution in THF). After 45 minutes, the reaction was quenched by the addition of saturated ammonium chloride and warmed to room temperature. The mixture was extracted with ethyl acetate (3×5 ml) and dried over magnesium sulfate. The concentrate was purified by flash chromatography on silica gel (ethyl acetate:hexane (1:2)+1% methanol, then 2% ammonium hydroxide, 5% methanol in methylene chloride) to give the title compound (3.5 mg).

MASS (FAB) 1039 (M+). ($^1$H NMR was consistent with the desired structure).

Step G: 17-Ethyl-1,14-dihydroxy-12-[2'-(4"-(2'''-benzyl-amino)-ethoxy-3"-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone To a solution of 17-ethyl-1-hydroxy-14-(tert-butyldimethylsiloxy)-12-[2'-(4"-(2'''-benzylamino)ethoxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (3.5 mg) in acetonitrile (100 μl) was added a solution of 2% HF in aqueous acetonitrile (100 μl), and the mixture stirred at room temperature. After 2 hours, the solution was diluted with ethyl acetate, extracted with saturated sodium bicarbonate solution and the organic phase dried over magnesium sulfate. Purification of the concentrate by flash chromatography on silica gel (ethyl acetate:hexane (1:1)+1% methanol, then 2% ammonium hydroxide, 5% methanol in methylene chloride) gave the title compound (2 mg).

MASS (FAB) 925 (M+).

Partial $^1$H NMR δ: 7.32 (m, 5H); 5.32M, 5.17m (brd J=3 Hz, 1H); 4.84m, 4.21M (brs, 1H); 4.59 (brd, J=4 Hz, 1H); 4.41 (brd J=14 Hz, 1H); 3.84 (brs, 2H).

EXAMPLE 71

17-Ethyl-1-hydroxy-12-[2'-(4"-(2'''-benzylamino)ethoxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Step A: 17-Ethyl-1-hydroxy-12-[2'-(4"-allyloxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-12-[2'-(4"-hydroxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (400 mg in 6 ml 33% methylene chloride in cyclohexane), allyl trichloroacetimidate (209 μl neat) was added and the reagents allowed to mix for 5 minutes. Trifluoromethanesulfonic acid (9 μl neat) was added slowly via syringe and the mixture stirred at room temperature. After 6 hours the reaction was quenched by the addition of saturated sodium bicarbonate and extracted with ethyl acetate (3×10 ml). The combined organics were washed with brine and dried over magnesium sulfate. Purification of the concentrate by flash chromatography on silica gel (ethyl acetate:hexane (1:3)+1% methanol) gave the title compound (320 mg). ($^1$H NMR was consistent with the desired structure).

Step B: 17-Ethyl-1-hydroxy-12-[2'-(4"-(2''',3'''-dihydroxypropyloxy)-3"-methoxycyclohexyl)-1'-methyl-vinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-12-[2'-(4''-allyloxy-3''-methoxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetrone (310 mg in 3.5 ml dry ether) was added 350 μl pyridine followed by 1.5 ml of a 0.25M osmium tetraoxide solution in THF and the mixture stirred at room temperature. After 15 minutes, 10 ml of a 20% sodium bisulfite solution were added and the mixture diluted with 20 ml ethyl acetate. The layers were separated and the organic portion re-extracted with 20% sodium bisulfite (3×20 ml) then washed with a saturated brine solution and dried over sodium sulfate. The concentrate was purified by flash chromatography on silica gel (ethyl acetate:hexane (1:1)+1% methanol, then methylene chloride:hexane:methanol (10:2:1)) to give the title compound (232 mg). ($^1$H NMR was consistent with the desired structure).

Step C: 17-Ethyl-1-hydroxy-12-[2'-(4''-ethanaloxy-3''-methoxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone To a solution of 17-ethyl-1-hydroxy-12-[2'-(4''-(2''',3'''-dihydroxypropyloxy)-3''-methoxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone (232 mg in 25% aqueous tetrahydrofuran) was added sodium metaperiodate (70.2 mg) and the mixture stirred vigorously. After 4 hours the mixture was diluted with ethyl acetate and extracted from half-saturated sodium bicarbonate. The organic portion was dried over magnesium sulfate and purified by flash chromatography on silica gel (ethyl actate:hexane (1:1)+1% methanol) to give the title compound (112 mg). ($^1$H NMR was consistent with the desired structure).

Step D: 17-Ethyl-1-hydroxy-12-[2'-(4''-(2'''-benzylamino)-ethoxy-3''-methoxycyclohexyl)-1'-methylvinyl]-23,25-dimethoxy-13,19,21,27-tetramethyl-11,28-dioxa-4-azatricyclo-[22.3.1.0^{4,9}]octacos-18-ene-2,3,10,16-tetraone To a solution of 17-ethyl-1-hydroxy-12-[2'-(4'-ethanaloxy-3''-methoxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone (4 mg in 0.30 ml dry terahydrofuran) was added benzylamine (2.0 μl) and the mixture stirred for 10 minutes at room temperature. This was cooled to −78° C. and acetic acid (7 μl) was added followed by potassium triphenylborohydride (16 μl of a 0.5M solution in THF). After 35 minutes, the reaction was quenched by the addition of saturated amonium chloride and warmed to room temperature. The mixture was extracted with ethyl acetate (3×5 ml) and dried over magnesium sulfate. The concentrate was purified by flash chromatography on silica gel (ethyl acetate:hexane (1:2)+1% methanol, then 2% ammonium hydroxide, 5% methanol in methylene chloride) to give the title compound (2.1 mg).

Partial $^1$H NMR δ: 7.32 (m, 5H); 4.56 (brd, J=4 Hz, 1H); 4.41 (brd J=14 Hz, 1H); 3.82 (brs, 2H).

EXAMPLE 72

17-Ethyl-1,14-dihydroxy-12-[2'-(4''-(2'''-benzyloxyethoxy)-3''-methoxycyclohexyl)-1'-methylvinyl]-23,35-dimethoxy-13,19,21,27-tetramethyl-11,28-dioxa-4-azatricyclo[22.3.1.0^{4,9}]octacos-18-ene-2,3,10,16-tetraone Step A: 17-Ethyl-1-hydroxy-14-(-tert-butyldimethylsiloxy)-12-[2'-(4''-(2-hydroxyethoxy)-3''-methoxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone To a solution of 17-ethyl-1-hydroxy-14-(tetra-butyldimethylsiloxy)-12-[2'-(4''-ethanaloxy- 3''-methoxycyclohexyl)-1'-methylvinyl]-23,25-dimethoxy-13,19,21,27-tetramethyl-11,28-dioxa-4-azatricyclo-[22.3.1.0^{4,9}]octacos-18-ene-2,3,10,16-tetraone (126 mg in 1.3 ml dry terahydrofuran) at −78° C. was added potassium triphenylborohydride (320 μl of a 0.5M solution in THF). After 45 minutes, the reaction was quenched by the addition of saturated ammonium chloride and warmed to room temperature. The mixture was extracted with ethyl acetate (3×15 ml) and dried over magnesium sulfate. The concentrate was purified by flash chromatography on silica gel (ethyl acetate:hexane (2:1+1% methanol) to give the title compound (80.2 mg). ($^1$H NMR was consistent with the desired structure).

Step B: 17-Ethyl-1-hydroxy-14-(tetra-butyldimethylsiloxy)-12-[2'-(4''-(2-benzyloxyethoxy)-3''-methoxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone To a solution of 17-ethyl-1-hydroxy-14-(-tert-butyldimethylsiloxy)-12-[2'-(4''-(2-hydroxyethoxy)-3''-methoxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone (41.7 mg in 0.6 ml 33% methylene chloride in cyclohexane), benzyl trichloroacetimidate (15.8 μl neat) was added and the reagents allowed to mix for 5 minutes. Trifluoromethanesulfonic acid (2 μl neat) was added slowly via syringe and the mixture stirred at room temperature. After 7 hours the reaction was quenched by the addition of saturated sodium bicarbonate and extracted with ethyl acetate (3×5 ml). The combined organics were washed with brine and dried over magnesium sulfate. Purification of the concentrate by flash chromatography on silica gel (ethyl acetate:hexane (1:3)+1% methanol) gave the title compound (24 mg). ($^1$H NMR was consistent with the desired structure).

Step C: 17-Ethyl-1,14-dihydroxy-12-[2'-(4''-(2'''--benzyl-oxyethoxy-3'-methoxycyclohexyl)-1'-methylvinyl]-23,25-dimethoxy-13,19,21,27-tetra-methyl-11,28-dioxa-4-azatricyclo[22.3.1.0^{4,9}]octacos-18-ene-2,3,10,16-tetraone To a solution of 17-ethyl-1-hydroxy-14-(tert-butyldimethylsiloxy)-12-[2'-(4''-(2'''-benzyloxyethoxy)-3''-methoxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone (10 mg) in acetonitrile (500 μl) was added a solution of 2% HF in aqueous acetonitrile (200 μl), and the mixture stirred at room temperature. After 2.5 hours, the solution was diluted with ethyl acetate, extracted with saturated sodium bicarbonate solution and the organic phase dried over magnesium sulfate. Purification of the concentrate by flash chromatography on silica gel (ethyl acetate:hexane (1:2)+1% methanol) gave the title compound (4 mg).

MASS (FAB) 932 (M+Li).

Partial $^1$H NMR δ: 7.33 (m, 5H); 5.32M, 5.19m (brd J=3 Hz, 1H); 4.85m, 4.21M (brs, 1H); 4.58 (s, 2H); 4.41 (brd J=14 Hz, 1H).

EXAMPLE 73

17-Ethyl-1,14-dihydroxy-12-[2'-(4"-benzyloxymethoxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1,14-dihydroxy-12-[2'-(4"-hydroxy-3'-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (150 mg in 2 ml methylene chloride) was added diisopropylethylamine (99.4 μl) followed by benzyl chloromethyl ether (34.2 μl neat) and the mixture stirred at room temperature. After 24 hours, the reaction was quenched by the addition of saturated sodium bicarbonate and extracted with ethyl acetate (3×20 ml). The combined organics were washed with brine and dried over magnesium sulfate. Purification of the concentrate by flash chromatography on silica gel (ethyl acetate:hexane (1:2)+1% methanol) gave the title compound (92 mg).

MASS: (FAB) 918 (M+Li).

Partial $^1$H NMR δ: 7.33 (m, 5H); 5.32M, 5.19m (brd J=3 Hz, 1H); 4.87 (s, 2H); 4.63 (s, 2H); 4.59 (brd J=4 Hz, 1H); 4.41 (brd J=14 Hz, 1H).

EXAMPLE 74

17-Ethyl-1,14-dihydroxy-12-[2'-(4"-(napth-2-yloxy)-3"-allyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1,14-dihydroxy-12-[2'-(4"-(napth-2-yloxy)-3"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone in 33% methylene chloride/cyclohexane is added 1.5 equivalents of allyl trichloroacetimidate, and the reagents are allowed to mix for 5 minutes. A catalytic amount of trifluoromethanesulfonic acid is then added slowly via syringe and the mixture is stirred at room temperature. After 3 hours the reaction is quenched by the addition of saturated sodium bicarbonate and extracted with ethyl acetate. The combined organics are washed with brine and dried over magnesium sulfate. Purification of the concentrate by flash chromatography on silica gel gives the title compound.

EXAMPLE 75

17-Ethyl-1,14-dihydroxy-12-[2'-(4"-(4'''-t-butyldimethylsiloxycinnamyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1,14-dihydroxy-12-[2'-(4"-hydroxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3-10,16-tetraone (700 mg in 12 ml methylene chloride)4-t-butyldimethylsiloxycinnamyl trichloroacetimidate (550 μl neat) was added and the reagents allowed to mix for 5 minutes. Camphorsulfonic acid (35 mg) was added and the mixture stirred at room temperature. After 5 hours the reaction was quenched by the addition of saturated sodium bicarbonate and extracted with ethyl acetate (3×15 ml). The combined organics were washed with brine and dried over magnesium sulfate. Purification of the concentrate by flash chromatography on silica gel (ethyl acetate:hexane (1:2)+1% methanol) gave the title compound (190 mg).

$^1$H NMR spectrum was consistent with the desired structure.

EXAMPLE 76

17-Ethyl-1,14-dihydroxy-12-[2'-(4"-(4'''-hydroxycinnamyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1,14-dihydroxy-12-[2'-(4"-(4'''-t-butyldimethylsiloxycinnamyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (190 mg in 2 ml tetrahydrofuran contained in a polypropylene vial) was added 500 μof a solution of hydrogen fluoride-pyridine complex (40% in (2:1) tetrahydrofuran:pyridine) and the mixture stirred at room temperature. After 2 hours, the reaction was quenched by the careful addition of saturated sodium bicarbonate and extracted with ethyl acetate. The combined organics were dried over magnesium sulfate, concentrated in vacuo and purified by flash chromatography on silica gel (ethyl acetate:hexane (2:1) to give the title compound (50 mg).

MS(FAB) 930 (M+Li).

$^1$H NMR spectrum was consistent with the desired structure.

EXAMPLE 77

17-Ethyl-1,14,dihydroxy-12-[-2'-(4"-(2'''-phenyl-2'''-oxo-ethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Step A: 17-Ethyl-1-hydroxy-14-(tert-butyldimethylsiloxy)-12-[2'-4"-(2'''-phenyl-2'''-hydroxyethyloxy)-3"-methoxycyclohexyl)-1'methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-14-(tert-butyldimethylsiloxy)-12-[2'-(4"-ethanaloxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (41 mg in 0.5 ml methylene chloride) at −78° C. was added phenylmagnesium bromide (15 μL of a 3M solution in diethyl ether) and the mixture stirred a low temperature. After 30 minutes the reaction was quenched by addition of saturated ammonium chloride and extracted with ethyl acetate. The organics were dried by passage through a magnesium sulfate plug and the concetrate purified by flash chromatography on silica gel (ethyl acetate:hexane (1:2)+1% methanol then (1:1+1% methanol) to give title compound (13 mg).

($^1$H NMR consistent with the desired structure)

Step B: 17-Ethyl-1-hydroxy-14-(tert-butyldimethyl siloxy)-12-[2'-(4"-(2"'-phenyl-2"'-oxoethyloxy)-3''' -methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone To solution of 17 ethyl-1-hydroxy-14-(tert-butyldimethylsiloxy)-12-[2'-(4"-(2'41 -phenyl-2"'hydroxyethyloxy)-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone (13 mg in 0.3 mL methylene chloride) was added powdered 4 Å molecular sieves (10 mg), 4-methylmorpholine N-oxide (6.0 mg), tetrapropylammonium perruthenate (1.0 mg) and the reaction stirred at room temperature. After 30 minutes the mixture was filtered through a small diatomaceous earth/silica gel plug and the filtrate concentrated in vacuo. Purification by flash chromatography on silica gel (ethyl acetate:hexane (1:2)+1% methanol) gave the title compound (10 mg).

(¹H NMR consistant with the desired structure)

Step C: 17-Ethyl-1,14-dihydroxy-12-[-2'-(4"-(2"'-phenyl-2"'-oxo-ethyloxy)-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone To a solution of 17-ethyl-1-hydroxy-14-(tert-butyldimethylsiloxy)-12-[2'-(2"'-phenyl-2"'-oxo-ethyloxy)-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone (10 mg in 0.4 mL tetrahydrofuran contained in a polypropylene vial) was added 20 μL of a solution of hydrogen fluoride-pyridine complex (40% in (2:1) tetrahydrofuran:pyridine) and the mixture stirred at room temperature. After 96 hours, the readtion was quenched by the careful addition of saturated sodium bicarbonate and extracted with ethyl acetate. The combined organics were dried by passage through a magnesium sulfate plug, concentrated in vacuo and purified by flash chromatography (ethyl acetate:hexane (1:1)+1% methanol) to give the title compound (5.2 mg).

MASS: (FAB) 917 (M+Li)

partial ¹H NMR δ: 7.92 (d J=7 Hz, 2H); 7.47 (m, 3H); 5.31 M, 5.17 m (brd J=3 Hz, 1H); 4.81 m, 4.20 M (brs, 1H); 4.41 (brd J=14 Hz, 1H); 3.06 (d J=4 Hz, 1H).

EXAMPLE 77B

17-Ethyl-1,14-dihydroxy-12-[2'-(4'-'-(2"'-phenyl-2"'-oxo-ethyloxy)-3"-methoxycyclohexyl)-1'-methylvinyl]-23,25-dimethoxy-13,19-21,27-tetramethyl-11,28-dioxa-4-azatricyclo[22.3.1.0⁴,⁹]octacos-18-ene-2,3,10,16-tetraone Step A: 17-Ethyl-1-hydroxy-14-(tert-butyldimethylsiloxy)-12-[2'-(4"-(2"'-phenyl-2"'-oxoethyloxy)-3' '-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone To a solution of 17-ethyl-1-1-hydroxy-14-(tert-butyldimethylsiloxy)-12-[2'-(4"-hydroxy-3"-methoxycyclohexyl)-1'-methylvinyl]-23,25-dimethoxy-13,19,21,27-tetramethyl-11,28-dioxa-4-azatricyclo[22.3.1.0.⁴,⁹]octacos-18-ene-2,3,10,16-tetraone (400 mg in 3.0 mL N,N-dimethylformamide) was added 2-bromacetophenone (263 mg) followed by potassium fluoride (25.6 mg) and the mixture heated to 70° C. After 48 hours, the mixture was cooled to room temperature, filtered over diatomaceous earth, diluted with ethyl acetate and washed with saturated sodium bicarbonate, water, and brine. The combined organics were dried over magnesium sulfate and concentrated in vacuo. Purification by flash chromatography on silica gel (ethyl acetate:hexane (1:2)+1% methanol) gave the desired product (145 mg).

(¹H NMR consistent with the desired structure)

Step B: 17-Ethyl-1,14-dihydroxy-12--[2'-(4"-(2"'-phenyl-2"'-oxo-ethyloxy)-3"-methoxycyclohexyl)-1'-methylvinyl]-23,25-dimethoxy-13,19,21,27-tetramethyl-11,28dioxa-4-azatricyclo[22.3.1.0⁴,⁹]octacos-18-ene-2,3,10,16-tetraone Conducted essentially as described in Example 77 Step C to give the desired product (86 mg).

(¹H NMR consistent with the desired structure).

EXAMPLE 78

17-Ethyl-1,14-dihydroxy-12-[2'-(4"-2"'-(3""-methoxyphenyl)-2"'-oxo-ethyloxy)-3"-methoxycyclohexyl)-1'-methylvinyl]-23,25-dimethoxy-13,19,21,27-tetramethyl-11,28-dioxa-4-azatricyclo[22.3.1.04,9]octacos-18-ene-2,3,10,16-tetraone The title compound was prepared employing the procedure essentially as described in Example 77, Steps A–C using 3-methoxyphenylmagnesium bromide as the nucleophile in Step A.

MASS: (FAB) 940 (M+)

partial ¹H NMR δ: 7.46 (m, 2H); 7.33 (t J=8 Hz, 1H); 7.09 (dd J=8,2 Hz, 1H); 5.31M, 5.17 m (brd J=3 Hz, 1H); 4.81m, 4.20M (brs, 1H); 4.41 (brd J=14 Hz, 1H); 3.84 (s, 3H); 3.07 (d J=Hz, 1H).

EXAMPLE 79

17-Ethyl-1,14-dihydroxy-12-[2'-(4"'-(2"'-(3""-methoxyphenyl)-2"'-hydroxyethyloxy)-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone To a solution of 17-ethyl-1-hydroxy-14-(tert -butyldimethylsiloxy)-12-[2'-(4"-(2"'-(3""--methoxyphenyl)-2"'-hydroxyethyloxy-)3"-methoxycyclohexyl)-1'-methylvinyl]-23,25-dimethoxy-13,19,21,27-tetramethyl-11,28-dioxa-4-azatricyclo[22.3.1.0⁴,⁹]octacos-1-8-ene-2,3,10,16-tetrone (29 mg in 0.6 mL tetrahydrofuran contained in a polypropylene vial) was added 80 μL of a solution of hydrogen fluoride-pyridine complex (40% in (2:1) tetrahydrofuran:pyridine) and the mixture stirred at room temperature. After 48 hours, the reaction was quenched by the careful addition of saturated sodium bicarbonate and extracted with ethyl acetate. The combined organics were dried by passage through a magnesium sulfate plug, concentrated in vacuo and purified by flash chromatography (ethyl acetate:hexane (1:1)+1% methanol) to give the title compound (9.5 mg).

MASS (FAB) 942 (M+)

partial ¹H NMR δ: 7.23 (m, 1H); 6.94 (s, 1H); 6.91 (d J=8 Hz, 1H); 6.79 (d J=8 Hz, 1H); 5.31M, 5.17m (brd J=3 Hz, 1H); 4.41 (brd J=14 Hz, 1H); 3.78 (s, 3H); 3.07 (d J=4 Hz, 1H).

EXAMPLE 80

17-Ethyl-1,14-dihydroxy-12-[2'-(4''-(2'''-methoxyphenyl)-2'''-oxo-ethyloxy)-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone The title compound was prepared employing the procedure essentially as described in Example 77, steps A–C using 4-methoxyphenylmagnesium bromide as the nucelophile in Step A.

MASS (FAB) 940 (M+)

partial ¹H NMR δ: 7.92 (d J=9 Hz,2H); 6.91 (d J=9 Hz, 2H); 1H); 5.31M, 5.17m (brd J=3 Hz, 1H); 4,81m, 4.20M (brs, 1H); 4.41 (brd J=14 Hz, 1H); 3.84 (s, 3H); 3.07 (d J=4 Hz, 1H).

EXAMPLE 81

17-Ethyl-1,14-dihydroxy-12-[2'-(4''-(m-fluor cinnamyloxy)-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone Prepared essentially as described in Example 44 using m-fluorocinnamyl trichoroacetimidate as the electrophile.

MASS (FAB) 948 (M+Na)

partial ¹H NMR δ: 7.30–6.85 (m, 4H); 6.59 (d J=17 Hz, 1H); 6.30 (dt J=17, 6 Hz, 1H); 5.30 M, 5.17 m (brd J=3 Hz, 1H); 4.41 (d J=14 Hz, 1H); 4.31 (d J=5 Hz, 2H).

EXAMPLE 82

17-Ethyl-1,14-dihydroxy-12-[2'-(4''-(3''',5'''-difluorocinnamyloxy)-3''-methoxycyclohexyl)-1'-methylvinyl]-23,25-dimethoxy-13,19,21,27-tetramethyl-11,28-dioxa-4-azatricyclo[22.3.0⁴,⁹]octacos-18-ene-2,3,10,16-tetraone Prepared essentially as described in Example 44 using 3,5-difluorocinnamyl trichloroacetimidate as the electrophile.

MASS (FAB) 950 (M+Li)

partial ¹H NMR δ: 6.92–6.56 (m, 3H); 6.55 (d J=16 Hz, 1H); 6.31 (dt J=16, 6 Hz, 1H); 5.30 M, 5.17 m (brd J=3 Hz, 1H); 4.41 (d J=14 Hz, 1H); 4.31 (d J=5 Hz, 2H).

EXAMPLE 83

17-Ethyl-1,14-dihydroxy-12-[2'-(4''-(m-nitro cinnamyloxy)-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone Step A: 17-Ethyl-1-hydroxy-1-4-(tert-butyldimethylsiloxy)-12-[2'-(4''-(m-nitrocinnamyloxy)-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone Prepared essentially as described in Example 70 (Step C) using m-nitrocinnamyl trichloroacetimidate as the electrophile.

¹H NMR consistent with the desired structure.

Step B: 17-Ethyl-1,14-dihydroxy-12-[2'-(4''-(m-nitr ocinnamyloxy)-3''-methxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone To a solution of 17-ethyl-1-hyxdroxy-14-(tert-butyl dimethylsiloxy)-12-[2'-(4''-(m-nitrocinnamyloxy)-2'''-hydroxyethyloxy)-3''-methoxycyclohexyl)1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone (124 mg in 1.5 mL tetrahydrofuran contained in a polypropylene vial) was added 600 μL of a solution of hydrogen fuoride-pyridine complex (40% in (2:1) tetrahydrofuran:pyridine) and the mixture stirred at room temperature. After 30 hours, the reaction was quenched by the careful addition of saturated sodium bicarbonate and extracted with ethyl acetate. The combined organics were dried by passage through a magnesium sulfate plug, concentrated in vacuo and purified by flash chromatography on silica gel (ethyl acetate:hexane (1:1)+1% methanol) to give the title compound (43 mg).

MASS (FAB) 959 (M+Li)

partial ¹H NMR δ: 8.22 (s, 1H); 8.06 (brd J=8 Hz, 1H); 7.66 (brd J=8 Hz, 1H); 7.46 (t J=8 Hz, 1H); 6.69 (d J=16 Hz, 1H); 6.44 (dt J=16, 6 Hz, 1H); 5.30 M, 5.17 m (brd J=3 Hz, 1H); 4.41 (d J=14 Hz, 1H).

EXAMPLE 84

17-Ethyl-1,14-dihydroxy-12-[2'-(4''-(3'''-phenyl-2-propynyloxy)-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone Prepared essentially as described in Example 83 using 3-phenylpropynyl trichloroacetimidate as the electrophile.

MASS (FAB) 912 (M+Li)

partial ¹H NMR δ: 7.54–7.28 (m, 5H); 5.30 M, 5.17 m (brd J=3 Hz, 1H); 4.41 (d J=14 Hz, 1H).

EXAMPLE 85

17-Ethyl-1,14-dihydroxy-12-[2'-(4''-(2'''-phenyl-2'''-propenyloxy)-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone Prepared essentially as described in Example 83 using 2-phenyl-2-propenyl trichloroacetimidate as the electrophile.

MASS (FAB) 915 (M+Li)

partial ¹H NMR δ: 7.47 (d J=8 Hz, 2H); 7.26 (m, 3H); 5.49 (s, 1H); 5.37 (s, 1H); 5.30 M, 5.17 m (brd J=3 Hz, 1H); 4.41 (d J=14 Hz, 1H).

EXAMPLE 86

17-Ethyl-1,14-dihydroxy-12-[2'-(4''-(p-hydrox ycinnamyloxy)-3''-methoxycyclohexyl)-1'-methyvinyl]-23,25-dimethoxy-13,19,21,27-tetramethyl-11,28-dioxa-4-azatricyclo[22.3.1.0⁴,⁹]octacos-18-ene-2,3,10,16-tetraone.

Prepared essentialy as described in Example 83 using p-(tert-butyldimethylsiloxy)cinnamyl trichloroacetimidate as the electrophile.

MASS (FAB) 930 (M+Li)

partial ¹H NMR δ: 7.22 (d J=10 Hz, 2H); 6.76 (d J=10 Hz, 2H); 6.51 (d J=16 Hz, 1H); 6.11 (dt J=16, 6Hz, 1H); 5.30 M, 5.17 m (brd J=3 Hz, 1H); 4.41 (d J=14 Hz, 1H).

EXAMPLE 87

17-Ethyl-1,14-dihydroxy-12-[2'-(4"-(p-hydroxyphenpropyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Prepared essentially as described in Examples 83(Step A), 56, 83(Step B) using p-(tert-butyldimethylsiloxy)cinnamyl trichloroacetimidate as the electrophile.

MASS (FAB) 949 (M+Na)

partial $^1$H NMR δ: 7.04 (d J=9 Hz, 2H); 6.72 (d J=9 Hz, 2H); 5.30 M, 5.17 m (brd J=3 Hz, 1H); 4.41 (d J=14 Hz, 1H).

EXAMPLE 88

17-Ethyl-1,14-dihydroxy-12-[2'-(4"-(m-hydroxycinnamyloxy)-3"-methoxycyclohexyl)-1'-methyvinyl]-23,25-dimethoxy-13,19,21,27-tetramethyl-11,28-dioxa-4-azatricyclo[22.3.1.0$^{4,9}$]octacos-18-ene-2,3,10,16-tetraone Prepared essentially as described in Example 83 using m-(tert-butyldimethylsiloxy)cinnamyl trichloroacetimidate as the electrophile.

MASS (FAB) 930 (M+Li)

partial $^1$H NMR δ: 7.17–6.63 (m, 5H); 6.52 (d J=16 Hz, 1H); 6.23 (dt J=16, 6 Hz, 1H); 5.69 (s, 1H); 5.30 M, 5.17 m (brd J=3 Hz, 1H) 4.41 (d J=14 Hz, 1H).

EXAMPLE 89

17-Ethyl-1,14-dihydroxy-12-[2'-(4"-(m-hydroxymethylbenzyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Step A: 17-Ethyl-1-hydroxy-14-(tert-butyldimethylsiloxy)-12-[2'-(4"-(m-hydroxymethylbenzyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone Prepared essentially as described in Example 70 (Step C) using m-(tert-butyldimethylsiloxymethyl)-benzyl trichloroacetimidate as the electrophile.

$^1$H NMR consistent with the desired structure.

Step B: 17-Ethyl-1,14-dihydroxy-12-[2'-(4"-(m-hydroxymethyl)benzyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-14-(tert-butyldimethylsiloxy)-12-[2'-(4"-(m-tert-butyldimethylsiloxymethyl)-benzyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (19.7 mg) in acetonitrile (0.5 ml) was added a solution of 2% HF in aqueous acetonitrile (40 ml), and the mixture stirred at room temperature. After 3.5 hours, the solution was diluted with ethyl acetate, extracted with saturated sodium bicarbondate solution and the organic phase dried over magnesium sulfate. Purification of the concentrate by flash chromatography on silica gel (ethyl acetate:hexane (1:1)+1% methanol) gave the title compound (6 mg).

MASS (FAB) 934 (M+Na)

partial $^1$H NMR δ: 7.41–7.22 (m, 4H); 5.30 M, 5.17 m (brd J=3 Hz, 1H); 4.41(d J=14 Hz, 1H).

EXAMPLE 90

17-Ethyl-1,14-dihydroxy-12-[2'-(4"-(m-hydroxycinnamyloxy)-3"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Step A: 17-Ethyl-1-hydroxy-14-(tert-butyldimethylsiloxy)-12-[2'-(3", 4"-di(tert-butyldimethylsiloxy)-cyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1,14-dihydroxy-12-[2'-(3",4"-dihydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (8.0 g) in dry methylene chloride (150 mL) was added an excess of 2,6-lutidine (4.8 mL) and the mixture was stirred at room temperature. After 10 minutes, tert-butyldimethylsilyl trifluoromethanesulfonate (7.57 mL) was added via syringe. After 1 hour the reaction mixture was diluted with ethyl acetate, extracted from 1N hydrochloric acid, washed with water, saturated sodium bicarbonate, brine, and the organic phase dried over magnesium sulfate. Removal of the solvent in vacuo gave the title compound (crude 12.5 g).

$^1$H NMR consistent with the desired structure.

Step B: 17-Ethyl-1-hydroxy-14-(tert-butyldimethylsiloxy)-12-[2'-(3",4"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-14-(tert-butyldimethylsiloxy)-12-[2'-(3",4"-di(tert-butyldimethylsiloxy)cyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (11.6 g) in methylene chloride (100 mL) was added a methanolic solution of p-toluenesulfonic acid (100 mL of a 10% solution w/v) and the mixture stirred at room temperature. After 30 minutes, the reaction was cooled to 0° C. and quenched by the careful addition of saturated sodium bicarbonate solution. The mixture was extracted with ethyl acetate and the organic portion washed with brine, dried over magnesium sulfate, and the concentrate purified by flash chromatography on silica gel (ethyl acetate:hexane (3:2) to give the title compound (8.4 g)

$^1$H NMR consistent with the desired structure.

Step C: 17-Ethyl-1-hydroxy-14-(tert-butyldimethylsiloxy)-12-[2'-(4"-hydroxy-3"-(tert-butyldimethylsiloxy)-cyclohexyl)-1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone and 17-Ethyl-1-hydroxy-14-(tert-butyldimethylsiloxy)-12-[2'-(4"-(tert-butyldimethylsiloxy)-3"-hydroxycyclohexyl)-1'-methylvinyl]-23,25-dimethoxy-13, 19, 21, 27-tetramethyl-11,28-diaoxa-4-azatricyclo[22.3.1.0$^{4,9}$]octacos-18-ene-2,3,10,16-tetraone To a solution of 17-ethyl-1-hydroxy-14-(tertbutyldimethylsiloxy)-12-[2'-(3", 4"-hydroxycylohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (8.17 g) in dry methylene chloride (92 mL) was added an excess of 2,6-lutidine (1.6 mL) and the mixture was stirred at 0° C. on an ice bath. After 10 minutes, tert-butyldimethylsilyl trifluoromethanesulfonate (2.1 mL) was added via syringe and the mixture allowed to warm slowly to room temperature. After 1 hour the reation mixture was diluted with ehtyl acetate, extracted from 1N hydrochloric acid, washed with water, saturated sodium bicarbonate, brine, and the organic phase dried over magnesium sulfate. Purification of the concentrate by flash chromatography on silica gel (10% acetone in hexane) gave the title compounds (3"ether: 1.81 g, 4"ether: 1.20 g).

$^1$H NMR consistent with the desired structure.

Step D: 17-Ethyl-1,14-dihydroxy-12-[2'-(4''-(m-hydroxycinnamyloxy)-3''-hydroxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone Prepared essentially as described in Example 83 using m-(tert-butyldimethylsiloxy)cinnamyl trichloroacetimidate as the electrophile.

MASS (FAB) 916 (M+Li)

partial $^1$H NMR δ: 7.22–6.67 (m, 5H); 6.52 (d J=16 Hz, 1H); 6.23 (dt J=16, 6 Hz, 1H); 5.30M, 5.17m (brd J=3 Hz, 1H); 4.41 (d J=14Hz, 1H).

EXAMPLE 91

17-Ethyl-1,14-dihydroxy-12-[2'-(4''-(3''',5'''-difluorocinnamyloxy)-3''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,-10,16-tetraone Prepared essentially as described in Example 90 using 3,5-difluorocinnamyl trichloroacetimidate as the electrophile.

MASS (FAB) 936 M+Li)

partial $^1$H NMR δ: 6.90–6.58 (m, 3H); 6.51(d J=16 Hz, 1H); 6.38 (dt J=26, 6 Hz, 1H); 5.30 M, 5.17 n (brd J=3 Hz, 1H); 4.41 (d J=14 Hz, 1H).

EXAMPLE 92

17-Ethyl-1,14-dihydroxy-12-[2'-(4''-(p-carboxybenzyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Step A: 17-Ethyl-1-hydroxy-14-(tert-butyldimethylsiloxy)-12-[2'-(4''-(p-(tert-butyldimethylsiloxymethyl)-benzyloxy)-3''-methoxycyclohexyl)-1'-methylvinyl]-23,25-dimethoxy-13,19,21,27-tetramethyl-11,28-dioxa-4-azatricyclo [22.3.1.0$^{4,9}$]octacos-18-ene-2,3,10,16-tetraone Prepared essentially as described in Example 44 using p-(tert-butyldimethylsiloxymethyl)-benzyl trichloroacetimidate as the electrophile.

$^1$H NMR consistent with the desired structure.

Step B: 17-Ethyl-1-hydroxy-14-(tert-butyldimethylsiloxy)-12-[2'-(4''-(p-hydroxymethyl)-benzyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-14-(tertbutyldimethylsiloxy)-12-[2'-(4''-(p-(tert-butyldimethylsiloxymethyl)-benzyloxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (420 mg) in methylene chloride (10 mL) was added a methanolic solution of p-toluenesulfonic acid (10 mL of a 10% solution w/v) and the mixture stirred at room temperature. After 5 minutes, the reaction was cooled to 0° C. and quenched by the careful addition of saturated sodium bicarbonate solution. The mixture was extracted with ethyl acetate and the organic portion washed with brine, dried over magnesium sulfate, and the concentrate purified by flash chromatography on silica gel (ethyl acetate:hexane (1:1+1% methanol) to give the title compound (316 mg).

$^1$H NMR consistent with the desired structure.

Step C: 17-Ethyl-1-hydroxy--14-(tert-butyldimethylsiloxy(-12-[2'-(4''-(p-formylbenzyloxy-3''-methoxycyclohexyl)-1'-methylvinyl]-23,25-dimethoxy-13,19,21,27-tetramethyl-11,28-dioxa-4-azatricyclo[22.3.1.9$^{4,9}$]octacos-18-ene-2,3,10.16-tetraone To a solution of 17-ethyl-1-hydroxy-14-(t-ertbutyldimethylsiloxy)-12-[2'-(4''-(p-hydroxymethyl)-benzyloxy-3''-methoxycyclohexyl)-1'methylvinyl]-23,25-dimethoxy-13,19,21,27-tetramethyl-11,28-dioxa4-azatricyclo[22.3.1.0$^{4,9}$]octacos-18-ene-2,3,10,16-tetraone (316 mg) in methylene chloride (6.0 mL) was added powdered 4 Å molecular sieves (20 mg) followed by 4-methylmorpholine-N-oxide (84.5 mg) and tetra-n-propylammonium perruthenate (5.5 mg), and the mixture stirred at room temperature. After 15 minutes, the mixture was filtered through a small silica gel column, washed with ethyl acetate, and the concentrated organics purified by flash chromatography on silica gel (ethyl acetate:hexane (1:1)+1% methanol) to give the title compound (282 mg).

$^1$H NMR consistent with the desired structure.

Step D: 17-Ethyl-1-hydroxy-14-(tert-butyldimethylsiloxy)-12-[2'-(4''-(p-carboxybenzyloxy -3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-end-2,3,10,16-tetraone To a solution of 17-ethyl-1-hydroxy-14-(tert-butyldimethylsiloxy-12-[2'-(4''-(p-formylbenzyloxy)-3''-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone (50 mg) in tert-butanol (1.0 mL) was added 2- methyl-2-butene (250 mL) followed by 0.5 mL of an aqueous solution of sodium chlorite (41 mg) and sodium dihydrogen phosphate (48 mg), and the mixture stirred at room temperature. After 1.5 hours, the mixture was concentrated and redissolved in ethyl acetate:hexane (1:1) and washed with water. The organic portion as dried over sodium sulfate, and the concentrate purified by flash chromatography on silica gel (ethyl acetate:hexane (4:1)+1% methanol+0.5% acetic acid) to give the title compound (43 mg).

$^1$H NMR consistent with the desired structure.

Step E: 17-Ethyl-1,14-dihydroxy-12-[2'-(4''-(p-carboxybenzyloxy)-3''-methoxycyclohexyl-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone Prepared essentially as described in Example 89 (Step B)

MASS (FAB) 933 (M+Li)

partial $^1$H NMR δ: 8.04 (d J=8 Hz, 2H); 7.44 (d J=8 Hz, 2H; 5.30 M, 5.17 m (brd J=3 Hz, 1H); 4.41 (d J=14 Hz, 1H); 4.73 (s, 2H).

EXAMPLE 93

17-Ethyl-1,14-dihydroxy-12-[2'-(4"-(m-carboxylbenzyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Prepared essentially as described in Example 92 using m-(tert-butyldimethylsiloxy)cinnamyl trichloroacetimidate as the electrophile.

MASS (FAB) 949 (M+Na)

partial $^1$H NMR δ: 8.07 (s, 1H); 7.97 (d J=8 Hz, 1H); 7.60 (d J=8 Hz, 1H); 7.41 (t J=8 Hz, 1H); 5.30 M, 5.17 m (brd J=3 Hz, 1H); 4.41 (d J=14 Hz, 1H).

EXAMPLE 94

17-Ethyl-1,14-dihydroxy-12-[2'-(4"-(m-carbomethoxybenzyloxy)-3"-methoxcyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1,14-dihydroxy-12-[2'-(4"-(m-carboxybenzyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (7 mg) in methylene chloride:methanol (2:1, 0.75 mL) at 0° C. was added a methylene chloride solution of trimethylsilyldiazomethane (10% by weight) until a yellow colored persisted. The mixture was then warmed to room temperature, concentrated in vacuo, and purified by flash chromatography on silica gel (acetone:hexane (1:2)) to give the title compound (5.5 mg).

MASS (FAB) 963 (M+Na)

partial $^1$H NMRδ: 8.03 (d J=8 Hz, 2H); 7.46 (d J=8 Hz, 2H); 5.30 M, 5.17 m (brd J=3 Hz, 1H); 4.41 (d J=14 Hz, 1H); 3.92 (s, 3H).

EXAMPLE 95

17-Ethyl-1,14-dihydroxy-12-[2'-(4"-(m-isopropylcarboxamidobenzyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Step A: 17-Ethyl-1-hydroxy-14-(tert-butyldimethylsiloxy)-(12-[2'-(4"-(m-isopropylcarboxamidobenzyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-14-(tertbutyldimethylsiloxy)-12-[2'-(4"-(m-carboxybenzyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (50 mg) in methylene chloride (1.0 mL) was added 4-benzotriazol-1-yloxy-tris(dimethylamino)phosphonium hexafluorophosphate (BOP, 32 mg) followed by triethylamine (14μL) and the mixture stirred at room temperature. After 10 minutes, isopropylamine (8.0 μL) was added, and the reaction stirred at room temperature for 12 hours. At this time the mixture was concentrated and purified by flash chromatography on silica gel (ethyl acetate:hexane (1:1)+1% methanol) to give the title compound (43 mg).

$^1$H NMR consistent with the desired structure.

Step B: 17-Ethyl-1,14-dihydroxy-12-[2'-(4"-(m-isopropylcarboxamidobenzyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Prepared essentially as described in Example 89 (Step B).

MASS (FAB) 974 (M+Li)

partial $^1$H NMR δ: 7.81 (s, 1H); 7.69 (d J=7 Hz, 1H); 7.44 (m, 2H); 6.00 (d J=8 Hz, 1H); 4.75 (s, 2H); 5.30 M, 5.17 m (brd J=3 Hz, 1H); 4.41 (d J=14 Hz, 1H).

EXAMPLE 96

17-Ethyl-1,14-dihydroxy-12-[2'-(4"-m-butylcarboxamidobenzyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Prepared essentially as described in Examples 95 (Step A), 83 (Step B) using n-butyl amine as the nucleophile.

MASS (FAB) 988 M+Li)

partial $^1$H NMR δ: 7.82 (s, 1H; 7.70 (d J=7 Hz, 1H); 7.44 (m, 2H); 6.18 (t J=5 Hz, 1H); 5.30 M, 5.17 m (brd J=3 Hz), 1H); 4.41 (d J=14 Hz, 1H).

EXAMPLE 98

17-Ethyl-1,14-dihydroxy-12-[2'-(4"-acetamidoxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Step A: 17-Ethyl-1-hydroxy-14-(tert-butylidimethylsiloxy)-12-[2'-(4"-carboxymethoxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-14-(tert-butyldimethylsiloxy)-12-[2'-(4"-ethanaloxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (311 mg) in tert-butanol (6.6 ml) and 2-methyl-2-butene (1.65 ml) was added sodium chlorite (273 mg) and sodium dihydrogen phosphate (272 mg) in water (2.7 ml) slowly. After 2 hours, the solvent was removed in vacuo, and the resulting residue was dissolved in water and acidified to pH 3 with 1N HCl. The aqueous layer was extracted with ethyl acetate (3×10 ml), and the combined organic portions washed with brine, dried over magenesium sulfate and purified by flash chromatography on silica gel (2% methanol in methylene chloride followed by 2% methanol in methylene chloride+0.5% acetic acid) to give the title compound (255 mg).

$^1$H NMR consistent with the desired structure.

Step B: 17-Ethyl-1-hydroxy-14-(tert-butyldimethylsiloxy)-12-[2'-(4"-acetamidoxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-14-(tert-butyldimethylsiloxy)-12-[2'-(4"-carboxymethoxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (24.3 mg) in methylene chloride:N,N-dimethylformamide (4:1, 0.5 mL) was added an admixture of 1-hydroxybenzotriazole hydrate (4.0 mg) and 1-(3-dimethylaminopropyl)-3-ethylcarbodiimide hydrochloride (6.7 mg) and the mixture atirred at room temperature. After 30 minutes, ammonium hydroxide (4.0 μL of a 25% aqueous solution) was added and the mixture stirred for an additional 4 hours. At this time, the solution was filtered over diatomaceous earth, diluted with ethyl acetate, and extracted with sodium bicarbonate. The organic portion was dried over magnesium sulfate, concentrated in vacuo, and purified by flash chromatography on silica gel (ethyl acetate:hexane (1:1)+1% methanol, then (2:1)+1% methanol) to give the title compound (14 mg).

$^1$H NMR consistent with the desired structure.

Step C: 17-Ethyl-1,14-dihydroxy-12-[2'-(4'-acetamidoxy-3''-methoxycyclohexyl)-1'-methylvinyl]23,25-dimethoxy-13,19,21,27-tetramethyl-11,28-dioxa-4-azatricyclo[22.3.1.0$^{4,9}$]octacos-18-ene-2,3,10,16-tetraone Prepared essentially as described in Example 83 (Step B).

MASS (FAB) 872 (M+Na)

partial $^1$H NMR δ: 7.79 (s, 2H); 5.30 M, 5.17 m (brd J=3 Hz, 1H); 4.41 (d J=14 Hz, 1H).

EXAMPLE 98

17-Ethyl-1,14-dihydroxy-12-[2'-(4''-carboxymethoxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Prepared essentially as described in Example 89 (Step B).

MASS (FAB) 863 (M+2Li)

partial $^1$H NMR δ: 5.24 (m, 2H); 5.02 (brd J=9 Hz), 1H); 4.94 (m, 1H); 4.44 (m, 2H).

EXAMPLE 99

17-Ethyl-1,14-dihydroxy-12-[2'-(4''-(N-phenyl acetamidoxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Prepared essentially as described in Example 95 (Step A) from 17-ethyl-1,14-dihydroxy-12-[2'-(4''-carboxymethoxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone using aniline as the nucleophile.

MASS (FAB) 932 (M+Li)

partial $^1$H NMR δ: 9.57 (brs, 1H); 7.61-7.05 (m, 5H); 5.26 (m, 2H); 4.42 (m, 2H).

EXAMPLE 100

17-Ethyl-1,14-dihydroxy-12-[2'-(4''-(N-benzyl acetamidoxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Prepared essentially as described in Example 97 (Step B) from 17-ethyl-1,14-dihydroxy-12-[2'-(4''-carboxymethoxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone using benzylamine as the nucleophile.

MASS (FAB) 946 (M+Li)

partial $^1$H NMR δ: 8.14 (brs, 1H); 7.30 (m, 5H); 5.21 (m, 2H); 3.04 (s, 2H).

EXAMPLE 101

17-Ethyl-1-hydroxy-12-[2'-(4''-carboxymethoxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Prepared essentially as described in Example 97 (Step A) from 17-ethyl-1-hydroxy-12-[2'-(4''-ethanaloxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone.

$^1$H NMR consistent with the desired structure.

EXAMPLE 102

17-Ethyl-1-hydroxy-12-[2'-(4''-(N-benzylam idoxymethoxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Prepared essentially as described in Example 95 (Step A) using benzylamine as the nucleophile.

MASS (FAB) 930 (M+Li)

partial $^1$H NMR δ: 8.19 (brs, 1H); 7.29 (m, 5H); 4.85 (brd J=8 Hz, 1H); 4.55 (m, 2H).

EXAMPLE 103

17-Ethyl-1-hydroxy-12-[2'-(4''-(N-methyltyrosine)amidoxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Prepared essentially as described in Example 95 (Step A) using tyrosine methyl ester hydrochloride as the nucleophile.

MASS (FAB) 1018 (M+Li)

partial $^1$H NMR δ: 6.98 (m, 2H); 6.73 (m, 2H); 4.02 (m, 2H); 3.69 (s, 3H).

EXAMPLE 104

17-Ethyl-1,14-dihydroxy-12-[2'-(4''-(2''''-(m-methylphenyl)-2''''-oxo-ethyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Prepared essentially as described in Example 77 using m-methylphenyl magnesium bromide as the nucleophile.

MASS (FAB) 931 (M+Li)

partial $^1$H NMR δ: 7.70 (m, 2H); 7.32 (m, 2H); 5.30 M, 5.17 m (brd J=3 Hz, 1H); 4.41 (d J=14 Hz, 1H); 2.39 (s, 3H).

EXAMPLE 105

17-Ethyl-1,14-dihydroxy-12-[2'-(4''-(-2''''-p-methylphenyl)-2''''-oxo-ethyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Prepared essentially as described in Example 77 using p-methylphenyl magnesium bromide as the nucleophile.

partial $^1$H NMR δ: 7.82 (d J=8 Hz, 2H); 7.23 (d J=8 Hz, 2H); 5.30 M, 5.17 m (brd J=3 Hz, 1H); 4.41 (d J=14 Hz), 1H); 2.33 (s, 3H).

EXAMPLE 106

17-Ethyl-1,14-dihydroxy-12-[2'--(4''-(2'''-phenyl-2'''-hydroxyethyloxy)-3''-methoxycyclohexyl)-1'-methylvinyl]-23,25-dimethoxy-13,19,21,27-tetramethyl-11,28-dioxa-4-azatricyclo[22.3.1.0^4,9]octacos-18-ene-2,3,10,16-tetraone Prepared essentially as described in Example 77 (Steps A,C) using phenyl magnesium bromide as the nucleophile.

MASS (FAB) 919 (M+Li)

partial $^1$H NMR δ: 7.32 (m, 5H); 5.30 M, 5.17 m (brd J=3 Hz, 1H); 4.41 (d J=14 Hz, 1H); 3.08 (d J=3 Hz, 1H).

EXAMPLE 107

17-Ethyl-1,14-dihydroxy-12-[2'-(4''-(2'''--(m-methylphenyl)-2'''-hydroxyethyloxy)-3''-methoxycyclohexyl)-1'-methylvinyl]-23,25-dimethoxy-13,19,21,27-tetramethyl-11,28-dioxa-4-azatricyclo[22.3.1.0^4,9]octacos-18-ene-2,3,10,16-tetraone Prepared essentially as described in Example 77 (Steps A,C) using m-methylphenyl magnesium bromide as the nucleophile.

MASS (FAB) 933 (M+Li)

partial $^1$H NMR δ: 7.25–7.03 (m, 4H); 5.30 M, 5.17 m (brd J=3 Hz, 1H); 4.41 (d J=14 Hz, 1H); 2.32 (s, 3H).

EXAMPLE 108

17-Ethyl-1,14-dihydroxy-12-[2'-(4''-(2'''-m-ethylphenyl)-2'''-oxo-ethyloxy)-3''-methoxycyclohexyl)-1-methylvinyl]-23,25-dimethoxy-13,19,21,27-tetramethyl-11,28-dioxa-4-azatricyclo[22.3.1.0^4,9]octacos-18-ene-2,3,10,16-tetraone Prepared essentially as described in Examples 77 (Step A), 56, 77 (Steps B,C) using m-vinylphenyl magnesium bromide as the nucleophile.

MASS (FAB) 945 (M+Li)

partial $^1$H NMR δ: 7.75 (s, 1H); 7.71 (d J=6 Hz, 1H); 7.37 (m, 2H); 5.30 M, 5.17 m (brd J=3 Hz, 1H); 4.41 (d J=14 Hz, 1H); 2.68 (q J=8 Hz, 2H); 1.22 (t J=8 Hz, 3H).

EXAMPLE 109

17-Ethyl-1,14-dihydroxy-12-[2'-(4''-(2'''-phenylethyloxy)-3''-methoxycyclohexyl)-1'-methylvinyl]-23,25-dimethoxy-13,19,21,27-tetramethyl-11,28-dioxa-4-azatricyclo[22.3.1.0^4,9 octacos-18-ene-2,3,10,16-tetraone Step A: 17-Ethyl-1-hydroxy-14-(tert-butyldimethylsiloxy)-12-[2'-(4''-(2'''-phenyl-2'''-trifluoroacetoxyethyloxy)-3''-methoxycyclohexyl)-1'-methylvinyl]-23,25-dimethoxy-13,19,21,27-tetramethyl-11,28-dioxa-4-azatricyclo[22.3.1.0^4,9]octacos-18-ene-2,3,10,16-tetraone To a solution of 17-ethyl-1-hydroxy-14-(tert-butyldimethylsiloxy)-12-[2'-(4''-(2'''-phenyl-2'''-hydroxyethyloxy)-3''-methoxycyclohexyl)-1'-methylvinyl]-23,25-dimethoxy-13,19,21,27-tetramethyl-11,28-dioxa-4-azatricyclo[22.3.1.0^4,9]octacos-18-ene-2,3,10,16-tetraone (23.3 mg) in methylene chloride (0.6 mL) was added triethylamine (12 μL) followed by trifluoroacetic anhydride (6.4 μL) and N,N-dimethylaminopyridine (3 mg) and the mixture stirred at room temperature. After 15 minutes, the reaction was quenched by the addition of saturated sodium bicarbonate solution, extracted with ethyl acetate, and the organics dried over magnesium sulfate. Purification of the concentrate by flash chromatography on silica gel (ethyl acetate:hexane (1:3)+1% methanol) gave the title compound (5 mg).

$^1$H NMR consistent with the desired structure.

Step B: 17-Ethyl-1,14-dihydroxy-12-[2'-(4''-(2'''-phenylethyloxy)-3''-methoxycyclohexyl)-1'-methylvinyl]-23,25-dimethoxy-13,19,21,27-tetramethyl-11,28-dioxa-4-azatricyclo[22.3.1.0^4,9]octacos-18-ene-2,3,10,16-tetraone Prepared essentially as described in Examples 56 and 83 (Step B).

MASS (FAB) 919 (M+Na)

partial $^1$H NMR δ: 7.30–7.22 (m, 5H); 5.30 M 5.17 m (brd J=3 Hz, 1H); 4.41 (d J=14 Hz, 1H).

EXAMPLE 110

17-Ethyl-1,14-dihydroxy-12-[2'--(4''-(2'''-phenyl-2'''-acetoxyethyloxy)-3''-methoxycyclohexyl)-1'-methylvinyl]-23,25-dimethoxy-13,19,21,27-tetramethyl-11,28-dioxa-4-azatricyclo[22.3.1.0^4,9]octacos-18-ene-2,3,10,16-tetraone Prepared essentially as described in Examples 104 (Step A) and 83 (Step B) using acetic anhydride as the electrophile.

partial $^1$H NMR δ: 7.33 (m, 5H); 6.03 (m, 1H); 5.30 M, 5.17 m (brd J=3 Hz, 1H); 4.41 (d J=14 Hz, 1H); 2.09 (s, 3H).

EXAMPLE 111

17-Ethyl-1,14-dihydroxy-12-[2'-(4''-(2'''-morpholinoethyloxy)-3''-methoxycyclohexyl)-1'-methylvinyl]-23,25-dimethoxy-13,19,21,27-tetramethyl-11,28-dioxa-4-azatricyclo[22.3.1.0^4,9]octacos-18-ene-2,3,10,16-tetraone Step A: 17-Ethyl-1-hydroxy-14-(tert-butyldimethylsiloxy)-12-[2'-(4''-(2'''-methanesulfonyloxyethyloxy)-3''-methoxycyclohexyl)-1'-methylvinyl]-23,25-dimethoxy-13,19,21,27-tetramethyl-11,28-dioxa-4-azatricyclo[22.3.1.0^4,9]octacos-18-ene-2,3,10,16-tetraone To a solution of 17-ethyl-1-hydroxy-14-(tert-butyldimethylsiloxy)-12-[2'-(4''-(2'''-hydroxyethyloxy)-3''-methoxycyclohexyl)-1'-methylvinyl]-23,25-dimethoxy-13,19,21,27-tetramethyl-11,28-dioxa-4-azatricyclo[22.3.1.0^4,9]octacos-18-ene-2,3,10,16-tetraone (80.8 mg) in methylene chloride (1.0 mL) was added triethylamine (23 μL) followed by methanesulfonyl chloride (7.2 μL) and the mixture stirred at room temperature. After 10 minutes, the reaction was quenched by the addition of saturated sodium bicarbonate solution, extracted with ethyl acetate, and the organic portion dried over magnesium sulfate. Purification of the concentrate by flash chromatography on silica gel (ethyl acetate:hexane (2:1)+1% methanol) gave the title compound (74 mg).

$^1$H NMR consistent with the desired structure.

Step B: 17-Ethyl-1-hydroxy-14-(tert-butyldimethylsiloxy)-12-[2'-(4''-(2'''-morpholinoethyloxy)-3''-methoxycyclohexyl)-1'-methylvinyl]-23,25-dimethoxy-13,19,21,27-tetramethyl-11,28-dioxa-4-azatricyclo[22.3.1.0^4,9]octacos-18-ene-2,3,10,16-tetraone To a solution of 17-ethyl-1-hydroxy-14-(tert-butyldimethylsiloxy)-12-[2'-(4''-(2'''-methanesulfonyloxyethyloxy)-3''-methoxycyclohexyl)-1'-methylvinyl]-23,25-dimethoxy-13,19,21,27-tetramethyl-11,28-dioxa-4-azatricyclo[22.3.1.0^4,9]octacos-18-ene-2,3,10,16-tetraone (26.5 mg) in dry tetrahydrofuran (0.3 mL) was added 200 μL of a sodium morpholine solution (prepared by addition of 10 μL morpholine to a suspension of 2.3 mg sodium hydride in 0.5 mL of tetrahydrofuran) and the mixture heated to 70° C. After 6 hours, the mixture is cooled to room temperature and quenched by the addition of saturated ammonium chloride solutin, extracted with ethyl acetate, and the organic portion dried over magnesium sulfate. Purification of the concentrate by flash chromatography on silica gel (ethyl acetate:hexane (2:1)+1% methanol, then 2% ammonium hydroxide, 5% methanol, in methylene chloride) gave the title compound (10 mg).

$^1$H NMR consistent with the desired structure.

Step C: 17-Ethyl-1,14-dihydroxy-12-[2'-(4''-(2'''-morpholinoethyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Prepared essentially as described in Example 83 (Step B).

MASS (FAB) 911 (M+Li)

partial $^1$H NMR δ: 5.30 M, 5.17 m (brd J=3 Hz, 1H); 4.41 (d J=14 Hz, 1H); 3.71 (m, 4H); 2.56 (m, 4H).

EXAMPLE 112

17-Ethyl-1,14-dihydroxy-12-[2'-(4''-(naphth-2-ylmethyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Prepared essentially as described in Example 44 using naphth-2-ylmethyl trichloroacetimidate as the electrophile and diethyl ether as the solvent. MASS (FAB) 938 (M+Li)

$^1$H NMR consistent with the desired structure.

EXAMPLE 113

17-Ethyl-1,14-dihydroxy-12--[2'-(4''-(4''',5'''-methylenedioxybenzyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Prepared essentially as described in Example 44 using 4,5-methylenedioxybenzyl trichloroacetimidate as the electrophile.

MASS (FAB) 932 (M+Li)

partial $^1$H NMR δ: 6.88 (s, 1H); 6.78 (d J=7 Hz, 1H); 6.74 (d J=7 Hz, 1H); 5.92 (s, 2H); 4.59 (d J=8 Hz, 1H); 4.52 (d J=8 Hz, 1H).

EXAMPLE 114

17-Ethyl-1,14-dihydroxy-12-[2'-(4''-(4'''-N,N,-dimethylaminophenyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Prepared essentially as described in Example 1 using tri(p-N,N-dimethylphenyl) bismuth diacetate as the arylating agent.

MASS (FAB) 917 (M+Li)

partial $^1$H NMR δ: 6.87 (d J=10 Hz, 2H); 6.68 (d J=10 Hz, 2H); 2.83 (s, 6H).

EXAMPLE 115

17-Ethyl-1,14-dihydroxy-12-[2'-(4''-(3'''-fluorophenyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Prepared essentially as described in Example 1 using tri(m-fluorophenyl) bismuth diacetate as the arylating agent.

MASS (FAB) 892 (M+Li)

$^1$H NMR consistent with the desired structure.

EXAMPLE 116

17-Ethyl-1,14-dihydroxy-12-[2'--(4''-(3'''-(2''''-dioxolanylphenyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Prepared essentially as described in Example 1 using tris(3-(2'-dioxolanyl)phneyl) bismuth diacetate as the arylating agent.

MASS (FAB) 946 (M+Li)

partial $^1$H NMR δ: 7.3-6.9 (m, 4H); 5.78 (s, 1H); 4.13-3.97 (m, 4H).

EXAMPLE 117

17-Ethyl-1,14-dihydroxy-12-[2'-(4''-(3'''-formylphenyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Prepared essentially as described in Example 90 (Step B) from 17-Ethyl-1,14-dihydroxy-12-[2'--(4''-(3'''-(2''''-dioxolanylphenyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone.

MASS (FAB) 902 (M+Li)

$^1$H NMR consistent with the desired structure.

EXAMPLE 118

17-Ethyl-1,14-dihydroxy-12-[2'-(4''-(3'''-carboxyphenyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Prepared essentially as described in Example 92 (Step D) from 17-ethyl-1,14-dihydroxy-12-[2'-(4''-(3'''-formylphenyloxy)-3''-methoxycyclohexyl)-1'methylvinyl]-23,25-dimethoxy-13,19,21,27-tetramethyl-11,28-dioxa-4-azatricyclo[22.3.1.0$^{4,9}$]octacos-18-ene-2,3,10,16-tetraone.

$^1$H NMR consistent with the desired structure.

EXAMPLE 119

17-Ethyl-1,14-dihydroxy-12-[2'-(4''-(3''',4'''-dimethoxyphenyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Prepared essentially as described in Example 1 using tris(3,4-dimethoxyphenyl) bismuth acetate as the alkylating agent.

MASS (FAB) 934 (M+Li).

partial ¹H NMR δ: 6.72 (d J=8 Hz., 1H); 6.56 (d J=2.5 Hz, 1H); 6.47 (dd J=8, 2.5 Hz, 1H); 4.57 (brd J=8 Hz, 1H); 4.39 (brd J=14.5 Hz, 1H); 3.79 (s, 3H); 3.77 (s, 3H).

EXAMPLE 120

17-Ethyl-1,14-dihydroxy-12-[2'-(4''-(4'''-trifluoromethylphenyloxy)-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone Prepared essentially as described in Example 1 using tris(4-fluoromethylphenyl) bismuth acetate as the alkylating agent.

MASS (FAB) 942 (M+Li).

partial ¹H NMR δ: 7.48 (d J=9.5 Hz, 2H); 6.98 (d J=9.5 Hz, 2H); 4.59 (brd J=5 Hz, 1H); 4.41 (brd, J=14.5 Hz, 1H).

EXAMPLE 121

17-Ethyl-1,14-dihydroxy-12-[2'-(-4''-(3''',5'''-bis(trifluoromethyl)phenyloxy)-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone Prepared essentially as described in Example 1 using tris(3,5-bis(trifluoromethyl)phenyl) bismuth acetate as the alkylating agent.

MASS (FAB) 1010 (M+Li).

partial ¹H NMR δ: 7.39 (s, 1H); 7.34 (s, 2H); 4.59 (brd J=5 Hz, 1H); 14.4 (brd J=14.5 Hz, 1H).

EXAMPLE 122

17-Ethyl-1-hydroxy-12-[2'-(4''-(4'''-methylphenyloxy)-3''-hydroxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone and

B.

17-Ethyl-1-hydroxy-12-[2'-(4''-hydroxy-3''-(4'''-methylphenyloxy)cyclohexyl)-1'-methylvinyl]-23,25-dimethoxy-13,19,21,27-tetramethy-11,28-dioxa-4-azatricyclo[22.3.1.0⁴,⁹]octacos-18-ene-2,3,10,16-tetraone Prepared essentially as described in Example 2 from 17-ethyl-1-hydroxy-12-[2'-(3'',4''-dihydroxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone using tri-(p-methylphenyl) bismuth diacetate as the alkylating agent.

A. (4''-ether):

partial ¹H NMR δ: 7.07 (d J=8.4 Hz, 2H); 6.83 (d J=8.4 Hz, 2H); 5.2–4.8 (m, 3H); 4.75 (s, 1H).

B. (3''-ether): MASS (FAB) 859 (M+Li)

partial ¹H NMR δ: 7.07 (d J=8.4 Hz, 2H); 6.82 (d J=8.4 Hz, 2H); 5.15–4.8 (m, 3H)

EXAMPLE 123

A.

17-Ethyl-1-hydroxy-12-[2'-(4''-(4'''-hydroxyphenyloxy)-3''-hydroxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone and

B.

17-Ethyl-1-hydroxy-12-[2'-(4''-hydroxy-3''-(4'''-hydroxyphenyloxy)cyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone Prepared essentially as described in Examples 122 and 90 (Step B) using tris-(p-(tert-butyldimethylsiloxy)-phenyl) bismuth diacetate as the alkylating agent.

A. (4''-ether): MASS (FAB) 862 (M+Li)

partial ¹H NMR d: 6.80 (d J=9 Hz, 2H); 6.72 (d J=9 Hz, 2H); 5.24 (brs, 1H); 5.1–4.8(m, 3H).

B. (3''-ether): MASS (FAB) 962 (M+Li)

partial ¹H NMR δ: 6.80 (d J=9 Hz, 2H); 6.72 (d J=9 Hz, 2H); 5.37 (brs, 1H); 5.1–4.9 (m, 3H).

EXAMPLE 124

A.

17-Ethyl-1-hydroxy-12-[2'-(4''-(4'''-hyroxymethylphenyloxy)-3''-hydroxycyclohexyl)-1'-methylvinyl]-23,25-dimethoxy-13,19,21,27-tetramethyl-11,28-dioxa-4-azatricyclo[22.3.1.0⁴,⁹ octacos-18-ene-2,3,10,16-tetraone and

B.

17-Ethyl-1-hydroxy-12-[2'-(4''-hydroxy-3''-(4'''-hydroxymethylphenyloxy)cyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone Prepared esssentially as described in Examples 122 and 90 (Step B) using tris-(p-(tert-butyldimethylsiloxymethyl)phenyl) bismuth diacetate as the alkylating agent.

A. (4''-ether): MASS (FAB) 875 (M+Li)

partial ¹H NMR δ: 7.26 (d J=10.2 Hz, 2H); 6.90 (d J=10.2 Hz, 2H); 5.1–4.8 (m, 3H); 4.59 (s, 2H).

B. (3''-ether): MASS (FAB) 875 (M+Li)

partial ¹H NMR δ: 7.26 (d J=9.75 Hz, 2H); 6.91 (d J=9.75 Hz, 2H); 5.1–4.8 (m, 3H); 4.59 (brs, 2H).

EXAMPLE 125

17-Ethyl-1-hydroxy-12-[2'-(4''-hydroxy-3''-(4'''-formylphenyloxy)cyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone Prepared essentially as described in Example 92 (Step C) from 17-ethyl-1-hydroxy-12-[2'-(4''-hydroxy-3''-(4'''-hydroxymethylphenyloxy)cyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone.

partial ¹H NMR δ: 9.80 (s, 1H); 7.83 (d J=8.5 Hz, 2H); 7.01 (d J=8.5 Hz, 2H); 5.20–4.95 (m, 2H); 4.87 (d J=9.4 Hz, 1H).

EXAMPLE 126

A.

17-Ethyl-1-hydroxy-12-[2'-(4''-(4'''-N,N-dimethylaminophenyloxy)-3''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone and

B.

17-Ethyl-1-hydroxy-12-[2'-(4''-hydroxy-3''-(4'''-N,N-dimethylaminophenyloxy)cyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Prepared essentially as described in Example 122 using tri-(p-N,N-dimethylaminophenyl) bismuth diacetate as the alkylating agent.

A. (4''-ether):
partial $^1$H NMR δ: 6.86 (d J=9.06 Hz, 2H); 6.68 (d J=9.06 Hz, 2H); 5.15–4.80 (m, 3H).

B. (3''-ether):
partial $^1$H NMR δ: 6.87 (d J=7.3 Hz, 2H); 6.68 (d J=7.3 Hz, 2H); 5.1–4.80 (m, 3H).

EXAMPLE 127

A.

17-Ethyl-1-hydroxy-12-[2'-(4''-phenyloxy)-3''-hydroxycyclohexyl)-1'-methylvinyl]-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone and

B.

17-Ethyl-1-hydroxy-12-[2'-(4''-hydroxy-3''-phenyloxy)-cyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Prepared essentially as described in Example 122 using tris-(phenyl) bismuth diacetate as the alkylating agent.

A. (4''-ether): MASS (FAB) 860 (M+Na)
partial $^1$H NMR d: 7.25 (m, 2H); 6.92 (m, 3H); 5.10M, 4.85m (t J=9 Hz, 2H); 5.00 (m, 2H).

B. (3''-ether): MASS (FAB) 860 (M+Na)
partial $^1$H NMR δ: 7.25 (m, 2H); 6.93 (m, 3H); 5.07 (t J=9 Hz, 2H); 4.97 (m, 2H); 4.82 (m, 2H); 4.52 (d J=5 Hz, 2H).

EXAMPLE 128

A.

17-Ethyl-1-hydroxy-12-[2'-(4''-(4'''-methoxyphenyloxy)-3''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone and

B.

17-Ethyl-1-hydroxy-12-[2'-(4''-hydroxy-3''-(4'''-methoxyphenyloxy)cyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Prepared essentially as described in Example 122 using tris-(p-methoxyphenyl) bismuth diacetate as the alkylating agent.

A. (4''-ether): MASS (FAB) 875 (M+Li)
B. (3''-ether): MASS (FAB) 875 (M+Li)
partial $^1$H NMR δ: 6.87 (m, 2H); 6.78 (m, 2H); 5.05 (t J=9 Hz, 2H); 3.72 (s, 3H).

EXAMPLE 129

A.

17-Ethyl-1-hydroxy-12-[2'-(4''-(3'''-methoxyphenyloxy)-3''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone and

B.

17-Ethyl-1-hydroxy-12-[2'-(4''-hydroxy-3''-(3'''-methoxyphenyloxy)cyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Prepared essentially as described in Example 122 using tris-(m-methoxyphenyl) bismuth diacetate as the alkylating agent.

A. (4''-ether): MASS (FAB) 875 (M+Li)
partial $^1$H NMR δ: 7.13 (t J=10 Hz, 1H); 6.51 (m, 3H); 5.00 (m, 4H); 3.72 (s, 3H).

B. (3''-ether): MASS (FAB) 875 (M+Li)
partial $^1$H NMR δ: 7.14 (t J=10 Hz, 1H); 6.49 (t J=10 Hz, 3H); 4.52 (d J=5 Hz, 1H); 4.38 m, 4.32 M (s, 1H); 3.75 (s, 3H).

EXAMPLES 130–161

Utilizing the general procedures described in Examples 1 to 129, the following compounds of Formula I (wherein $R^4$ is hydrogen, $R^5$ is methyl, ethyl, propyl or allyl and n is 2) are prepared from the appropriately substituted starting materials and reagents.

| EXAMPLE NO. | $R^1$ | $R^2$ | $R^3$ | $R^5$ |
| --- | --- | --- | --- | --- |
| 130 | HO–⟨C6H4⟩– | $CH_3$ | H | $CH_3CH_2$ |
| 131 | HO–⟨C6H4⟩– | $CH_2=CHCH_2-$ | OH | $CH_3CH_2$ |

-continued
| EXAMPLE NO. | R¹ | R² | R³ | R⁵ |
|---|---|---|---|---|
| 132 | 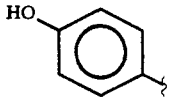 4-HO-C₆H₄- | CH₃ | OH | CH₂=CHCH₂- |
| 133 | 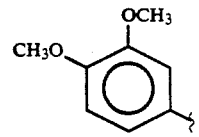 3,4-(CH₃O)₂-C₆H₃- | CH₃ | OH | CH₃CH₂CH₂ |
| 134 | 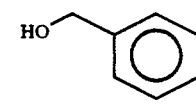 4-(HOCH₂)-C₆H₄- | CH₃ | OH | CH₃CH₂ |
| 135 | 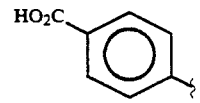 4-(HO₂C)-C₆H₄- | CH₃ | OH | CH₃CH₂ |
| 136 | 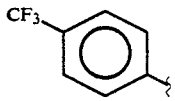 4-(CF₃)-C₆H₄- | CH₃ | OH | CH₃CH₂CH₂ |
| 137 | 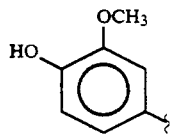 3-CH₃O-4-HO-C₆H₃- | CH₃ | H | CH₂=CHCH₂- |
| 138 | 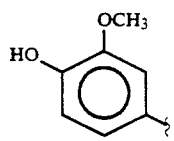 3-CH₃O-4-HO-C₆H₃- | CH₂=CHCH₂- | OH | CH₃CH₂ |
| 139 | 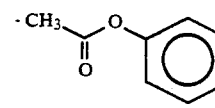 4-(CH₃C(O)O)-C₆H₄- | CH₃ | OH | CH₃CH₂ |
| 140 | 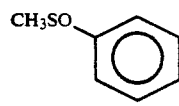 4-(CH₃S)-C₆H₄- | CH₃ | OH | CH₃CH₂ |
| 141 | 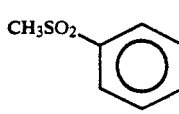 4-(CH₃SO₂)-C₆H₄- | CH₃ | OH | CH₃CH₂ |
| 142 | 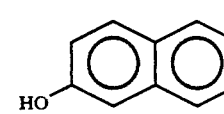 6-HO-naphth-2-yl | CH₃ | OH | CH₃CH₂ |
| 143 | 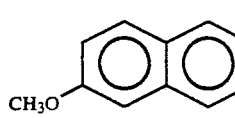 6-CH₃O-naphth-2-yl | CH₃ | OH | CH₃CH₂ |

-continued

| EXAMPLE NO. | R¹ | R² | R³ | R⁵ |
|---|---|---|---|---|
| 144 | 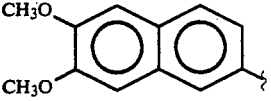 2,3-dimethoxynaphthyl | CH₃ | H | CH₂=CHCH₂— |
| 145 | 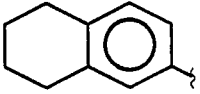 5,6,7,8-tetrahydronaphthyl | CH₃ | OH | CH₃CH₂ |
| 146 | 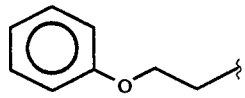 phenoxyethyl | CH₃ | OH | CH₃CH₂ |
| 147 | 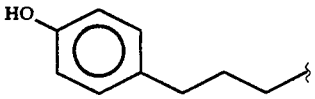 4-hydroxyphenylpropyl | CH₃ | OH | CH₃CH₂ |
| 148 | 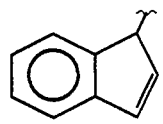 indenyl | CH₃ | OH | CH₃ |
| 149 | 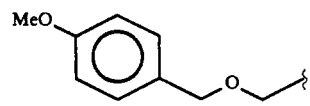 4-methoxybenzyloxyethyl | CH₃ | OH | CH₃CH₂ |
| 150 | 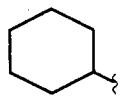 cyclohexyl | CH₃ | OH | CH₃CH₂ |
| 151 | 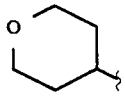 tetrahydropyranyl | CH₃ | OH | CH₃CH₂ |
| 152 | 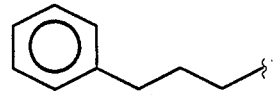 phenylpropyl | CH₃ | H | CH₃CH₂ |
| 153 | 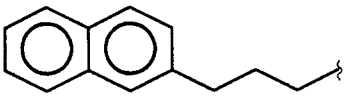 naphthylpropyl | CH₃ | H | CH₃CH₂ |
| 154 | 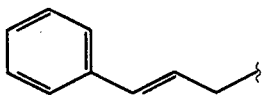 cinnamyl | CH₃CH₂ | OH | CH₃CH₂ |
| 155 | 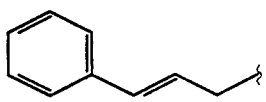 cinnamyl | (CH₃)₂CH | OH | CH₃CH₂ |
| 156 | 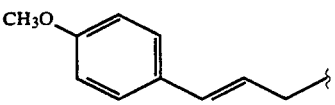 4-methoxycinnamyl | CH₃CH₂ | OH | CH₃CH₂ |

-continued

| EXAMPLE NO. | R¹ | R² | R³ | R⁵ |
|---|---|---|---|---|
| 157 | HO-C₆H₄-CH=CH-CH₂- (4-hydroxyphenyl allyl) | CH₃CH₂ | OH | CH₃CH₂ |
| 158 | CH₃O-C₆H₄-CH=CH-CH₂- (4-methoxyphenyl allyl) | CH₃CH₂CH₂ | OH | CH₃CH₂ |
| 159 | HO-C₆H₄-CH=CH-CH₂- | CH₃CH₂CH₂ | OH | CH₃CH₂ |
| 160 | HO-C₆H₄-CH=CH-CH₂- | CH₃CH₂CH₂ | OH | CH₃CH₂ |
| 161 | CH₃O-C₆H₄-CH=CH-CH₂- | (CH₃)₂CH | OH | CH₃CH₂ |
| 162 | HO-C₆H₄-CH=CH-CH₂- | (CH₃)₂CH | OH | CH₃CH₂ |
| 163 | H₂NCH₂CH₂— | CH₃ | OH | CH₃CH₂ |
| 164 | H₂NCH₂CH₂— | CH₃ | H | CH₃CH₂ |
| 165 | (CH₃)₂NCH₂CH₂— | CH₃ | OH | CH₃CH₂ |
| 166 | (CH₃)₂NCH₂CH₂— | CH₃ | H | CH₃CH₂ |
| 167 | CH₃NHCH₂CH₂— | CH₃ | OH | CH₃CH₂ |
| 168 | CH₃NHCH₂CH₂— | CH₃ | H | CH₃CH₂ |

EXAMPLE 120

T-Cell Proliferation Assay

1. Sample Preparation

The compounds to be assayed were dissolved in absolute ethanol at 1 mg/ml.

2. Assay

Spleens from C57B1/6 mice were taken under sterile conditions and gently dissociated in ice-cold RPMI 1640 culture medium (GIBC), Grand Island, N.Y.) supplemented with 10% heat-inactivated fetal calf serum (GIBO)). Cells were pelleted by centrifugation at 1500 rpm for 8 minutes. Contaminating red cells were removed by treating the pellet with ammonium chloride lysing buffer (GIBO)) for 2 minutes at 4° C. Cold medium was added and cells were again centrifuged at 1500 rpm for 8 minutes. T lymphocytes were then isolated by separation of the cell suspension on nylon wool columns as follows: Nylon wool columns were prepared by packing approximately 4 grams of washed and dried nylon wool into 20 ml plastic syringes. The columns were sterilized by autoclaving at 25° F. for 30 minutes. Nylon wool columns were wetted with warm (37° C.) culture medium and rinsed with the same medium. Washed spleen cells resuspended in warm medium were slowly applied to the nylon wool. The columns were then incubated in an upright position at 37° C. for 1 hour. Non-adherent T lymphocytes were eluted from the columns with warm culture medium and the cell suspensions were spun as above.

Purified T lymphocytes were resuspended at $2.5 \times 10^5$ cells/ml in complete culture medium composed of RPMI 1640 medium with 10% heat-inactivated fetal calf serum, 100 mM glutamine, 1 mM sodium pyruvate, $2 \times 10^5$ M 2-mercaptoethanol and 50 µg/ml gentamycin. Ionomycin was added at 250 ng/ml and PMA at 10 ng/ml. The cell suspension was immediately distributed into 96 well flat-bottom microculture plates (Costar) at 200 µl/well. The various dilustions of the compound to be tested were then added in triplicate wells at 20 µl/well. The compound 17-allyl-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone was used as a standard. The culture plates were then incubated at 37° C. in a humidified atmosphere of 5% CO₂-95% air for 44 hours. The proliferation of T lymphocytes was assessed by measurement of tritiated thymidine incorporation. After 44 hours of culturing, the cells were pulse-labelled with 2 µCi/well of tritiated thymidine (NEN, Cambridge, Mass.). After another 4 hours of incubation, cultures were harvested on glass fiber filters using a multiple sample harvester. Radioactivity of filter discs corresponding to individual wells was measured by standard liquid scintillation counting methods (Betacounter). Mean counts per minute of replicate wells were calculated and the results expressed as concentration of compound required to inhibit tritiated thymidine uptake of T-cells by 50%

A selection of compounds were tested according to the previous procedure. The title compounds of the following Examples had activity in inhibiting the proliferation of T-cells in the aforementioned assay:

1, 2A, 2B, 3, 4, 5, 6A, 6B, 7, 8A, 8B, 9, 10A, 10B, 11, 12A, 12B, 13, 14, 15A, 15B, 16, 17, 18, 19, 20, 21, 22, 23, 24, 25, 26, 43, 44, 45, 46A, 46B, 47B, 48A, 49A, 49B, 50A, 50B, 51A, 51B, 52, 53, 54A, 54B, 55, 56, 57, 58, 59, 60, 61, 64, 70, 73, 76, 77, 77B, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122A, 122B, 123A, 123B, 124A, 124B, 125, 126A, 126B, 127A, 127B, 128A, 128B, 129A, and 129B.

The results of this assay are representative of the intrinsic immunosuppressive activity of the compounds of the present invention.

While the foregoing specification teaches the principles of the present invention, with examples provided for the purpose of illustration, it will be understood that the practice of the invention encompasses all of the casual variation, adaptations, modifications, deletions, or additions of procedures and protocols described herein, as come within the scope of the following claims and its equivalents.

What is claimed is:

1. A compound of formula I:

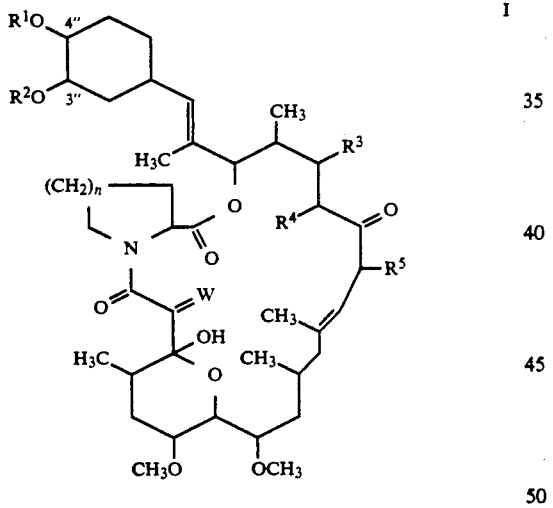

or a pharmaceutically acceptable salt thereof, wherein:
$R^1$ and $R^2$ are independently selected from
  (1) hydrogen;
  (2) phenyl;
  (3) substituted phenyl in which the substituents are X, Y and Z;
  (4) 1- or 2- naphthyl;
  (5) substituted 1- or 2- naphthyl in which the substituents are X, Y and Z;
  (6) biphenyl;
  (7) substituted biphenyl in which the substituents are X, Y and Z;
  (8) $C_{1-10}$ alkyl;
  (9) substituted $C_{1-10}$ alkyl in which one or more substituents(s) is (are) selected from:
    (a) hydroxy,
    (b) oxo,
    (c) $C_{1-6}$-alkoxy,
    (d) phenyl-$C_{1-3}$alkoxy,
    (e) substituted phenyl-$C_{1-3}$alkoxy, in which the substituents on phenyl are X, Y and Z,
    (f) —OCO—$C_{1-6}$alkyl,
    (g) —$NR^6R^7$, wherein $R^6$ and $R^7$ are independently selected from
      (i) hydrogen,
      (ii) $C_{1-10}$alkyl unsubstituted for substituted with one or more of the substituent(s) selected from:
        (a') phenyl, which is unsubstituted or substituted with X, Y and Z,
        (b') —OH,
        (c') $C_{1-6}$alkoxy,
        (d') —$CO_2H$,
        (e') —$CO_2$—$C_{1-6}$alkyl,
        (f') —$C_{3-7}$cycloalkyl, and
        (f') —$OR^{11}$,
      (iii) $C_{3-10}$alkenyl unsubstituted or substituted with one or more of the substituent(s) selected from:
        (a') phenyl, which is unsubstituted or substituted with X, Y and Z,
        (b') —OH
        (c') $C_{1-6}$alkoxy,
        (d') —$CO_2H$,
        (e') —$CO_2$—$C_{1-6}$alkyl,
        (f') —$C_{3-7}$cycloalkyl, and
        (g') —$OR^{11}$,
      (iv) or where $R^6$ and $R^7$ and the N to which they are attached can form a 3–7-membered saturated heterocyclic ring, unsubstituted or substituted with $C_{1-6}$ alkyl or phenyl, the ring being selected from the group consisting of: aziridine, morpholine, thiomorpholine, thiomorpholine-oxide, thiomorpholine-dioxide, piperidine, pyrrolidine, and piperizine,
    (h) —$NR^6CO$—$C_{1-6}$alkyl—$R^7$, wherein $R^6$ is as defined above,
    (i) —$NR^6CO_2$—$C_{1-6}$alkyl—$R^7$,
    (j) —$NR^6CONR^6R^7$,
    (k) —$OCONR^6R^7$,
    (l) —$COOR^6$,
    (m) —CHO,
    (n) phenyl,
    (o) substituted phenyl in which the substituents are X, Y and Z,
    (p) phenyloxy,
    (q) substituted phenyloxy in which the substituents are X, Y and Z,
    (r) 1- or 2- naphthyl,
    (s) substituted 1- or 2- naphthyl in which the substituents are X, Y and Z,
    (t) biphenyl
    (u) substituted biphenyl in which the substituents are X, Y and Z;
    (v) —$OR^{11}$, and
    (w) —$S(O)_p$—$C_{1-6}$alkyl;
  (10) $C_{3-10}$ alkenyl;
  (11) substituted $C_{3-10}$ alkenyl in which one or more substituent(s) is(are) selected from:
    (a) hydroxy,
    (b) oxo,
    (c) $C_{1-6}$alkoxy,
    (d) phenyl-$C_{1-3}$alkoxy,
    (e) substituted phenyl-$C_{1-3}$alkoxy, in which the substituents on phenyl are X, Y and Z,
    (f) —OCO—$C_{1-6}$alkyl, (g) —NR$^6$R$^7$, wherein R$^6$ and R$^7$ are as defined above (h) —NR$^6$CO—C$_{1-6}$alkyl, wherein R$^6$ is as defined above, (i) —COOR$^6$, wherein R$^6$ is as defined above, (j) —CHO, (k) phenyl, (l) substituted phenyl in which the substients are X, Y and Z, (m) 1- or 2-naphthyl, (n) substituted 1- or 2-naphthyl in which the substituents are X, Y and Z, (o) biphenyl, (p) substituted biphenyl in which the substituents are X, Y and Z, (q) —OR$^{11}$, and (r) —S(O)$_p$—C$_{1-6}$alkyl;

(12) C$_{3-10}$alkynyl;

(13) substituted C$_{3-10}$alkynyl in which one or more substituent(s) is(are) selected from:

(a) hydroxy, (b) oxo, (c) C$_{1-6}$alkoxy, (d) phenyl-C$_{1-3}$alkoxy, (e) substituted phenyl-C$_{1-3}$alkoxy, in which the substituents onphenyl are X, Y and Z, (f) —OCO—C$_{1-6}$alkyl, (g) —NR$^6$R$^7$, wherein R$^6$ and R$^7$ are as defined above, (h) —NR$^6$CO—C$_{1-6}$alkyl, wherein R$^6$ is as defined above, (i) —COOR$^6$, wherein R$^6$ is as defined above, (j) —CHO, (k) phenyl, (l) substituted phenyl in which the substituents are X, Y and Z, (m) 1- or 2-naphthyl, (n) substituted 1- or 2-naphthyl in which the substituents are X, Y and Z, (o) biphenyl, (p) substituted biphenyl in which the substituents are X, Y and Z, and (q) —OR$^{11}$;

with the proviso that R$^1$ and R$^2$ are not simultaneously hydrogen, methyl or combinations thereof and the further proviso that R$^1$ is not benzyl;

R$^3$ is hydrogen, hydroxy, —OR$^{11}$ or C$_{1-6}$ alkoxy;

R$^4$ is hydrogen, or R$^3$ and R$^4$ taken together form a double bond;

R$^5$ is methyl, ethyl, propyl or allyl;

R$^{11}$ is selected from:

(a) —PO(OH)O$^-$M$^+$, whereim M$^+$ is a positively charged inorganic or organic counterion, selected from the group consisting of: ammonium, sodium, lithium, postassium, calcium, magnesium, dicyclohexylamine, N-methyl-D-glucamine, arginine and lysine, (b) —SO$_3$$^-$M$^+$, (c) —CO(CH$_2$)$_q$CO$_2$$^-$M$^+$, wherein q is 1–3, and (d) —CO—C$_{1-6}$alkyl-NR$^6$R$^7$, wherein R$^6$ and R$^7$ are as defined above and the alkyl is unsubstituted or substituted with one or more substituents selected from:

(i) hydroxy, (ii) C$_{1-6}$alkoxy, (iii) —NR$^{16}$R$^{17}$, wherein R$^{16}$ and R$^{17}$ are independently selected from:

(a') hydrogen, and (b') C$_{1-6}$alkyl, (iv) —COOR$^6$, wherein R$^6$ is as defined above, (v) phenyl, (vi) substituted phenyl in which the substituents are X, Y and Z, (vii) —SH, and (viii) —S—C$_{1-6}$alkyl;

W is O or (H, OH);

X, Y and Z independently are selected from:

(a) hydrogen, (b) c$_{1-7}$ alkyl, (c) C$_{2-6}$ alkenyl, (d) halogen, (e) —(CH$_2$)$_m$—NR$^6$R$^7$, wherein R$^6$ and R$^7$ are as defined above, and m is 0 to 2, (f) —CN, (g) —CHO, (h) —CF$_3$, (i) —SR$^8$, wherein R$^8$ is hydrogen, C$_{1-6}$alkyl, trifluoromethyl, or phenyl, (j) —SOR$^8$, wherein R$^8$ is as defined above, (k) —SO$_2$R$^8$, wherein R$^8$ is as defined above, (l) —CONR$^6$R$^7$, wherein R$^6$ and R$^7$ are as defined above, (m) R$^9$O(CH$_2$)$_m$— wherein R$^9$ is hydrogen, C$_{1-3}$ alkyl, hydroxy-C$_{2-3}$alkyl, trifluoromethyl, phenyl or naphthyl and m is as defined above, (n) —CH(OR$^{12}$)(OR$^{13}$), wherein R$^{12}$ and R$^{13}$ are C$_{1-3}$alkyl or taken together form an ethyl or propyl bridge, (o)

wherein R$^9$ and m are as defined above, and (p)

wherein R$^9$ and m are as defined above, and (q) —OR$^{11}$;

or any two of adjacent X, Y and Z can be joined to form a ring selected from the group consisting of: dioxolanyl, dihydrofuranyl, dihydropyranyl, and dioxanyl; and n is 1 or 2.

2. The compound of claim 1 wherein the absolute configuration of formula I is as defined in formula III:

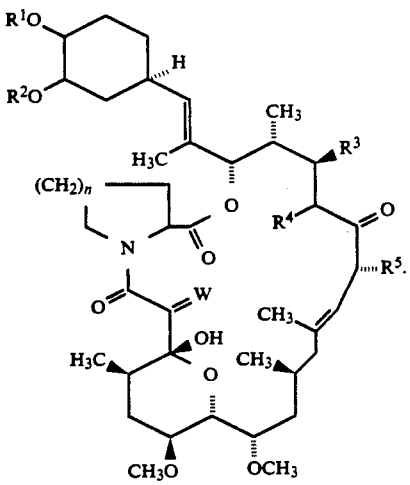

III

3. The compound of claim 1 wherein:
$R^1$ and $R^2$ are independently selected from:
(1) hydrogen;
(2) methyl;
(3) phenyl;
(4) substituted phenyl in which the substituents are X, Y and Z;
(5) 1- or 2- naphthyl;
(6) substituted 1- or 2- naphthyl in which the substituents are X, Y and Z;
(7) biphenyl; and
(8) substituted and biphenyl in which the substituents are X, Y and Z;
with the proviso that $R^1$ and $R^2$ are not simultaneously hydrogen, methyl or combinations thereof;
$R^3$ is hydrogen, hydroxy, or $C_{1-6}$ alkoxy;
$R^4$ is hydrogen, or $R^3$ and $R^4$ taken together form a double bond;
$R^5$ is methyl, ethyl, propyl or allyl;
$R^{11}$ is selected from:
(a) —PO(OH)O$^-$M$^+$, wherein M$^+$ is a positively charged inorganic or organic counterion, selected from the group consisting of: ammonium, sodium, lithium, potassium, calcium, magnesium, dicyclohexylamine, N-methyl-D-glucamine, arginine and lysine,
(b) —SO$_3^-$M$^+$,
(c) —CO(CH$_2$)$_q$CO$_2^-$M$^+$, wherein q is 1-3, and
(d) —CO—C$_{1-6}$alkyl—NR$^6$R$^7$, wherein R$^6$ and R$^7$ are as defined below and the alkyl is unsubstituted or substituted with one or more substituents selected from:
(i) hydroxy,
(ii) C$_{1-6}$alkoxy,
(iii) —NR$^{16}$R$^{17}$, wherein R$^{16}$ and R$^{17}$ are independently selected from:
(a') hydrogen, and
(b') C$_{1-6}$alkyl,
(iv) —COOR$^6$, wherein R$^6$ is as defined below,
(v) phenyl,
(vi) substituted phenyl in which the substituents are X, Y and Z,
(vii) —SH, and
(viii) —S—C$_{1-6}$alkyl;
W is O or (H, OH);
X, Y and Z are independently, selected from:
(a) hydrogen,
(b) C$_{1-7}$ alkyl,
(c) C$_{2-6}$ alkenyl,
(d) halogen,
(e) —(CH$_2$)$_m$—NR$^6$R$^7$, wherein R$^6$ and R$^7$ are, independently selected from
(i) hydrogen, or
(ii) C$_{1-6}$ alkyl unsubstituted or substituted with phenyl, and m is 0 to 2,
(f) —CN,
(g) —CHO,
(h) —CF$_3$,
(i) —SR$^8$, wherein R$^8$ is hydrogen, C$_{1-6}$alkyl, trifluoromethyl, or phenyl,
(j) —SOR$^8$, wherein R$^8$ is as defined above,
(k) —SO$_2$R$^8$, wherein R$^8$ is as defined above,
(l) —CONR$^6$R$^7$, wherein R$^6$ and R$^7$ are as defined above,
(m) R$^9$O(CH$_2$)$_m$— wherein R$^9$ is hydrogen, C$_{1-3}$ alkyl, hydroxy-C$_{2-3}$alkyl, trifluoromethyl, phenyl or naphthyl and m is as defined above,
(n) —CH(OR$^{12}$)(OR$^{13}$), wherein R$^{12}$ and R$^{13}$ are C$_{1-3}$ alkyl or taken together form an ethyl or propyl bridge,
(o)

$$R^9\overset{O}{\underset{\|}{C}}O(CH_2)_m-$$

wherein R$^9$ and m are as defined above, and
(p)

$$R^9O\overset{O}{\underset{\|}{C}}(CH_2)_m-$$

wherein R$^9$ and m are as defined above, and
(q) -OR$^{11}$;
or any two of adjacent X, Y and Z can be joined to form a ring selected from the group consisting of: dioxolanyl, dihydrofuranyl, dihydropyranyl, and dioxanyl; and
n is 1 or 2.
4. The compound of claim 1 wherein:
$R^1$ and $R^2$ are independently selected from:
(1) hydrogen;
(2) C$_{1-10}$ alkyl;
(3) substituted C$_{1-10}$ alkyl in which one or more substituent(s) is(are) selected from:
(a) hydroxy,
(b) oxo,
(c) C$_{1-6}$-alkoxy,
(d) phenyl-C$_{1-3}$alkoxy,
(e) substituted phenyl-C$_{1-3}$alkoxy, in which the substituents on phenyl are X, Y and Z,
(f) —OCO—C$_{1-6}$alkyl,
(g) —NR$^6$R$^7$, wherein R$^6$ and R$^7$ are independently selected from
(i) hydrogen,
(ii) C$_{1-10}$alkyl unsubstituted or substituted with one or more of the substituent(s) selected from:
(a') phenyl, which is unsubstituted or substituted with X, Y and Z,
(b') —OH,
(c') C$_{1-6}$alkoxy,
(d') —CO$_2$H,
(e') —CO$_2$—C$_{1-6}$alkyl, (f') —$C_{3-7}$cycloalkyl, and
(g') —$OR^{11}$,
(iii) $C_{3-10}$alkenyl unsubstituted or substituted with one or more of the substituent(s) selected from:
(a') phenyl, which is unsubstituted or substituted with X, Y and Z,
(b') —OH,
(c') $C_{1-6}$alkoxy,
(d') —$CO_2H$,
(e') —$CO_2$—$C_{1-6}$alkyl,
(f') —$C_{3-7}$cycloalkyl, and
(g') —$OR^{11}$,
(iv) or where $R^6$ and $R^7$ and the N to which they are attached can form a 3-7-membered saturated heterocyclic ring, unsubstituted or substituted with $C_{1-6}$ alkyl or phenyl, the ring being selected from the group consisting of: aziridine, morpholine, thiomorpholine, thiomorpholine-oxide, thiomorpholine-dioxide, piperidine, pyrrolidine, and piperazine,
(h) —$NR^6CO$—$C_{1-6}$alkyl-$R^7$, wherein $R^6$ is as defined above,
(i) —$NR^6CO_2$—$C_{1-6}$alkyl-$R^7$,
(j) —$NR^6CONR^6R^7$,
(k) —$OCONR^6R^7$,
(l) —$COOR^6$,
(m) —CHO,
(n) phenyl,
(o) substituted phenyl in which the substituents are X, Y and Z,
(p) phenyloxy,
(q) substituted phenyloxy in which the substitutents are X, Y and Z,
(r) 1- or 2- naphthyl,
(s) substituted 1- or 2-naphthyl in which the substituents are X, Y and Z,
(t) biphenyl
(u) substituted biphenyl in which the substituents are X, Y and Z;
(v) —$OR^{11}$, and
(w) —$S(O)_p$—$C_{1-6}$alkyl;
(4) $C_{3-10}$ alkenyl;
(5) substituted $C_{3-10}$ alkenyl in which one or more substituent(s) is(are) selected from:
(a) hydroxy,
(b) oxo,
(c) $c_{1-6}$alkoxy,
(d) phenyl-$C_{1-3}$alkoxy,
(e) substituted phenyl-$C_{1-3}$alkoxy, in which the substituents on phenyl are X, Y and Z,
(f) —OCO—$C_{1-6}$alkyl,
(g) —$NR^6R^7$, wherein $R^6$ and $R^7$ are as defined above
(h) —$NR^6CO$—$C_{1-6}$alkyl, wherein $R^6$ is as defined above,
(i) —$COOR^6$, wherein $R^6$ is as defined above,
(j) —CHO,
(k) phenyl,
(l) substituted phenyl in which the substituents are X, Y and Z,
(m) 1- or 2-naphthyl,
(n) substituted 1- or 2-naphthyl in which the substituents are X, Y and Z,
(o) biphenyl,
(p) substituted biphenyl in which the substitutents are X, Y and Z,
(q) —$OR^{11}$, and
(r) —$S(O)_p$—$C_{1-6}$alkyl;
(6) $C_{3-10}$alkynyl;
(7) substituted $C_{3-10}$alkynyl in which one or more substituent(s) is(are) selected from:
(a) hydroxy,
(b) oxo,
(c) $C_{1-6}$alkoxy,
(d) phenyl-$C_{1-3}$alkoxy,
(e) substituted phenyl-$C_{1-3}$alkoxy, in which the substituents on phenyl are X, Y and Z,
(f) —OCO—$C_{1-6}$alkyl,
(g) —$NR^6R^7$, wherein $R^6$ and $R^7$ are as defined above,
(h) —$NR^6CO$—$C_{1-6}$alkyl, wherein $R^6$ is as defined above,
(i) —$COOR^6$, wherein $R^6$ is as defined above,
(j) —CHO,
(k) phenyl,
(l) substituted phenyl in which the substituents are X, Y and Z,
(m) 1- or 2-naphthyl,
(n) substituted 1- or 2-naphthyl in which the substituents are X, Y and Z,
(o) biphenyl,
(p) substituted biphenyl in which the substituents are X, Y and Z, and
(q) —$OR^{11}$;
with the proviso that $R^1$ and $R^2$ are not simultaneously hydrogen, methyl or combinations thereof;
$R^3$ is hydrogen, hydroxy, —$OR^{11}$ or $C_{1-6}$ alkoxy;
$R^4$ is hydrogen, or $R^3$ and $R^4$ taken together form a double bond;
$R^5$ is methyl, ethyl, propyl or allyl;
$R^{11}$ is selected from:
(a) —$PO(OH))O^-M^+$, wherein $M^+$ is a positively charged inorganic or organic counterion, selected form the group consisting of: ammonium, sodium, lithium, potassium, calcium, magnesium, dicyclohexylamine, N-methyl-D-glucamine, arginine and lysine,
(b) —$SO_3^-M^+$,
(c) —$CO(CH_2)_qCO_2^-M^+$, wherein q is 1-3, and
(d) —CO—$C_{1-6}$alkyl-$NR^6R^7$, wherein $R^6$ and $R^7$ are as defined above and the alkyl is unsubstituted or substituted with one or more substituents selected from:
(i) hydroxy,
(ii) $C_{1-6}$alkoxy,
(iii) —$NR^{16}R^{17}$, wherein $R^{16}$ and $R^{17}$ are independently selected from:
(a') hydrogen, and
(b') $C_{1-6}$alkyl,
(iv) —$COOR^6$, wherein $R^6$ is as defined above,
(v) phenyl,
(vi) substituted phenyl in which the substituents are X, Y and Z,
(vii) —SH, and
(viii) —S—$C_{1-6}$alkyl;
W is O or (H, OH);
X, Y and Z independently are selected from:
(a) hydrogen,
(b) $C_{1-7}$ alkyl,
(c) $C_{2-6}$ alkenyl,
(d) halogen,
(e) —$(CH_2)_m$—$NR^6R^7$, wherein $R^6$ and $R^7$ are as defined above, and m is 0 to 2,
(f) —CN,
(g) —CHO, (h) —CF₃,
(i) —SR⁸, wherein R⁸ is hydrogen, C₁₋₆alkyl, trifluoromethyl, or phenyl,
(j) —SOR⁸, wherein R⁸ is as defined above,
(k) —SO₂R⁸, wherein R⁸ is as defined above,
(l) —CONR⁶R⁷, wherein R⁶ and R⁷ are as defined above,
(m) R⁹O(CH₂)ₘ— wherein R⁹ is hydrogen, C₁₋₃ alkyl, hydroxy-C₂₋₃alkyl, trifluoromethyl, phenyl or naphthyl and m is as defined above,
(n) —CH(OR¹²)(OR¹³), wherein R¹² and R¹³ are C₁₋₃alkyl or taken together form an ethyl or propyl bridge,
(o)

wherein R⁹ and m are as defined above, and
(p)

wherein R⁹ and m are as defined above, and
(q) —OR¹¹;
or any two of adjacent X, Y and Z can be joined to form a ring selected from the gorup consisting of: dioxolanyl, dihydrofuranyl, dihydropyranyl, and dioxanyl; and
n is 1 or 2.

5. A compound which is selected from the group consisting of:

17-ethyl-1,14-dihydroxy-12-[2'-(4''-phenyloxy-3''-methoxycyclohexyl)-1'-methylvinyl]-23,25-dimethoxy-13,19,21,27-tetramethyl-11,28-dioxa-4-azatricyclo [22.3.1.0⁴,⁹]octacos-18-ene-2,3,10,16-tetraone;

17-ethyl-1,14-dihydroxy-12-[2'-(3''-phenyloxy-4''-hydroxycyclohexyl)-1'-methylvinyl]-23,25-dimethoxy-13,19,21,27-tetramethyl-11,28-dioxa-4-azatricyclo [22.3.1.0⁴,⁹]octacos-18-ene-2,3,10,16-tetraone;

17-ethyl-1,14-dihydroxy-12-[2'-(4''-phenyloxy-3''-hydroxycyclohexyl)-1''-methylvinyl]-23,25-dimethoxy-13,19,21,27-tetramethyl-11,28-dioxa-4-azatricyclo [22.3.1.0⁴,⁹]octacos-18-ene-2,3,10,16-tetraone;

17-ethyl-1,14-dihydroxy-12-[2'-(4''-(4'''-fluorophenyloxy)-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(4''-(4'''-chlorophenyloxy)-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17ethyl-1,14-dihydroxy-12-[2'-(4''-(4'''-methylphenyloxy)-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(3''-(4'''-methylphenyloxy)-4''-hydroxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(4''-(4'''-methylphenyloxy)-3''-hydroxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone.

17-ethyl-1,14-dihydroxy-12-[2'-(4''-(4'''-phenoxyphenyloxy)-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(4''-(4'''-phenoxyphenyloxy)-3''-hydroxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(3''-(4'''-phenoxyphenyloxy)-4''-hydroxycyclohexyl)-1'-methylvinyl]-23,-25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(4''-(naphth-1-yloxy)-3''-methoxycyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-ethyl-1,14-dihydroxy-12-[2'-(3''-(naphth-1-yloxy)-4''-hydroxycyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-ethyl-1,14-dihydroxy-12-[2'-(4''-(naphth-1-yloxy)-3''-hydroxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(4''-(naphth-2-yloxy)-3''-methoxycyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-ethyl-1,14-dihydroxy-12-[2'-(4''-(naphth-2-yloxy)-3''-hydroxycyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-ethyl-1,14-dihydroxy-12-[2'-(3''-(napth-2-yloxy)-4''-hydroxycyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-ethyl-1-hydroxy-12-[2'-(4''-(naphth-2-yloxy)-3''-methoxycyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-ethyl-1,14-dihydroxy-12-[2'-(4''-(6'''-methoxynaphth-2-yloxy)-3''-methoxycyclohexyl)-1'-methylvinyl]-23,25-dimethoxy-13,19,21,27-tetramethyl-11,28-dioxa-4-azatricyclo [22.3.1.0⁴,⁹]octacos-18-ene-2,3,10,16-tetraone;

17-ethyl-1,14-dihydroxy-12-[2'-(3''-(6'''-methoxynaphth-2-yloxy)-4''-hydroxycyclohexyl)-1'-methylvinyl]-23,25-dimethoxy-13,19,21,27-tetramethyl-11,28-dioxa-4-azatricyclo [22.3.1.0⁴,⁹]octacos-18-ene-2,3,10,16-tetraone;

17-ethyl-1,14-dihydroxy-12-[2'-(4''-(6'''-methoxynaphth-2-yloxy)-3''-hydroxycyclohexyl)-1'-methylvinyl]-23,25-dimethoxy-13,19,21,27-tetramethyl-11,28-dioxa-4-azatricyclo [22.3.1.0⁴,⁹]octacos-18-ene-2,3,10,16-tetraone;

17-ethyl-1,14-dihydroxy-12-[2'-(4"-(4'''-methoxyphenyloxy)-3"-methoxycyclohexyl)-1'-methylvinyl]-23,25-dimethoxy-13,19,21,27-tetramethyl-11,28-dioxa-4-aza-tricyclo[22.3.1.0⁴,⁹]octacos-18-ene-2,3,10,16-tetraone;

17-ethyl-1,14-dihydroxy-12-[2'-(4"-(3'''-methoxyphenyloxy)-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(4"-(6'''-hydroxynaphth-2-yloxy)-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(4"-(4'''-hydroxyphenyloxy)-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(4"-(4'''-methylthiophenyloxy)-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(4"-(2'''-methylphenyloxy)-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(4"-(3'''-methylphenyloxy)-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(4"-(3''',4'''-dimethylphenyloxy)-3"-methoxycyclohexyl)-1'-methylvinyl]-23,25-dimethoxy-13,19,21,27-tetramethyl-11,28-dioxa-4-azatricyclo [22.3.1.0⁴,⁹]octacos-18-ene-2,3,10,16-tetraone;

17-ethyl-1,14-dihydroxy-12-[2'-(3"-(4'''-methoxyphenyloxy)-4"-hydroxycyclohexyl)-1'-methylvinyl]-23,25-dimethoxy-13,19,21,27-tetramethyl-11,28-dioxa-4-azatricyclo[22.3.1.0⁴,⁹]octacos-18ene-2,3,10,16-tetraone;

17-ethyl-1,14-dihydroxy-12-[2'-(4"-(4'''-methoxyphenyloxy)-3"-hydroxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(3"-(3'''-methoxyphenyloxy)-4"-hydroxycyclhexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(4"-(3'''-methoxyphenyloxy)-3"-hydroxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(3"-(4'''-hydroxyphenyloxy)-4"-hydroxycyclohexyl)-1'-methylvinyl]-23,25-dimethoxy-13,19,21,27-tetramethyl-11,28-dioxa-4-azatricylo[22.3.1.0⁴,⁹]octacos-18-ene-2,3,10,16-tetraone;

17-ethyl-1,14-dihydroxy-12-[2'-(4"-(4'''-hydroxyphenyloxy)-3"-hydroxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(4"-(6'''-hydroxynaphth-2-yloxy)-3"-hydroxycyclohexyl)-1'-methylvinyl]-23,25-dimethoxy-13,19,21,27-tetramethyl-11,28-dioxa-4- azatricyclo[22.3.1.0⁴,⁹]octacos-18-ene-2,3,10,16- tetraone;

17-ethyl-1,14-dihydroxy-12-[2'-(3"-(6'''-hydroxynaphth-2-yloxy)-4"-hydroxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(4"-(3''',4'''-dichlorophenyloxy)-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(4"-(phenanthr-9-yloxy)-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12--[2'-(4"-(3''',4'''-methylenedioxyphenyloxy)-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(4"-(2''',3'''-dihydrobenzofuran-5-yloxy)-3"-methoxycyclohexyl)-1'-methylvinyl]-23,25-dimethoxy-13,19,21,27-tetramethyl-11,28-dioxa-4-azatricyclo [22.3.1.0⁴,⁹]octacos-18-ene-2,3,10,16-tetraone;

17-allyl-1,14-dihydroxy-12-[2'-(4"-(naphth-2-yl)-3"-methoxycyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-Ethyl-1,14-hydroxy-12-[2'-(4"-(4'''-dimethylamino)phenyloxy-3"-hdyroxycyclohexyl)-1'-methylvinyl]-23,25-dimethoxy-13,19,21,27-tetramethyl-11,28-dioxa-4-azatricyclo[22.3.1.04,9]-octacos-18-ene-2,3,10,16-tetraone;

17-Ethyl-1,14-hydroxy-12-[2'-(4"-hydroxy-3"-(4'''-dimethylamino)phenyloxycyclohexyl)-1'-methylvinyl]-23,25-dimethoxy-13,19,21,27-tetramethyl-11,28-dioxa-4-azatricyclo [22.3.1.04,9]-octacos-18-ene-2,3,10,16-tetraone;

17-ethyl-1,14-dihydroxy-12-[2'-(4"-(1''',4'''-benzodioxane-6-yloxy)-3"-methoxycyclohexyl)-1'-methylvinyl]-23,25-dimethoxy-13,19,21,27-tetramethyl-11,28-dioxa-4-azatricyclo]22.3.1.0⁴,⁹]octacos-18-ene-2,3,-10,16-tetraone; and 17-ethyl-1,2,14-trihydroxy-12-[2'-(4"-(naphth-2-yloxy)-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-3,10,16-trione.

6. A compound which is selected from the group consisting of:
17-ethyl-1,14-dihydroxy-12-[2'-(4"-allyloxy-3"-methoxycyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-ethyl-1,14-dihydroxy-12-[2'-(4''-(2'''-butynyloxy)-3'''-methoxycyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-ethyl-1,14-dihydroxy-12-[2'-(4''-cinnamyloxy-3''-methoxycyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-ethyl-1,14-dihydroxy-12-[2'-(3''-methoxy-4''-phenyl propyloxycycylohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-ethyl-1,14-dihydroxy-12-[2'-(4''-allyloxy-3''-hydroxycyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-ethyl-1,14-dihydroxy-12-[2'-(3''-allyloxy-4''-hydroxycyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-ethyl-1,14-dihydroxy-12-[2'-(3''-hydroxy-4''-isopropyloxycyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-ethyl-1,14-dihydroxy-12-[2'-(4''-hydroxy-3''-isopropyloxycyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-ethyl-1,14-dihydroxy-12-[2'-(4''-sec-butenyloxy-3''-hydroxycyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-ethyl-1,14-dihydroxy-12-[2'-(3''-sec-butenyloxy-4''-hydroxycyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-ethyl-1,14-dihydroxy-12-[2'-(4''-(trans-2'''-butenyloxy)-3''-hydroxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(3''-(trans-2'''-butenyloxy)-4''-hydroxycyclohexyl)-1'-methylvinyl]-23,25-dimethoxy-13,19,21,27-tetramethyl-11,28-dioxa-4-azatricyclo [22.3.1.0⁴,⁹]octacos-18-ene-2,3,10,16-tetraone;

17-ethyl-1,14-dihydroxy-12-2'-(3''-hydroxy-4''-(3'''-methyl-2-butenyloxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(4''-hydroxy-3''-(3'''-methyl-2-butenyloxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(3''-hydroxy-4''-(2'''-methylpropenyloxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(4''-hydroxy-3''-(2'''-methylpropenyloxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(4''-cinnamyloxy-3''-hydroxycyclohexyl)-1'-methylvinyl -23,25-dimethoxy-13,19,21,27-tetramethyl-11,28-dioxa-4-azatricyclo-[22.3.1.0⁴,⁹]octacos-18-ene-2,3,10,16-tetraone;

17-ethyl-1,14-dihydroxy-12-[2'-(3''-cinnamyloxy-4''-hydroxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-hydroxy-12-[2'-(4''-sec-butenyloxy-3''-hydroxycyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-ethyl-1,14-hydroxy-12-[2'-(3''-sec-butenyloxy-4''-hydroxycyclohexyl)-1'-methylvinyl]-23,25-dimethoxy-13,19,21,27-tetramethyl-11,28-dioxa-4-azatricyclo-[22.3.1.04,9]octacos-18-ene-2,3,10,16-tetraone;

17-ethyl-1,14-hydroxy-12-[2'-(4''-cinnamyloxy-3''-methoxycyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-ethyl-1,14-hydroxy-12-[2'-(3''-methoxy-4''-phenylpropyloxycyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-ethyl-1,14-dihydroxy-12-[2'-(4''-allyloxy-3''-methoxycyclohexyl)-1'-methylvinyl]-23,25-dimethoxy-13,19,21,27-tetramethyl-11,28-dioxa-4-azatricylo-[22.3.1.0⁴,⁹]octacos-18-ene-2,3,10,16-tetraone;

17-ethyl-1,14-hydroxy-12-[2'''-(4''-(2'''-butynyloxy)-3''-methoxycyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-ethyl-1,14-hydroxy-12-[2'-(4''-cinnamyloxy-3''-methoxycyclohexyl)-1'-methylvinyl]-23,25-dimethoxy-13,19,21,27-tetramethyl-11,28-dioxa-4-azatricyclo[2.3.1.0⁴,⁹]octacos-18 -ene-2,3,10,16-tetraone;

17-ethyl-1,14-hydroxy-12-[2'-(3''-methoxy-4''-phenylpropyloxycyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-ethyl-1,14-hydroxy-12-[2'-(4''-allyloxy-3''-hydroxycyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-ethyl-1,14-hydroxy-12-[2'-(3''-allyloxy-4''-hydroxycyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-ethyl-1,14-hydroxy-12-[2'-(3''-hydroxy-4''-isopropyloxycyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-ethyl-1,14-hydroxy-12-[2'-(4''-hydroxy-3''-isopropyloxycyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-ethyl-1,14-hydroxy-12-[2'-(4''-(trans-2'''-butenyloxy)-3''-hydroxycyclohexyl)-1'-methylvinyl]-

23,25-dimethoxy-13,19,21,27-tetramethyl-11,28-dioxa-4-azatricyclo-[22.3.1.0^{4,9}]octacos-18-ene-2,3,10,16-tetraone;

17-ethyl-1,14-hydroxy-12-[2'-(3'''-(trans-2''''-butenyloxy)-4''-hydroxycyclohexyl)-1'-methylvinyl]-23,25-dimethoxy-13,19,21,27-tetramethyl-11,28-dioxa-4-azatricyclo-[22.3.1.0^{4,9}]octacos-18-ene-2,3,10,16-tetraone;

17-ethyl-1,14-hydroxy-12-[2'-(3''-hydroxy-4''-(3'''-methyl-2-butenyloxycyclohexyl)-1'-methylvinyl]-23,25-dimethoxy-13,19,21,27-tetramethyl-11,28-dioxa-4-azatricyclo[22.3.1.0^{4,9} octacos-18-ene-2,3,10,16-tetraone;

17-ethyl-1,14-hydroxy-12-[2'-(4''-hydroxy-3''-(3'''-methyl-2-butenyloxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-ethyl-1,14-hydroxy-12-[2'-(3''-hydroxy-4''-(2''''-methylpropenyloxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-ethyl-1,14-hydroxy-12-[2'-(4''-hydroxy-3''-(2''''-methylpropenyloxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-ethyl-1,14-hydroxy-12-[2'-(3''-cinnamyloxy-4''-hydroxycyclohexyl)-1'-methylvinyl]-23,25-dimethoxy-13,19,21,27-tetramethyl-11,28-dioxa-4-azatricyclo-[22.3.1.0^{4,9}]octacos-18-ene-2,3,10,16-tetraone;

17-ethyl-1,14-dihydroxy-12-[2'-(4''-sec-phenethyloxy-3''-methoxycyclohexyl)-1'-methylvinyl]-23,25-dimethoxy-13,19,21,27-tetramethyl-11,28-dioxa-4-azatricyclo [22.3.1.0^{4,9}]octacos-18-ene-2,3,10,16-tetraone;

17-ethyl-1,14-dihydroxy-12-[2'-(4''-(2'''-methylcinnamyloxy)-3''-methoxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-ethyl-1,14-dihydroxy-12-[2'-(4''-(4'''-methyl-2''',4'''-hexadienyloxy)-3''-methoxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3-10,16-tetraone;

17-ethyl-1,14-dihydroxy-12-[2'-(4''-(p-methoxycinnamyloxy)-3''-methoxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-ethyl-1,14-dihydroxy-12-[2'-(4''-(3''',4'''-methylenedioxycinnamyloxy)-3''-methoxycyclohexyl)-1'-methyl-vinyl]-23,25-dimethoxy-13,19,21,27-tetramethyl-11,28-dioxa-4-azatricyclo]22.3.1.0^{4,9}]-octacos-18-ene-2,3,10,16-tetraone;

17-ethyl-1,14-dihydroxy-12-[2'-(4''-(4''',4'''-dimethyl-2'''-trans-pentenyloxy)-3''-methoxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-ethyl-1,14-dihydroxy-12-[2'-(4''-(-3''''-cyclohexyl-2'''-trans-propenyloxy)-3''-methoxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-ethyl-1,14-dihydroxy-12-[2'-(4''-p-fluorocinnamyloxy-3''-methoxycyclohexyl)-1'-methylvinyl]-23,25-dimethoxy-13,19,21,27-tetramethyl-11,28-dioxa-4-azatricyclo[22.3.1.0^{4,9}] octacos-18-ene-2,3,10,16-tetraone;

17-ethyl-1,14-dihydroxy-12-[2'-(4''-p-chlorocinnamyloxy-3''-methoxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-ethyl-1,14-dihydroxy-12-[2'-(4''-p-bromo cinnamyloxy-3''-methoxycyclohexyl)-1'-methylvinyl]-23,25-dimethoxy-13,19,21,27-tetramethyl-11,28-dioxa-4-azatricyclo-[22.3.1.0^{4,9}]octacos-18-ene-2,3,10,16-tetraone;

17-ethyl-1,14-dihydroxy-12-[2'-(3''-methoxy-4''-p-fluorophenylpropyloxycylohexyl)-1'-methylvinyl]-23,25-dimethoxy-13,19,21,27-tetramethyl-11,28-dioxa-4-azatricyclo[22.3.1.0^{4,9}0 octacos-18-ene-2,3,10,16-tetraone;

17-ethyl-1,14-hydroxy-12-[2'-(3'',4''-diallyloxycyclohexyl)-1'-methylvinyl]-23,25-dimethoxy-13,19,21,27-tetramethyl-11,28-dioxa-4-azatricyclo[22.3.1.0^{4,9}]-octacos-18-ene-2,3,10,16-tetraone;

17-ethyl-1,14-hydroxy-12-[2'-(3'',4''-dipropyloxycyclohexyl)-1'-methylvinyl]23,25-dimethoxy-13,19,21,27-tetramethyl-11,28-dioxa-4-azatircyclo[22.3.1.0^{4,9}]-octacos-18-ene-2,3,10,16-tetraone;

17-ethyl-1,14-dihydroxy-12-[2'-(4''-(2'''-benzylamino)ethoxy-3''-methoxycyclohexyl)-1'-methylvinyl]-23,25-dimethoxy-13,19,21,27-tetramethyl-11,28-dioxa-4-azatricyclo[22.3.1.04,9]octacos-18-ene-2,3,10,16,-tetraone;

17-ethyl-1,14-hydroxy-12-[2'-(4''-(2'''-benzylamino) ethoxy-3''-methoxycyclohexyl)-1'-methylvinyl]-23,25-dimethoxy-13,19,21,27-tetramethyl-11,28-dioxa-4-azatricyclo[22.3.1.04,9]octacos-18-ene-2,3,10,16-tetraone;

17-ethyl-1,14-dihydroxy-12-[2'-(4''-(2-benzyloxyethoxy)-3''-methoxycyclohexyl)-1'-methylvinyl]-23,25-dimethoxy-13,19,21,27-tetramethyl-11,28-dioxa-4-azatricyclo[22.3.1.04,9]octacos-18-ene-2,3,10,16-tetraone;

17-ethyl-1,14-dihydroxy-12-[2'-(4''-benzyl oxymethyoxy-3''-methoxycyclohexyl)-1'-methylvinyl]-23,25-dimethoxy-13,19,21,27-tetramethyl-11,28-dioxa-4-azatricyclo-[22.3.1.0^{4,9}]octacos-18-ene-2,3,10,16-tetraone;

17-ethyl-1,14-dihydroxy-12-[2'-(4''-napth-2-yloxy)-3''-allyloxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-ethyl-1,14-dihydroxy-12-[2'-(4''-(ethoxycarbomethoxy)-3''-methoxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-ethyl-1,14-dihydroxy-12-[2'-(4''-(p-hydroxy cinnamyloxy)-3''-methoxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-ethyl-1,14-hydroxy-12-[2'-(4''-(p-hydroxycinnamyloxy)-3''-methoxycyclohexyl)-1'-methylvinyl]-23,15-dimethoxy-13,19,21,17-tetramethyl-11,28-dioxa-4-azatricyclo-[22.3.1.0^{4,9}]octacos-18-ene-2,3,10,16-tetraone;

17-ethyl-1,14-dihydroxy-12-[2'-(4"-(2'''-phenyl-2'''-oxo-ethyloxy)-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-hydroxy-12-[2'-(4"-(2'''-phenyl-2'''-oxoethyloxy)-3"-methoxycyclohexyl-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[-2'-(4"-(2'''-phenyl-2'''-oxo-ethyloxy)-3"-hydroxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(4"-(2'''-(3''''-methoxyphenyl)-2'''-oxo-ethyloxy)-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1-hydroxy-12-[2'-(4"-(2'''-(3''''-methoxyphenyl)-2'''-oxo-ethyloxy)-3"-methoxycyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-ethyl-1,14dihydroxy-12-[2'-(4"-(2'''-(3''''-hydroxyphenyl)-2'''-oxo-ethyloxy)-3"-methoxycyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-ethyl-1,14-dihydroxy-12-[2'-(4"-(2'''-(4''''-methoxyphenyl)-2'''-oxo-ethyloxy)-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17ethyl-1hydroxy-12-[2'-(4"-(2'''-(4''''-methoxyphenyl)-2'''-oxo-ethyloxy-3"-methoxycyclohexyl)-1'-methylvinyl]-23,25-dimethoxy-13,19,21,27-tetramethyl-11,28-dioxa4-azatricyclo-[22.3.1.0⁴,⁹]octacos-18-ene-2,3,10,16-tetraone;

17-ethyl-1,14-dihydroxy-12-[2'-(4"-(2'''-(4''''-methoxyphenyl)-2'''-oxo-ethyloxy)-3"-hydroxycyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-ethyl-1,14-dihydroxy-12-[2'-4"-(2'''-3'''', 5''''-dimethoxyphenyl)-2'''-oxo-ethyloxy)-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1-hydroxy-12-[2'-(4"-(2'''-(3'''', 5''''-dimethoxyphenyl)-2'''-oxo-ethyloxy)-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(4"-(2'''-(3'''',5''''-dimethoxyphenyl)-2'''-oxo-ethyloxy)-3"-hydroxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(4"-(2'''-(3'''',5''''-difluorophenyl)-2'''-oxo-ethyloxy)-3"-methoxycyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-ethyl-1-hydroxy-12-[2'-(4"-(2'''-(3'''',5''''-didifluorophenyl-2'''-oxo-ethyloxy)-3"-methoxycyclohexyl)-1'-methylvinyl]-23,25-dimethoxy-13,19,21,27-tetramethyl-11,28-dioxa-4-azatricyclo-22.3.1.0⁴,⁹]octacos-18-ene2,3,10,16-tetraone;

17-ethyl-1,14-dihydroxy-12-[2'-(4"(2'''-(3'''',5''''-difluorophenyl)-2'''-oxo-ethyloxy)-3"-hydroxycyclohexyl) -1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(4"(2'''-(4''''-hydroxyphenyl)-2'''-oxo-ethyloxy)-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1-hydroxy-12-[2'-(4"-(2'''-(4''''-hydroxyphenyl)-2'''-oxo-ethyloxy)-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(4"-(2'''-(4''''-hydroxyphenyl) -2'''-oxo-ethyloxy)-3"-hydroxycyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-ethyl-1,14-dihydroxy-12-[2'-(4"-(2'''-phenyl-2'''-hydroxyethyloxy)-3"-methoxycyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-ethyl-1-hydroxy-12-[2'-(4"-(2'-"-phenyl-2'''-hydroxyethyloxy)-3"-methoxycyclohexyl)-1'-methylvinyl]-23,25-dimethoxy-13,19,21,27-tetramethyl-11,28-dioxa-4-azatricyclo22.3.1.0⁴,⁹]octacos-18-ene-2,3,10,16-tetraone;

17-ethyl-1,14-dihydroxy-12-[2'-(4"-(2'-"-phenyl-2'''-hydroxyethyloxy)-3"-hydroxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(4"-(2'''-(3''''-methoxyphenyl)-2'''-hydroxyethyloxy) -3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1-hydroxy-12-[2'-(4"-(2'''-(3''''-methoxyphenyl) -2'''-hydroxyethyloxy-3"-methoxycyclohexyl)-1'-methylvinyl]-23,25-dimethoxy-13,19,21,27-tetramethyl-11,28-dioxa4-azatricyclo-[22.3.1.0⁴,⁹]octacos-18ene-2,3,10,16-tetraone;

17-ethyl-1,14-dihydroxy-12-[2'-(4"-(2'''-(3''''-methoxyphenyl)-2'''-hydroxyethyloxy)-3"-hydroxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(4"-(2'''-(3'''', 5''''-dimethoxyphenyl)-2'''-hydroxyethyloxy)-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1-hydroxy-12-[2'-(4"-(2'''-(3'''',5''''-dimethoxyphenyl)-2'''-hydroxyethyloxy)-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(4"-(2''' ∝ -(3'''',5''''-dimethoxyphenyl)-2'''-hydroxyethyloxy)-3"-hydroxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(4''-(2'''-(3'''',5''''-difluorophenyl)-2'''hydroxyethyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-enen-2,3,10,16-tetraone;

17-ethyl-1-hydroxy-12-[2'-(4''-(2'''-(3'''',5''''-difluorophenyl)-2'''-hydroxyethyloxy)-3''-methoxycyclohexyl)-1'-methylvinyl]-23,25-dimethoxy-13,19,21,27-tetramethyl-11,28-dioxa-4-azatricyclo[22.2.1.0$^{4,9}$]octacos-18-ene-2,3,10,16-tetraone;

17-ethyl-1,14-dihydroxy-12-[2'-(4''-(2'''-(3'''',5''''-difluorophenyl)-2'''-hydroxyethyloxy)-3''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4''-(2'''-(4''''-hydroxyphenyl)-2'''-hydroxyethyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1hydroxy-12-[2'-(4''-(2'''-(4''''-hydroxyphenyl)-2'''-hydroxyethyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(2'''-(4''''-hydroxyphenyl)-2'''-hydroxyethyloxy)-3''-hydroxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone;

17-ethyl-1,14-dihydroxy-12-[2'-(4''-(m-fluorocinnamyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'--(4''-(3''',5'''-difluorocinnamyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10, 16-tetraone;

17-ethyl-1,14-dihydroxy-12-[2'-(4''-(m-nitrocinnamyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'--(4''-(3'''-phenyl-2'''-propynyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4''--(2'''-phenyl-2'''-propenyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4''-(p-hydroxycinnamyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4''-(p-hydroxyphenpropyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4''-(m-hydroxycinnamyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4''-(m-hydroxymethylbenzyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4''-hydroxycinnamyloxy)-3''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4''-(3''',5'''-difluorocinnamyloxy)-3''-hydroxycyclohexyl)-1'-methylvinyl]-23,25-dimethoxy-13,19,21,27-tetramethyl-11,28-dioxa-4-azatricyclo [22.3.1.0$^{4,9}$]octacos-18-ene-2,3,10,16-tetraone;

17-ethyl-1,14-dihydroxy-12-[2'-(4''-(p-carboxybenzyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4''-(m-carboxybenzyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4''-(m-carbomethoxybenzyloxy)-3''-methoxycyclohexyl)1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4''-(m-isopropylcarboxamidobenzyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4''-(m-butylcarboxamidobenzyloxy)-3''-methoxycyclohexy)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4''-acetamidoxy-3''-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone;

17-ethyl-1,14-dihydroxy-12-[2'-(4''-carboxymethoxy-3''-methoxycyclohexyl)-1'-methylvinyl]-23,25-dimethoxy-13,19,21,27-tetramethyl-11,28-dioxa-4-azatricyclo[22.2.1.0$^{4,9}$]octacos-18-ene-2,3,10,16-tetraone;

17-ethyl-1,14-dihydroxy-12-[2'-(4''-(N-phenylacetamidoxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4''-(N-benzylacetamidoxy)-3''-methoxycyclohexyl)-1'-methylvinyl]-23,25-dimethoxy-13,19,21,27-tetramethyl-11,28-dioxa-4-azatricyclo[2.3.1.0$^{4,9}$]octacos-18-ene-2,3,10,16-tetraone;

17-ethyl-1-hydroxy-12-[2'-(4''-carboxymethyl-3''-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone;

17-ethyl-1-hydroxy-12-[2'-(4''-(N-benzylamidoxymethoxy-3''-methoxycyclohexyl)-1'-methylvinyl]-23,25-dimethoxy-13,19,21,27-tetramethyl- 11,28-dioxa-4-azatricyclo-[22.3.1.0⁴,⁹]octacos-18-ene-2,3,10,16-tetraone;

17-ethyl-1-hydroxy-12-[2'-(4"-(N-methyltyrosine)amidoxy-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(4"-(2'''-(m-methylphenyl)-2''''-oxo-ethyloxy)-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(4"-(2'''-(p-methylphenyl)-2''''-oxo-ethyloxy)-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(4"-(2'''-phenyl-2''''-hydroxyethyloxy)-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(4"-(2'''-(m-methylphenyl)-2''''-hydroxyethyloxy)-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(4"-(2'''-(m-ethylphenyl)-2''''-oxo-ethyloxy)-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(4"-(2'''-phenylethyloxy)-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(4"-(2'''-phenyl-2''''-acetoxyethyloxy)-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(4"-(2'''-morpholinoethyloxy)-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(4"-(naphth-2-ylmethyloxy)-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(4"'-(4"'',5'''-methylenedioxybenzyloxy)-3"-methoxycyclohexyl-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(4"-(4'''-N,N-dimethylaminophenyloxy)-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(4"-(3'''-fluorophenyloxy)-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(4"-(3'''-(2''''-dioxolanylphenyloxy)-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(4"-(3'''-formylphenyloxy)-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(4"-(3'''-carboxyphenyloxy)-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(4"-(3''',4'''-dimethoxyphenyloxy)-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(4"-(4'''-trifluoromethylphenyloxy)-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1,14-dihydroxy-12-[2'-(4"-(3''',5'''-bis(trifluoromethyl)phenyloxy)-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1-hydroxy-12-[2'-(4"-(4'''-methylphenyloxy)-3"-hydroxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1-hydroxy-12-[2'-(4"-hydroxy-3"-(4'''-methylphenyloxy)cyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1hydroxy-12-[2'-(4"-(4'''-hydroxyphenyloxy)-3"-hydroxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1hydroxy-12-[2'-(4"-hydroxy-3"-(4'''-hydroxyphenyloxy)cyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1hydroxy-12-[2'-(4"-(4'''-hydroxymethylphenyloxy)-3"-hydroxycyclohexyl)-1'-methylvinyl]-23,25-dimethoxy-13,19,21,27-tetramethyl-11,28-dioxa-4-azatricyclo[22.3.1.0⁴,⁹]-octacos-18-ene-2,3,10,16-tetraone;

17-ethyl-1hydroxy-12-[2'-(4"-hydroxy-3"-(4'''-hydroxymethylphenyloxy)cyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1hydroxy-12-[2'-(4"hydroxy-3"-(4'''-formylphenyloxy)cyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-1hydroxy-12-[2'-(4"-(4'''-N,N-dimethylaminiphenyloxy)-3"-hydroxycyclohexyl)-1'-methylvinyl]-23,25-dimethoxy-13,19,21,27-tetramethyl-11,28-dioxa-4-azatricyclo ]22.3.1.0⁴,⁹]octacos-18-ene-2,3,10,16-tetraone;

17-ethyl-1hydroxy-12-[2'-(4"-hydroxy-3"-(4'''-N,N-dimethylaminophenyloxy)cyclohexyl)-1'-methylvinyl]-23,25-dimethoxy-13,19,21,27-tetramethyl11,28-dioxa-4-azatricyclo[22.3.1.0^{4,9}]octacos-18-ene-2,3,10,16-tetraone;

17-ethyl-1hydroxy-12-[2'-(4''-phenyloxy)-3''-hydroxycyclohexyl)-1'-methylvinyl]-23,25-dimethoxy-13,19,21,27-tetramethyl-11,28-dioxa-4-azatricyclo]22.3.1.0^{4,9}]octacos-18-ene-2,3,10,16-tetraone;

17-ethyl-1hydroxy-12-[2'-(4''-hydroxy-3''-phenyloxy)cyclohexyl)-1'-methylvinyl]-23,25-dimethoxy-13,19,21,27-tetramethyl-11,28-dioxa-4-azatricyclo]22.3.1.0^{4,9}]octacos-18-ene-2,3,10,16-tetraone;

17-ethyl-1hydroxy-12-[2'-(4''-(4'''-methoxyphenyloxy)-3''-hydroxycyclohexyl)-1'-methylvinyl]-23,25-dimethoxy-13,19,21,27-tetramethyl-11,28-dioxa -4-azatricyclo[22.3.1.0^{4,9}]octacos-18-ene-2,3,10,16-tetraone and;

17-ethyl-1hydroxy-12-[2'-(4''-hydroxy-3''-(4'''-methoxyphenyloxy) cyclohexyl)-1'-methylvinyl]-23,25-dimethoxy-13,19,21,27-tetramethyl-11,28-dioxa -4-azatricyclo[22.3.1.0^{4,9}]octacos-18-ene-2,3,10,16-tetraone;

17-ethyl-1hydroxy-12-[2'-(4''-(3'''-methoxyphenyloxy)-3''-hydroxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone; and 17-ethyl-1hydroxy-12-[2'-(4''-hydroxy-3''-(3'''-methoxyphenyloxy) cyclohexyl)-1' -methylvinyl]-23,25-dimethoxy-13,19,21,27-tetramethyl-11,28-dioxa-4-azatricyclo[22.3.1.0^{4,9}]octacos-18-ene-2,3,10,16-tetraone.

7. A compound which is:

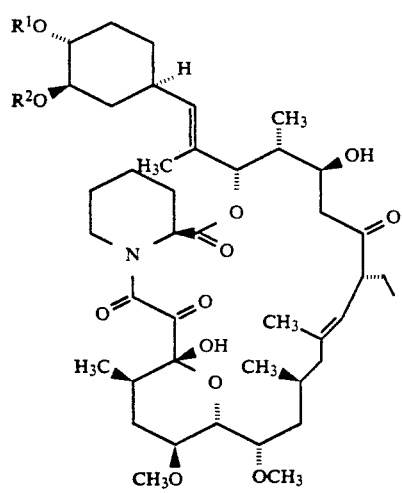

wherein $R^1$ and $R^2$ are selected from the following combinations:

| | $R^1$ | $R^2$ |
|---|---|---|
| a) | phenyl | CH$_3$ |
| b) | phenyl | H |
| c) | 4-CH$_3$O-phenyl | CH$_3$ |
| d) | 4-HO-phenyl | CH$_3$ |
| e) | 4-CH$_3$O-phenyl | H |
| f) | 4-HO-phenyl | H |
| g) | 4-F-phenyl | CH$_3$ |
| h) | 3-OCH$_3$-phenyl | CH$_3$ |
| i) | 3-OCH$_3$-phenyl | H |
| j) | H | phenyl |
| k) | H | 4-CH$_3$O-phenyl |
| l) | H | 4-HO-phenyl |
| m) | naphthyl | CH$_3$ |
| n) | naphthyl | H |
| o) | 6-CH$_3$O-naphthyl | CH$_3$ |

-continued
| | R¹ | R² |
|---|---|---|
| p) | 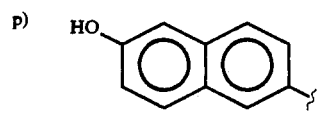 | CH₃ |
| q) | 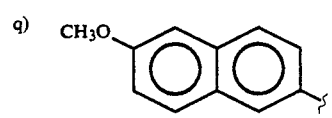 | H |
| r) | 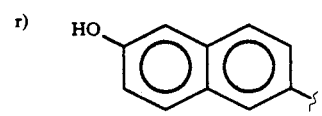 | H. |
8. The compound of claim 7 which is:
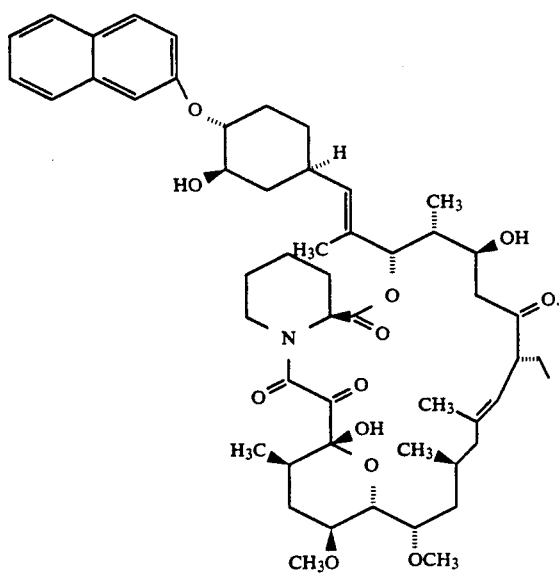
9. The compound of claim 7 which is:
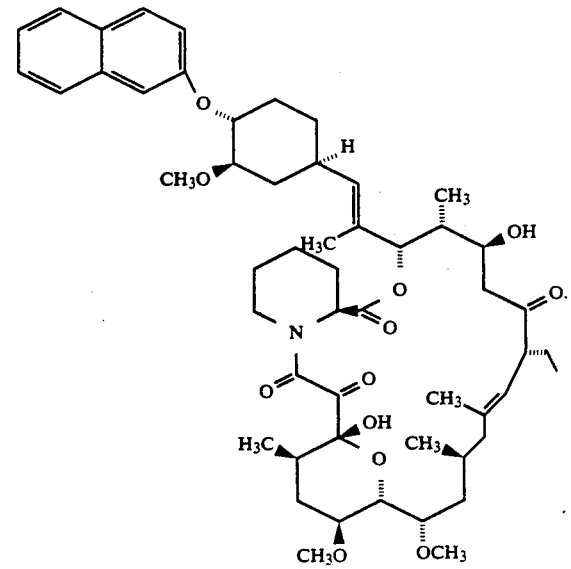
10. A compound which is:
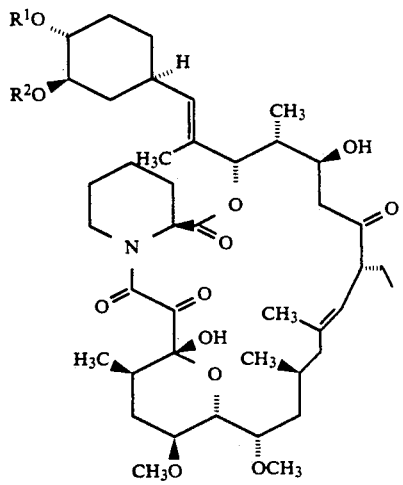
wherein R¹ and R² are selected from the following combinations:
| | R¹ | R² |
|---|---|---|
| a) | 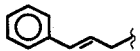 | CH₃ |
| b) |  | H |
| c) |  | CH₃ |
| d) | 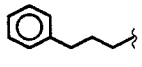 | H |
| e) | 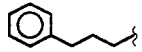 | CH₃ |

-continued

| | R¹ | R² |
|---|---|---|
| f) | 4-CH₃O-C₆H₄-CH=CH-CH₂- | H |
| g) | 4-CH₃O-C₆H₄-CH₂-CH₂-CH₂- | CH₃ |
| h) | 4-HO-C₆H₄-CH=CH-CH₂- | CH₃ |
| i) | 4-HO-C₆H₄-CH=CH-CH₂- | H |
| j) | C₆H₅-C(=O)-CH₂- | CH₃ |
| k) | C₆H₅-C(=O)-CH₂- | H |
| l) | 3-CH₃-C₆H₄-C(=O)-CH₂- | CH₃ |
| m) | 3-CH₃-C₆H₄-C(=O)-CH₂- | H |
| n) | 3,5-(CH₃)₂-C₆H₃-C(=O)-CH₂- | CH₃ |
| o) | 3,5-(CH₃)₂-C₆H₃-C(=O)-CH₂- | H |
| p) | 3,5-F₂-C₆H₃-C(=O)-CH₂- | CH₃ |
| q) | 3,5-F₂-C₆H₃-C(=O)-CH₂- | H |
| r) | C₆H₅-CH(OH)-CH₂- | CH₃ |
| s) | C₆H₅-CH(OH)-CH₂- | H |
| t) | 3-CH₃-C₆H₄-CH(OH)-CH₂- | CH₃ |
| u) | 3-CH₃-C₆H₄-CH(OH)-CH₂- | H |
| v) | 3,5-(CH₃)₂-C₆H₃-CH(OH)-CH₂- | CH₃ |
| w) | 3,5-(CH₃)₂-C₆H₃-CH(OH)-CH₂- | H |
| x) | 3,5-F₂-C₆H₃-CH(OH)-CH₂- | CH₃ |
| y) | 3,5-F₂-C₆H₃-CH(OH)-CH₂- | H |
| z) | C₆H₅-CH₂-CH₂- | CH₃ |
| aa) | 3-HO-C₆H₄-CH=CH-CH₂- | CH₃ |
| bb) | 4-CH₃-C₆H₄-CH=CH-CH₂- | CH₃ |
| cc) | 4-CH₃-C₆H₄-CH₂-CH₂-CH₂- | CH₃ |
| dd) | 3-CH₃-C₆H₄-CH₂-CH₂-CH₂- | CH₃ |
| ee) | 4-HO-C₆H₄-CH₂-CH₂-CH₂- | CH₃ |
| ff) | 4-F-C₆H₄-CH=CH-CH₂- | CH₃ |
| gg) | 3,5-F₂-C₆H₃-CH=CH-CH₂- | CH₃ |
| hh) | H | C₆H₅-CH=CH-CH₂- |
| ii) | CH₂=CH-CH₂- | CH₃ |
| jj) | CH₂=CH-CH₂- | H |

| | -continued | |
|---|---|---|
| | R¹ | R² |
| kk) | H |  |
11. The compound of claim 10 which is:
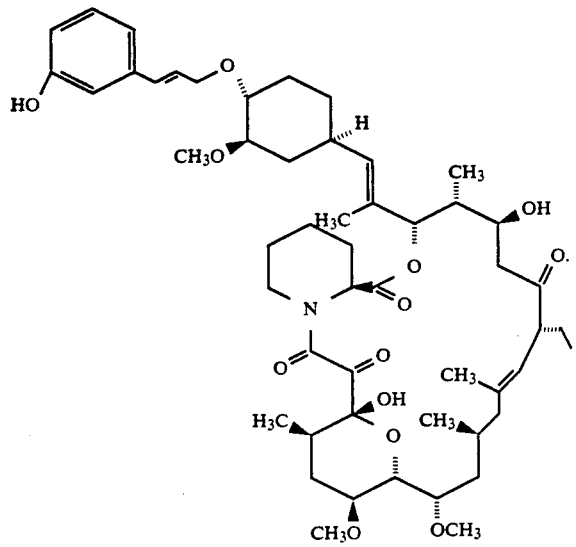
12. The compound of claim 10 which is:
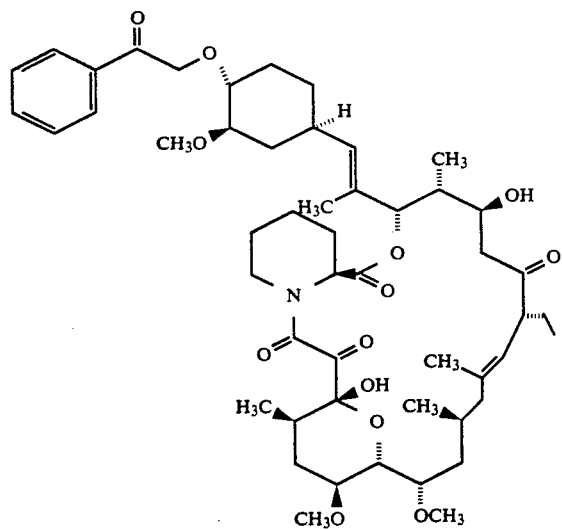
13. The compound of claim 10 which is:
14. The compound of claim 10 which is:
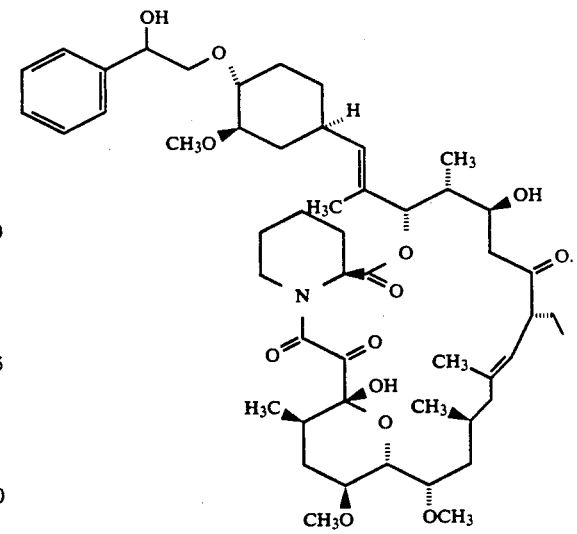
15. The compound of claim 10 which is:
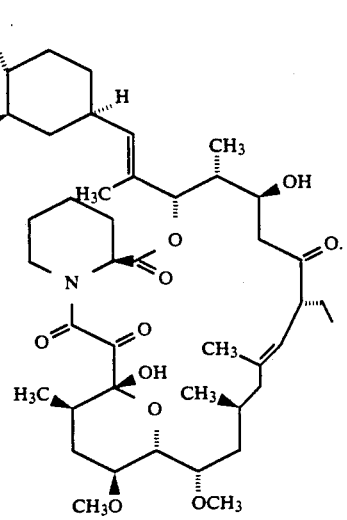
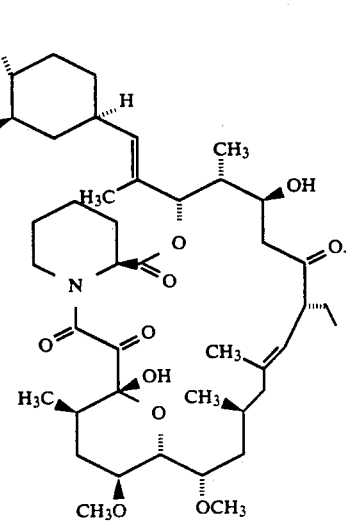
* * * * *